US011266638B2

(12) United States Patent
Houston et al.

(10) Patent No.: US 11,266,638 B2
(45) Date of Patent: Mar. 8, 2022

(54) CHOLINE SALT FORMS OF AN HIV CAPSID INHIBITOR

(71) Applicant: Gilead Sciences, Inc., Foster City, CA (US)

(72) Inventors: Travis Lee Houston, Lafayette, IN (US); Bing Shi, Redwood City, CA (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

(21) Appl. No.: 16/892,377

(22) Filed: Jun. 4, 2020

(65) Prior Publication Data
US 2020/0397772 A1 Dec. 24, 2020

Related U.S. Application Data

(62) Division of application No. 15/998,717, filed on Aug. 16, 2018, now Pat. No. 10,849,892.

(60) Provisional application No. 62/546,974, filed on Aug. 17, 2017.

(51) Int. Cl.
C07D 401/14 (2006.01)
A61K 31/454 (2006.01)
A61P 31/18 (2006.01)
A61K 45/06 (2006.01)

(52) U.S. Cl.
CPC ............ A61K 31/454 (2013.01); A61K 45/06 (2013.01); A61P 31/18 (2018.01); C07D 401/14 (2013.01)

(58) Field of Classification Search
CPC .................................................. C07D 401/14
See application file for complete search history.

(56) References Cited

U.S. PATENT DOCUMENTS

| | | | |
|---|---|---|---|
| 3,845,770 A | 11/1974 | Theeuwes et al. | |
| 4,326,525 A | 4/1982 | Swanson et al. | |
| 4,816,570 A | 3/1989 | Farquhar | |
| 4,902,514 A | 2/1990 | Barclay et al. | |
| 4,968,788 A | 11/1990 | Farquhar | |
| 4,992,445 A | 2/1991 | Lawter et al. | |
| 5,001,139 A | 3/1991 | Lawter et al. | |
| 5,023,252 A | 6/1991 | Hseih | |
| 5,616,345 A | 4/1997 | Geoghegan et al. | |
| 5,663,159 A | 9/1997 | Starrett, Jr. et al. | |
| 5,792,756 A | 8/1998 | Starrett, Jr. et al. | |
| 5,922,695 A | 7/1999 | Arimilli et al. | |
| 5,935,946 A | 8/1999 | Munger, Jr. et al. | |
| 5,977,089 A | 11/1999 | Arimilli et al. | |
| 7,390,791 B2 | 6/2008 | Becker et al. | |
| 7,803,788 B2 | 9/2010 | Becker et al. | |
| 8,263,627 B2 | 9/2012 | Barrow et al. | |
| 8,748,412 B2 | 6/2014 | Liao et al. | |
| 8,754,065 B2 | 6/2014 | Liu et al. | |
| 8,835,488 B2 | 9/2014 | Yamashita et al. | |
| 9,012,441 B2 | 4/2015 | Bondy et al. | |
| 9,050,344 B2 | 6/2015 | Brizgys et al. | |
| 9,220,710 B2 | 12/2015 | Bondy et al. | |
| 9,540,343 B2 | 1/2017 | Bondy et al. | |
| 9,670,205 B2 | 6/2017 | Aktoudianakis et al. | |
| 9,789,089 B2 | 10/2017 | Bondy et al. | |
| 9,873,680 B2 | 1/2018 | Brizgys et al. | |
| 9,944,619 B2 | 4/2018 | Bondy et al. | |
| 9,951,043 B2 | 4/2018 | Brizgys et al. | |
| 10,071,985 B2 | 9/2018 | Graupe et al. | |
| 10,370,342 B2 | 8/2019 | Chin et al. | |
| 10,370,358 B2 | 8/2019 | Bondy et al. | |
| 10,640,499 B2 | 5/2020 | Chin et al. | |
| 10,654,827 B2 | 5/2020 | Graupe et al. | |
| 10,696,657 B2 | 6/2020 | Vandehey | |
| 10,836,746 B2 | 11/2020 | Brizgys et al. | |
| 10,849,892 B2* | 12/2020 | Houston | A61K 31/454 |
| 11,117,886 B2 | 9/2021 | Vandehey et al. | |
| 2005/0282805 A1 | 12/2005 | Hangeland et al. | |
| 2007/0083045 A1 | 4/2007 | Di Francesco et al. | |
| 2008/0234251 A1 | 9/2008 | Doherty et al. | |
| 2008/0306050 A1 | 12/2008 | Doherty et al. | |
| 2010/0029585 A1 | 2/2010 | Dietsch et al. | |
| 2010/0129306 A1 | 5/2010 | Julien et al. | |
| 2010/0143301 A1 | 6/2010 | Desai et al. | |
| 2010/0249176 A1 | 9/2010 | Barrow et al. | |
| 2011/0092485 A1 | 4/2011 | Burgess et al. | |
| 2011/0118235 A1 | 5/2011 | Burgess et al. | |
| 2012/0045761 A1 | 2/2012 | Jagannath et al. | |
| 2012/0082658 A1 | 4/2012 | Hershberg | |

(Continued)

FOREIGN PATENT DOCUMENTS

CN 101910133 A 12/2010
WO WO 1991/19721 12/1991

(Continued)

OTHER PUBLICATIONS

[No Author Listed], "2-[9-(Difluoromethyl)-5,5-difluoro-7,8-diazatricyclo[4.4.0.02,4]nona-1(6),8-dien-7-yl]acetic acid," PubChem CID 71186949, Mar. 21, 2013, 18 pages.

[No Author Listed], "3-Methyl-3-methylsulfonylbut-1-yne," PubChem CID 14241469, Feb. 9, 2002, 16 pages.

[No Author Listed], CAS registry No. 1620056-83-8, Aug. 6, 2014, 1 page.

AU Office Action dated Oct. 18, 2017 for Australian Application No. 2016262671, 3 pages.

(Continued)

Primary Examiner — John S Kenyon
(74) Attorney, Agent, or Firm — Fish & Richardson P.C.

(57) ABSTRACT

The present disclosure relates to choline salts, and crystalline forms thereof, of a compound which is N—((S-1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3- (trifluoromethyl)-3b,4,4a,5-tetrahydro-1H-cyclopropa[3,4]cyclopenta[1,2-c]pyrazol-1-yl) acetamide, which is useful in the treatment and prevention of a Retroviridae viral infection including an infection caused by the HIV virus.

23 Claims, 10 Drawing Sheets

(56) References Cited

U.S. PATENT DOCUMENTS

| | | |
|---|---|---|
| 2012/0219615 A1 | 8/2012 | Coukos et al. |
| 2013/0165489 A1 | 6/2013 | Cocklin et al. |
| 2013/0251673 A1 | 9/2013 | Flores et al. |
| 2014/0045849 A1 | 2/2014 | McGowan et al. |
| 2014/0066432 A1 | 3/2014 | Burgess et al. |
| 2014/0073642 A1 | 3/2014 | Embrechts et al. |
| 2014/0088085 A1 | 3/2014 | Burgess et al. |
| 2014/0142085 A1 | 5/2014 | Bondy et al. |
| 2014/0221346 A1 | 8/2014 | Halcomb et al. |
| 2014/0221347 A1 | 8/2014 | Brizgys et al. |
| 2014/0221356 A1 | 8/2014 | Jin et al. |
| 2014/0221378 A1 | 8/2014 | Miyazaki et al. |
| 2014/0221380 A1 | 8/2014 | Miyazaki et al. |
| 2014/0221417 A1 | 8/2014 | Halcomb et al. |
| 2014/0221421 A1 | 8/2014 | Bondy et al. |
| 2014/0275167 A1 | 9/2014 | Hartman |
| 2014/0296266 A1 | 10/2014 | Hu et al. |
| 2014/0303164 A1 | 10/2014 | Brizgys et al. |
| 2014/0350031 A1 | 11/2014 | McGowan et al. |
| 2016/0067224 A1 | 3/2016 | Bondy et al. |
| 2016/0083368 A1 | 3/2016 | Brizgys et al. |
| 2016/0108030 A1 | 4/2016 | Brizgys et al. |
| 2016/0250215 A1 | 9/2016 | Baszcynski et al. |
| 2016/0289229 A1 | 10/2016 | Aktoudianakis et al. |
| 2016/0368881 A1 | 12/2016 | Bondy et al. |
| 2017/0137405 A1 | 5/2017 | Bondy et al. |
| 2018/0051005 A1 | 2/2018 | Graupe et al. |
| 2018/0194746 A1 | 7/2018 | Bondy et al. |
| 2018/0273508 A1 | 9/2018 | Brizgys et al. |
| 2018/0370950 A1 | 12/2018 | Graupe et al. |
| 2019/0083478 A1 | 3/2019 | Houston et al. |
| 2019/0084963 A1 | 3/2019 | Shi |
| 2019/0300505 A1 | 10/2019 | Allan et al. |
| 2019/0345136 A1 | 11/2019 | Brizgys et al. |
| 2019/0375726 A1 | 12/2019 | Bondy et al. |
| 2020/0038389 A1 | 2/2020 | Bauer |
| 2020/0262815 A1 | 8/2020 | Graupe et al. |
| 2020/0369647 A1 | 11/2020 | Allan et al. |
| 2021/0009555 A1 | 1/2021 | Brizgys et al. |
| 2021/0188815 A1 | 6/2021 | Bekerman et al. |

FOREIGN PATENT DOCUMENTS

| | | | |
|---|---|---|---|
| WO | WO 2003/002530 | 1/2003 | |
| WO | WO 2003/002553 | 1/2003 | |
| WO | WO 2004/050643 | 6/2004 | |
| WO | WO 2004/071448 | 8/2004 | |
| WO | WO 2004/096286 | 11/2004 | |
| WO | WO 2005/087725 | 9/2005 | |
| WO | WO 2005/123680 | 12/2005 | |
| WO | WO 2006/015261 | 2/2006 | |
| WO | WO 2006/110157 | 10/2006 | |
| WO | WO 2007/070826 | 8/2007 | |
| WO | WO 2008/013622 | 1/2008 | |
| WO | WO 2009/005677 | 1/2009 | |
| WO | WO 2009/010804 | 1/2009 | |
| WO | WO 2009/062285 | 5/2009 | |
| WO | WO 2009/114677 | 9/2009 | |
| WO | WO 2010/130034 | 11/2010 | |
| WO | WO 2011/059887 | 5/2011 | |
| WO | WO 2011/143772 | 11/2011 | |
| WO | WO 2012/003497 | 1/2012 | |
| WO | WO 2012/003498 | 1/2012 | |
| WO | WO 2012/065062 | 5/2012 | |
| WO | WO 2012/145728 | 10/2012 | |
| WO | WO 2013/006738 | 1/2013 | |
| WO | WO 2013/006792 | 1/2013 | |
| WO | WO-2013006738 A1 * | 1/2013 | ........... C07D 487/04 |
| WO | WO 2013/091096 | 6/2013 | |
| WO | WO 2013/159064 | 10/2013 | |
| WO | WO 2014/016358 | 1/2014 | |
| WO | WO 2014/023813 | 2/2014 | |
| WO | WO 2014/028931 | 2/2014 | |
| WO | WO 2014/056953 | 4/2014 | |
| WO | WO 2014/076221 | 5/2014 | |
| WO | WO 2014/100323 | 6/2014 | |
| WO | WO 2014/110297 | 7/2014 | |
| WO | WO 2014/110298 | 7/2014 | |
| WO | WO 2014/110323 | 7/2014 | |
| WO | WO 2014/128189 | 8/2014 | |
| WO | WO 2014/134566 | 9/2014 | |
| WO | WO 2015/008097 | 1/2015 | |
| WO | WO 2015/061518 | 4/2015 | |
| WO | WO 2015/130966 | 9/2015 | |
| WO | WO 2016/033243 | 3/2016 | |
| WO | WO 2016/040084 | 3/2016 | |
| WO | WO 2016/172424 | 10/2016 | |
| WO | WO 2016/172425 | 10/2016 | |
| WO | WO 2017/007689 | 1/2017 | |
| WO | WO 2018/035359 | 2/2018 | |
| WO | WO 2018/145021 | 8/2018 | |
| WO | WO 2018/203235 | 11/2018 | |
| WO | WO 2019/035904 | 2/2019 | |
| WO | WO 2019/035973 | 2/2019 | |

OTHER PUBLICATIONS

AU Examination Report dated May 3, 2016 for Australian Patent Application No. 2012278976, 3 pages.
AU Office Action dated Dec. 1, 2015 for Australian Patent Application No. 2014223973, 3 pages.
AU Office Action dated Nov. 8, 2015 for Australian Application No. 2014205317, 3 pages.
AU Office Action in Australian Appln. No. 2017213517, dated Jul. 17, 2018, 3 pages.
AU Office Action in Australian Appln. No. 2018317304, dated Apr. 6, 2020, 2 pages.
Benzaria, S. et al. (1996). "Synthesis, In Vitro Antiviral Evaluation, and Stability Studies of Bis(S-Acyl-2-Thioethyl) Ester Derivatives of 9-[2-(Phosphonomethoxy)Ethyl]adenine (PMEA) as Potential PMEA Prodrugs with Improved Oral Bioavailability," J. Med. Chem. 39(25) :4958-4965.
Berge, S. M. et al. (1977) "Pharmaceutical Salts," J. Pharma. Sci., 66(1): 1-19.
Bhattacharya, A. et al. (2014) Structural Basis of HIV-1 Capsid Recognition by PF74 and CPSF6, PNAS; 111 (52):18625-18630.
Blair, W.S. et al. (2010) "HIV Capsid is a Tractable Target for Small Molecule Therapeutic Intervention," PLoS Pathog. 6(12): e1001220, 10 pages.
BO Technical Report in Bolivian Appln. No. SNP/2018-04184, dated Jun. 6, 2018, 17 pages (with English translation).
Briggs, J. A. G. et al. (2003) "Structural Organization of Authentic, Mature HIV-1 Virions and Cores," The EMBO Journal; 22 (7): 1707-1715.
Brown, M.K. et al. (2005) "Highly Enantioselective Cu-Catalyzed Conjugate Additions of Dialkylzinc Reagents to Unsaturated Furanones and Pyranones: Preparation of Air-Stable and Catalytically Active Cu-Peptide," Angew Chem. Int. Ed. Engl. 44(33):5306-5310.
Bundgaard, H. (1991). "Design and Application of Prodrugs," Chapter 5 in A Textbook of Drug Design and Development, Krogsgaard-Larsen, P. et al. eds., Harwood Academic Publishers, Chur, Switzerland, pp. 113-191.
CA Office Action dated May 6, 2016 for Canadian Application No. 2,896,244, 4 pages.
CA Office Action in Canadian Appln. No. 2,840,095, dated May 3, 2018, 4 pages.
Campbell, E. M. et al., (2015) "HIV-1 Capsid: The Multifaceted Key Player in HIV-1 Infection," Nat Rev Microbial.; 13(8): 471-483.
Carnes, S. K. et al., (2018) "Inhibitors of the HIV-1 Capsid, A Target of Opportunity," Curr. Opin. HIV AIDS, 13(4):359-365.
Chin, C. R. et al. (2015) "Direct Visualization of HIV-1 Replication Intermediates Shows That Capsid and CPSF6 Modulate HIV-1 Intra-Nuclear Invasion and Integration", Cell Reports 13:1717-1731.
CL—English language translation of Office Action dated Mar. 30, 2017 for Chile Application No. 2445-2015, 11 pages.
CL—English language translation of Pre-grant opposition dated Jun. 15, 2016 for Chilean Application No. 2445-2015, 4 pages.

(56) References Cited

OTHER PUBLICATIONS

CL Office Action dated Mar. 30, 2017 for Chile Application No. 2445-2015, 3 pages (with English translation).
CL Office Action issued in Chilean Patent Application No. 2015-002445, dated Dec. 20, 2017, 16 pages (with English translation).
CN—English language translation of Office Action dated Jan. 16, 2017 for Chinese Application No. 201480020587.0, 16 pages (with English translation).
CN English language translation of Search Report dated Jan. 6, 2017 for Chinese Application No. 201480020587.0, 2 pages.
CN Office Action dated Jul. 19, 2017 for Chinese Application No. 2014800205870, 9 pages (with English translation).
CN Search Report dated Jan. 6, 2017 for Chinese Application No. 201480020587.0, 2 pages.
CO Office Action dated Dec. 7, 2015 for Colombian Patent Application No. 15199357 with English translation, 6 pages.
CO Office Action dated Sep. 8, 2016 English Translation for Colombia Application No. 15199357, 7 pages.
Cos, P. et al. (1998) "Structure-Activity Relationship and Classification of Flavonoids as Inhibitors of Xanthine Oxidase and Su peroxide Scavengers," J. Nat. Prod. 61:71-76.
Cossy, J. et al. (1995). "Ring Opening of Cyclopropylketones Induced by Photochemical Electron Transfer," Tetrahedron 51 (43):11751-11764.
Curreli et al. (2011) "Virtual Screening Based Identification of Novel Small-molecule Inhibitors Targeted to the HIV-1 Capsid," Bioorganic & Medicinal Chemistry 19:77-90.
De Lombaert, S. et al. (1994). "N-Phosphonomethyl Dipeptides and Their Phosphonate Prodrugs, A New Generation of Neutral Endopeptidase (NEP, EC 3.4.24.11) Inhibitors," J. Med. Chem. 37(4):498-511.
EA Office Action dated Jun. 28, 2016 for Eurasian Patent Application No. 201591457/28, 9 pages (with English translation).
EA Office Action dated Aug. 17, 2016 for Eurasian Patent Application No. 201591457/28, 16 pages(with English translation).
EA Office Action dated Jan. 18, 2017 for Eurasian Patent Application No. 201591457/28, 9 pages (with English translation).
EA Office Action issued in Eurasian Patent Application No. 201591457/28, dated Nov. 14, 2017, 12 pages (English Translation).
EP Communication in European Appln. No. 17758388, dated May 15, 2018, 5 pages.
EP Extended European Search Report in European Appln. No. 18181536.6, dated Aug. 21, 2018, 8 pages.
EP Office Action dated Dec. 4, 2015 for EP 14712844.1-1462, 2 pages.
EP Office Action dated Mar. 29, 2017 for European Patent Application No. 14712844.1-1462, 4 pages.
Fader, L. D. et al., (2013) Optimization of a 1,5 dihydrobenzo[b][1,4]diazepine-2,4-dione Series of HIV Capsid Assembly Inhibitors 2: Structure-Activity Relationships (SAR) of the C3-Phenyl Moiety, Bioorganic & Medicinal Chemistiy Letters, 23(11):3401-3405.
Farquhar, D. et al. (1983). "Biologically Reversible Phosphate-Protective Groups," J. Pharm. Sci. 72(3):324-325.
Fields, G. B. (1994) "Methods for Removing the Fmoc Group," Methods in Molecular Biology, 35: 17-27.
Forshey, B. M. et al., (2002) "Formation of a Human Immunodeficiency Virus Type 1 Core of Optimal Stability Is Crucial for Viral Replication," J. Virology, 76(11): 5667-5677.
Foster, A. B. (1984) "Deuterium Isotope Effects in Studies of Drug Metabolism," Trends Pharmacol. Sci., 5(12):524-527.
Ganser, B. K. et al. (1999) "Assembly and Analysis of Conical Models for the HIV-1 Core," Science 283: 80-82.
Ganser-Pornillos, B. K. et al., (2007) "Structure of Full-Length HIV-1 CA: A Model for the Mature Capsid Lattice," Cell; 131(1):70-9.
GC Examination Report in Gulf Cooperation Council Appln. No. GC2014-26552, dated Mar. 25, 2018.
GC Office Action dated Apr. 12, 2017 for Gulf Cooperation Council Application No. 2014/26552, 6 pages.
GC Second Examination Report issued in GCC Patent Application No. 2014/26552, dated Oct. 17, 2017, 6 pages.
Hagmann, W. K. (2008) "The many roles for fluorine in medicinal chemistry," J. Med. Chem., 51(15):4359-4369.
Hammer, S. et al. (2008). "Antiretroviral Treatment of Adult HIV Infection. 2008 Recommendations of the International AIDS Society: USA Panel," JAMA 300(5):555-570.
Hanack, M. et al., (1964) "cis-und trans bicyclo [3.1.0] hexano-(2)," Chemische Berichte, 97(6):1669-1672, XP055573746 (with English translation).
Hodgson, D.M. et al. (2007) "Intramolecular Cyclopropanation of Unsaturated Terminal Epoxides and Chlorohydrins," J. Am. Chem. Soc. 129(14):4456-4462.
Hodgson, D.M. et al. (2004). "Intramolecular Cyclopropanation of Unsaturated Terminal Epoxides," J. Am. Chem. Soc. 126(28):8664-8665.
Hung, M. et al. (2013) "Large-Scale Functional Purification of Recombinant HIV-1 Capsid" PLOS One, vol. 8, Issue 3, e58035, 11 pages.
ID Substantive Examination Report Stage 1 in Indonesian Appln. No. P-00201505361, dated Apr. 12, 2018, 8 pages.
IL Office Action issued in Israeli Patent Application No. 240519, dated Dec. 20, 2017, 5 pages.
IN Office Action in Indian Application No. 7440/DELNP/2015, dated Apr. 27, 2018, 7 pages.
Ishiyama, T. et al., (1995) "Palladium(0)-Catalyzed Cross-Coupling Reaction of Alkoxydiboron with Haloarenes: A Direct Procedure for Arylboronic Esters," J. Org, Chem., 60(23):7508-7510.
Jeong, .J.U. (2010) "Synthesis of Tetrasubstituted Pyrazones and Pyrazone N-Oxides," Tetrahedron Letters 51 (6):974-976.
Jin, Y. et al., (2010) "SAR and Molecular Mechanism Study of Novel Acylhydrazone Compounds Targeting HIV-1 CA," Bioorganic & Medicinal Chemistry; 18: 2135-2140.
Jouvenet, N. et al., (2006) "Plasma Membrane Is the Site of Productive HIV-1 Particle Assembly," PLoS Biol.;4(12):e435, 15 pages.
JP Office Action dated Feb. 9, 2016 for Japanese Patent Appl. No. 2014-519308, 6 pages.
JP Office Action dated Jan. 7, 2016 for Japanese Application No. 2015-551874—English translation, 2 pages.
JP Office Action for Japanese Application No. 2014-519308 dated Mar. 10, 2017, 9 pages (with English translation).
JP Office Action issued in Japanese Application No. 2015-560381, dated Jan. 18, 2018, 12 pages (with English translation).
Kashima, C. et al. (1991). "New Peptide Synthesis Using the Ozonolysate of 2-(1-Phthalimido)alkyl-5-Phenyloxazoles," J. Heterocyclic Chem. 28: 1241-1244.
Kelly, B. N.et al., (2007) "Structure of the Antiviral Assembly Inhibitor CAP-1 Bound to the HIV-1 CA Protein," Journal of Molecular Biology, 373(2):355-366.
Khamnei, S. et al. (1996). "Neighboring Group Catalysis in the Design of Nucleotide Prodrugs," J. Med. Chem. 39(20):4109-4115.
Kim, S. H. et al., (2013) "Discovery of a New HIV-1 Inhibitor Scaffold and Synthesis of Potential Prodrugs of Indazoles," Bioorganic & Medicinal Chemistry Letters, 23(10): 2888-2892.
Kocienski, P.J. (May 1994). "Carbonyl Protecting Groups," Chapter 5 in Protecting Groups, Thieme Publishing Group: New York, NY, pp. 155-184.
Kocienski, P.J. (May 1994). "Carboxyl Protecting Groups," Chapter 4 in Protecting Groups, Thieme Publishing Group: New York, NY, pp. 118-154.
Kocienski, P.J. (May 1994). "Diol Protecting Groups," Chapter 3 in Protecting Groups, Thieme Publishing Group: New York, NY, pp. 95-117.
Kocienski, P.J. (May 1994). "Hydroxyl Protecting Groups," Chapter 2 in Protecting Groups, Thieme Publishing Group: New York, NY, pp. 21-94.
Kocienski, P.J. (May 1994). "Protecting Groups: An Overview," Chapter 1 in Protecting Groups, Thieme Publishing Group: New York, NY, pp. 1-20.
Lad, L. et al., (2015) "Functional Label-Free Assays for Characterizing the in Vitro Mechanism of Action of Small Molecule Modulators of Capsid Assembly" Biochemistiy, 54(13), 2240-2248.

(56) References Cited

OTHER PUBLICATIONS

Lamorte, L. et al. (2015) "Discovery of Novel Small-Molecule HIV-1 Replication Inhibitors That Stabilize Capsid Complexes" Antimicrobial Agents and Chemotherapy, 57(10): 4622-4631.

Lazerwith et al., (2017) "New Antiretrovirals for HIV and Antivirals for HBV," in Comprehensive Medicinal Chemistiy, 3rd Edition, 1-36.

Lee, K. et al., (2010) "Flexible Use of Nuclear Import Pathways by HIV-1," Cell Host & Microbe; 7(3): 221-233.

Lemke, C.T. et al. (2012). "Distinct Effects of Two HIV-1 Capsid Assembly Inhibitor Families That Bind the Same Site Within the N-Terminal Domain of the Viral CA Protein," J. Viral. 86(12):6643-6655.

Macmillan, D. S. et al., (2013) "Evaluation of alternative solvent in common amide coupling reactions: replacement of dicloromethane and N,N-dimethlformamide," Green Chem, 15: 596-600.

Matreyek, K. A. et al., (2013) "Nucleoporin NUP153 Phenylalanine-Glycine Motifs Engage a Common Binding Pocket within the HIV-1 Capsid Protein to Mediate Lentiviral lnfectivity" PLOS Pathogens 9(10): e1003693, 21 pages.

Mitchell, A.G. et al. (1992). "Bioreversible Protection for the Phospho Group: Bioactivation of the Di(4-Acyloxybenzyl) and Mono(4-acyloxybenzyl) Phosphoesters of Methylphosphonate and Phosphonoacetate," J. Chem. Soc. Perkin Trans. 1: 2345-2353.

Miyaura, N. and Suzuki, A. (1995) "Palladium-Catalyzed Cross-Coupling Reactions of Oganoboron Compounds," Chem Rev, 95:2457-2483.

Montalbetti, C. A. G. N. and Falque, V. (2005) "Amide bond formation and peptide coupling," Tetrahedon, 61:10827-10852.

Nicolaou, K. C. et al. (2005) "Palladium-Catalyzed Cross-Coupling Reactions in Total Synthesis," Angew Chem Int, 44:4442-4489.

NZ First Examination Report dated Nov. 2, 2015 for New Zealand Patent Application No. 631754, 2 pages.

NZ Office Action dated Feb. 22, 2017 for New Zealand Application No. 728537, 2 pages.

Ovais, S. et al. (2013) "Synthesis, antiproliferative and anti-inflammatory activities of some novel 6-aryl-2-(p-(methanesulfonyl)phenyl)-4,5-dihydropyridazi-3(2H)-ones," European Journal of Medicinal Chemistry, 67:352-358.

Owen, A. et al. (2016) "Strengths, weaknesses, opportunities and challenges for long acting injectable therapies: Insights for applications in HIV therapy," Advances Drug Delivery Reviews 103:144-156.

PA Office Action dated Jan. 18, 2017 for Panama Application No. 90820-01, 4 pages (with English translation).

PA Office Action dated Mar. 28, 2017 for Panama Application No. 90820-01, 6 pages (with English translation).

Palella, F. J. et al. (1998) "Declining morbidity and mortality among patients with advanced human immunodeficiency virus infection," N Engl. J Med., 338:853-860.

Patel, H. R. et al., (2009) "Poloxamers: a pharmaceutical excipients with therapeutic behaviors," International Journal of PharmTech Research, 1(2):299-303.

PCT International Search Report and Written Opinion in International Appln. No. PCT/US2015/047040, dated Oct. 12, 2015 for 8 pages.

PCT International Preliminary Report on Patentability in International Appln. No. PCT/US2015/017820, dated Sep. 6, 2016, 7 pages.

PCT International Preliminary Report on Patentability in International Appln. No. PCT/US2015/047040, dated Feb. 28, 2017, 6 pages.

PCT International Search Report and Written Opinion in International Appln. No. PCT/US2012/045630, dated Sep. 19, 2012, 15 pages.

PCT International Search Report and Written Opinion in International Appln. No. PCT/US2014/010937, dated Apr. 11, 2014, 9 pages.

PCT International Search Report and Written Opinion in International Appln. No. PCT/US2014/010938, dated Mar. 11, 2014, 8 pages.

PCT International Search Report and Written Opinion in International Appln. No. PCT/US2014/019663, dated Oct. 15, 2014.

PCT International Search Report and Written Opinion in International Appln. No. PCT/US2015/017820, dated May 13, 2015, 10 pages.

PCT International Search Report and Written Opinion in International Appln. No. PCT/US2017/047416, dated Oct. 27, 2017, 10 pages.

PCT International Search Report and Written Opinion in International Appln. No. PCT/US2018/000172, dated Oct. 30, 2018, 15 pages.

PCT International Search Report and Written Opinion in International Appln. No. PCT/US2018/000248, dated Oct. 30, 2018, 15 pages.

PCT International Search Report and Written Opinion in International Appln. No. PCT/US2014/010939, dated Mar. 21, 2014.

PH Sustentative Examination Report in Philippines Appln. No. 1/2015/501881, dated May 8, 2018, 3 pages.

Pornillos, O. et al., (2009) "X-ray Structures of the Hexameric Building Block of the HIV Capsid" Cell 137(7): 1282-92.

Pornillos, O. et al., (2009) Supplemental Data for "X-ray Structures of the Hexameric Building Block of the HIV Capsid" Cell. 137(7):1282-92.

Powers, J. J. et al. (2009) "Synthesis of Methyl-, Fluoro-, and Chloro-substituted 6-Hydroxyisoindolin-1-1-Ones" Tetrahedron Letters 50(12):1267-1269.

Price, A. J. et al. (2012) "CPSF6 Defines a Conserved Capsid Interface That Modulates HIV-1 Replication" PLOS Pathogens, 8(8):e1002896, 14 pages.

Puech, F. et al. (1993). "Intracellular Delivery of Nucleoside Monophosphates Through a Reductase-Mediated Activation Process," Antiviral Res. 22(2-3):155-174.

Registry (STN) [online], Mar. 22, 2010 [date of retrieval: Nov. 12, 2018], CAS registry No. 1213065-84-9.

Registry (STN) [online], Mar. 23, 2010 [date of retrieval: Nov. 12, 2018], CAS registry No. 1213495-28-3.

Rihn, S. J. et al. (2013) "Extreme Genetic Fragility of the HIV-1 Capsid" PLOS Pathogens, 9(6): e1003461, 25 pages.

Shi, J. et al. (2011) "Small-Molecule Inhibition of Human Immunodeficiency Virus Type 1 Capsid Destabilization" Journal of Virology 85(1): 542-549.

Siddiqui, A. et al. (1999) "The Presence of Substituents on the Aryl Moiety of the Aryl Phosphoramidate Derivative of d4T Enhances Anti-HIV Efficacy in Cell Culture: A Structure-Activity Relationship" J. Med. Chem. 42:393-399.

Smith, R.J. et al. (2010) "Evolutionary Dynamics of Complex Networks of HIV Drug-Resistant Strains: The Case of San Francisco" Science 327(5966):697-701.

Sticht, J. et al. (2005) "A peptide inhibitor of HIV-1 assembly in vitro" Nature Structural & Molecular Biology, 12(8): 671-677.

STN Registry No. 137349-29-2, Nov. 15, 1991, 1 page.

SUBLOCADE Product Label, issued: Nov. 2017, 43 pages.

SV Office Action issued in Patent Application No. 2015005048, dated Sep. 26, 2017, 10 pages (with English translation).

Taiwo, B. (2009). "Understanding Transmitted HIV Resistance Through the Experience in the USA," Int. J. of Infectious Diseases 13(5):552-559.

Talele, T. T. (2016) "The 'Cyclopropyl Fragment' is a Versatile Player that Frequently Appears in Preclinical/Clinical Drug Molecules," Journal of Medicinal Chemistry, 59(19):8712-8756.

Tanaka, R. et al. (2005) "One-Pot Synthesis of Metalated Pyridines from Two Acetylenes, a Nitrile, and a Titanium(II) Alkoxide," J. Am. Chem. Soc. 127(21):7774-7780.

Tang, C. et al. (2003) "Antiviral Inhibition of the HIV-1 Capsid Protein," J. Mol. Biol., 327(5): 1013-1020.

Thenin-Houssier, S. et al. (2016) "HIV-1 capsid inhibitors as antiretroviral agents," Curr. HIV Res., 14(3):270-282.

Tse, W. C. et al. (2017) "Discovery of Novel Potent HIV Capsid Inhibitors with Long-Acting Potential," Abstract for Oral Presen-

(56) References Cited

OTHER PUBLICATIONS tation at the Conference on Retroviruses and Opportunistic Infections (CROI), Seattle, WA, 18 pages.
Tsiang, M. et al. (2012) "A Trimer of Dimers Is the Basic Building Block for Human Immunodeficiency Virus-1 Caosid Assemblv" Biochemistry, 51: 4416-4428.
TW Office Action dated Oct. 17, 2017 for Taiwan Patent Application No. 103106785, 7 pages (with English translation).
TW Office Action in Taiwanese Application No. 103106785, dated Apr. 24, 2018, 7 pages (with English translation).
UA Office Action in Ukrainian Appln. No. 2015 08564, dated Jul. 17, 2018, 6 pages (with English translation).
VN Notification No. 34475 dated Oct. 13, 2015 for Vietnam Patent Application No. 1-2015-03220, 2 pages.
Wong et al., (2014) "SPR Assay Development to Characterize Capsid Inhibitors Binding & MOA," Poster Presented at the Developments in Protein Interaction (DiPIA), La Jolla, CA, 1 page.
Wu et al., (2009) "Selective inhibitors of tumor progression loci-2(Tpl2) kinase with potent inhibition of TNF-alpha production in human whole blood," Bioorganic & Medicinal Chemistry Letters, 19(13):3485-3488.
Xianghui et al. (2003) "In Silico Virtual Screening," Biotechnology in the Post-Genome Era, 31 pages (with English translation).
Yadav, A. V. et al. (2009) "Co-crystals: a novel approach to modify physicochemical properties of active pharmaceutical ingredients" Indian J. Pharm. Sci., 71(4):359-370.
Yale, H. L. (1958) "The trifluoromethyl group in medicinal chemistry," J. Med. Chem., 1(2):121-133.
Yant, S. R. et al. (2014) "An Improved PF74 Analog Inhibits Multiple HIV Capsid Functions Independently of Host Cyclophilin A and CPSF6" Poster Presented at the Conference on Retroviruses and Opportunistic Infections (CROI), Boston, Massachusetts, 1 page.
Yant, S. R. et al. (2014) "PF74 Inhibits Multiple HIV Capsid Functions Independently of Host Cyclophilin A and CPSF6" Abstract for Poster Presented at the Conference on Retroviruses and Opportunistic Infections (CROI), Boston, Massachusetts.
Zheng, J. et al. (2018) "GS-6207: A Novel, Potent and Selective First-In-Class Inhibitor of HIV-1 Capsid Function Displays Nonclinical Pharmacokinetics Supporting Long-Acting Potential," Poster Presented at ID Week 2018, San Francisco, CA, 1 page.
Zhou, J. et al. (2015) "HIV-1 Resistance to the Capsid-Targeting Inhibitor PF74 Results in Altered Dependence on Host Factors Required for Virus Nuclear Entry" Journal of Virology, 89(17): 9068-9079.
Brittain, "Polymorphism in pharmaceutical solids," Marcel Dekker, Inc., 1999, 235-238.
Jarvis et al., "Conquering HIV's capsid", C&EN Chicago, Jul. 2017, 95(31): 23-25.
Molina et al., "On-Demand Preexposure Prophylaxis in Men at High Risk for HIV-1 Infection," N Engl. J Med. 2015, 353:2237-2246.
Indian Office Action in IN Appln. No. 202017007904, dated Sep. 22, 2020, 4 pages (with English translation).
Japanese Office Action in JP Appln. No. 2020-508446, dated Mar. 5, 2021, 5 pages (with English translation).
Korean Office Action in KR Application No. 10-2020-7007342, dated Aug. 26, 2021, 9 pages (with English translation).
Bastin et al., "Salt Selection and Optimisation Procedures for Pharmaceutical New Chemical Entities," Organic Process Research & Development, Jul. 2000, 4(5): 427-435.
Fontes Ferreira da Cunha et al., "4D-QSAR Models of HOE/BAY-793 Analogues as HIV-1 Protease Inhibitors," QSAR & Combinatorial Science, 2005, 24(2): 240-253.
Morissette et al., "High-throughput crystallization: polymorphs, salts, co-crystals and solvates of pharmaceutical solids," Advanced Drug Delivery Reviews, Feb. 2004, 56(3):275-300.
Pornillos et al., "Atomic level modeling of the HIV capsid," Nature, Jan. 2011, 469(7330):424-427.
Pungpo et al., "Computer-aided molecular design of highly potent HIV-1 RT inhibitors: 3D QSAR and molecular docking studies of efavirenz derivatives," SAR and QSAR in Environmental Research, 2006, 17(4):353-370.
Silverman, "The Organic Chemistry of Drug Design and Drug Action," Elsevier, 2004, pp. 121-169.
Silvestri et al., "Novel Indolyl Aryl Sulfones Active against HIV-1 Carrying NNRTI Resistance Mutations: Synthesis and SAR Studies," Journal of Medical Chemistry, 2003, 46(12): 2482-2493.
Yang et al., "Design, synthesis and anti-HIV-1 evaluation of hydrazide-based peptidomimetics as selective gelatinase inhibitors," Bioorganic & Medicinal Chemistry, May 2016, 24(9):2125-2136.
Indian Pre-Grant Opposition in IN Patent Application No. 202017007904, dated Sep. 14, 2021, 28 pages.

* cited by examiner

CHOLINE SALT FORMS OF AN HIV CAPSID INHIBITOR

TECHNICAL FIELD

The present disclosure relates to choline salt forms of an HIV capsid inhibitor, and pharmaceutical compositions thereof, for use in the treatment or prevention of a Retroviridae viral infection including an infection caused by the HIV virus.

BACKGROUND

Positive-single stranded RNA viruses comprising the Retroviridae family include those of the subfamily Orthoretrovirinae and genera *Alpharetrovirus, Betaretrovirus, Gammaretrovirus, Deltaretrovirus, Epsilonretrovirus, Lentivirus*, and *Spumavirus* which cause many human and animal diseases. Among the *Lentivirus*, HIV-1 infection in humans leads to depletion of T helper cells and immune dysfunction, producing immunodeficiency and vulnerability to opportunistic infections. Treating HIV-1 infections with highly active antiretroviral therapies (HAART) has proven to be effective at reducing viral load and significantly delaying disease progression (Hammer, S. M., et al.; *JAMA* 2008, 300: 555-570). However, these treatments could lead to the emergence of HIV strains that are resistant to current therapies (Taiwo, B., *International Journal of Infectious Diseases* 2009, 13:552-559; Smith, R. J., et al., *Science* 2010, 327: 697-701). Therefore, there is an ongoing need to discover new antiretroviral agents and to develop methods for their preparation and purification as well as prepare improved pharmaceutical formulations of the same. The choline salt forms of the HIV capsid inhibitor disclosed herein help meet these and other needs.

SUMMARY

The present application provides a choline salt of Compound 1:

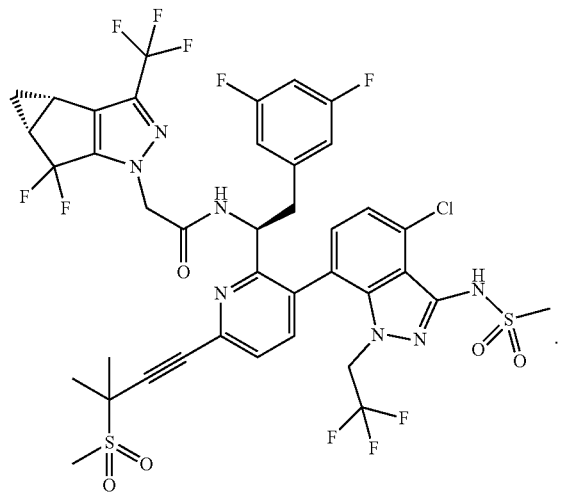

Compound 1

The present application further provides a pharmaceutical composition comprising a choline salt of Compound 1, or a crystalline form thereof disclosed herein, and at least one pharmaceutically acceptable excipient.

The present application further provides a crystalline form of the choline salt of Compound 1.

The present application further provides a method of treating or preventing a human immunodeficiency virus (HIV) infection comprising administering a therapeutically effective amount of a choline salt, or crystalline form thereof, to a subject in need thereof.

The present application further provides a choline salt of Compound 1, or crystalline form thereof, for use in therapy.

The present application further provides a choline salt of Compound 1, or crystalline form thereof, for use in a method of treating or preventing a human immunodeficiency virus (HIV) infection, comprising administering a therapeutically effective amount of the choline salt, or crystalline form, to a subject in need thereof.

The present application further provides a process of increasing the amount of an isomeric compound of Isomer A:

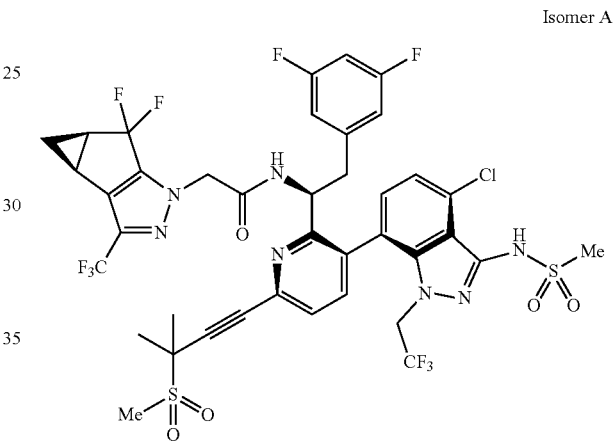

Isomer A relative to an amount of an isomeric compound of Isomer B:

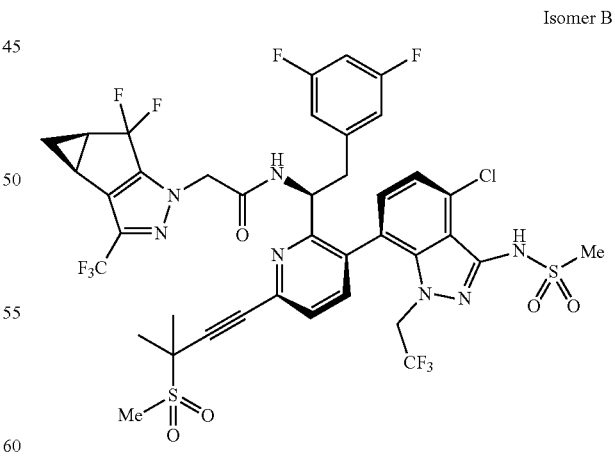

Isomer B or the amount of an isomeric compound of Isomer B relative to the amount of an isomeric compound of Isomer A, in a starting mixture comprising both isomeric compounds, the process comprising:

contacting the starting mixture with N,N,N-trimethylethanolammonium hydroxide in the presence of a solvent to form a N,N,N-trimethylethanolammonium salt mixture of both isomeric compounds, wherein the salt mixture has an increased amount of the isomeric salt of Isomer A relative to the amount of the isomeric salt of Isomer B, or an increased amount of the isomeric salt of Isomer B relative to the amount of the isomeric salt of Isomer A, when compared with the relative amounts of the isomeric compounds of Isomer A and Isomer B in the starting mixture.

DETAILED DESCRIPTION

Figure 1:
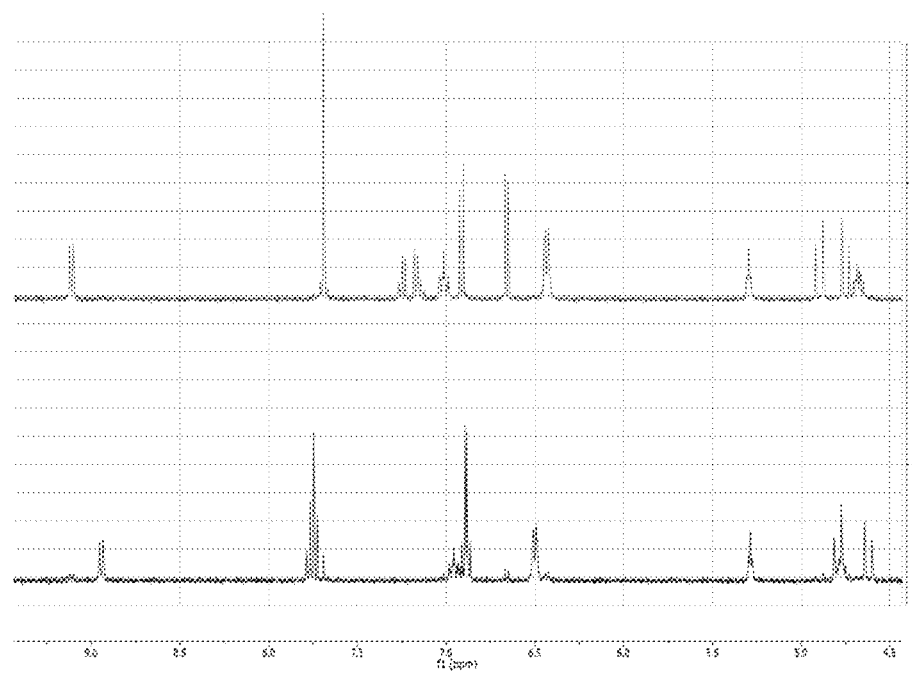
FIG. 1 shows $^1$H-NMR spectra characteristic of the N,N,N-trimethylethanolammonium (choline) salt of of Compound 1, enriched in Isomer B (top trace) and enriched in Isomer A (bottom trace).

The present invention relates to new solid forms, which are choline salts, of the HIV capsid inhibitor N—((S)-1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (i.e., Compound 1, see below). One skilled in the art understands that a compound structure may be named or identified using commonly recognized nomenclature systems and symbols. By way of example, the compound may be named or identified with common names, systematic or non-systematic names. The nomenclature systems and symbols that are commonly recognized in the art of chemistry including but not limited to Chemical Abstract Service (CAS) and International Union of Pure and Applied Chemistry (IUPAC). Accordingly, the compound structure for Compound 1 provided above may also be named or identified as N—((S)-1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-43bS,4aR)-5,5-difluoro-3-(trifluoromethyl)-3b,4,4a,5-tetrahydro-1H-cyclopropa[3,4]cyclopenta[1,2-c]pyrazol-1-yl)acetamide.

Compound 1

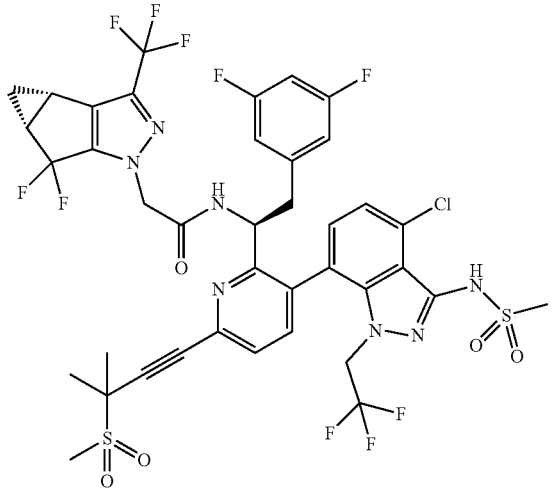

Compound 1 can be a weak acid (pKA 6.7 at sulfonamide) or a weak base (pKa<1 at pyridine) and consists of two atropisomers, Isomer A and Isomer B, that can rotate along one of the C—C bonds, as shown below. In solution, the two atropisomers coexist in the ratio of about 1:5 to 1:8 (Isomer A:Isomer B), depending on temperatures and pH. The two atropisomers can be separated by chromatography but they re-equilibrate in solution ($t_{1/2}$≈1-2 hours at 37° C. and the rotational energy barrier is about 24 kcal/mol).

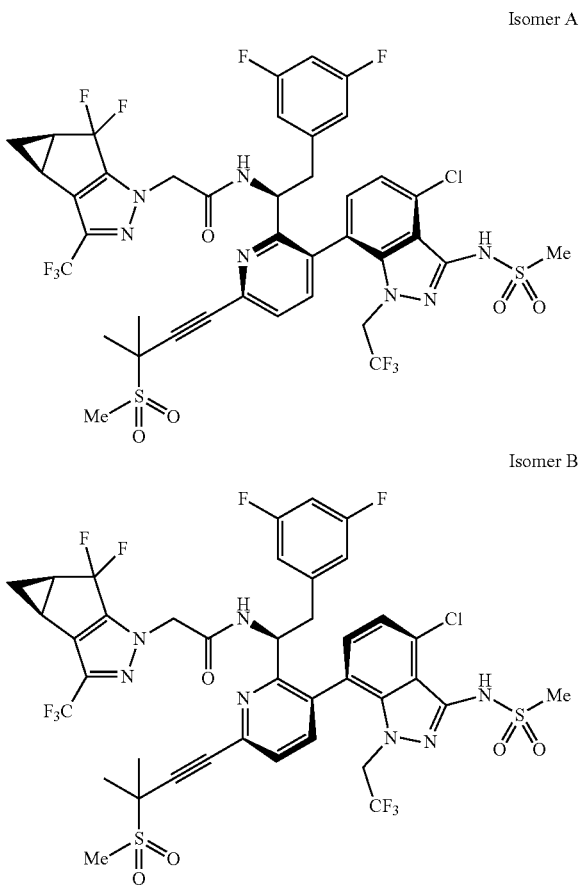

Isomer A

Isomer B

As described herein, Isomer A or Isomer B can be enriched by crystallization. For the N,N,N-trimethylethanolammonium (choline) salts described herein, either of the atropisomers can be enriched through the formation of different crystalline forms.

The solid forms of the invention include salt forms (both amorphous and crystalline) of Compound 1. As used herein, "solid form" generally refers to a solid chemical substance that can be amorphous or crystalline. In some embodiments, the solid form of the invention is a choline salt of Compound 1 which can be amorphous or crystalline. Crystalline choline salts of Compound 1 can exist in different crystalline forms (i.e., have different polymorphic or pseudopolymorphic forms).

As used herein, "crystalline form" is meant to refer to a certain lattice configuration of a crystalline substance (e.g., a salt). Different crystalline forms of the same substance typically have different crystalline lattices (e.g., unit cells) which are attributed to different physical properties that are characteristic of each of the crystalline forms. In some instances, different lattice configurations have different water or solvent content.

According to the present invention, a crystalline form of a choline salt of Compound 1 can be useful in the synthesis and/or purification of Compound 1. For example, a crystalline form of a choline salt of Compound 1 can be an intermediate in the synthesis of Compound 1. In addition, different crystalline forms of choline salts of Compound 1 may have different properties with respect to bioavailability, stability, purity, and/or manufacturability for medical or pharmaceutical uses. Variations in the crystal structure of a pharmaceutical drug substance or active ingredient may affect the dissolution rate (which may affect bioavailability, etc.), manufacturability (e.g., ease of handling, ability to consistently prepare doses of known strength), and stability (e.g., thermal stability, shelf life, etc.) of a pharmaceutical drug product or active ingredient. Such variations may affect the preparation or formulation of pharmaceutical compositions in different dosage or delivery forms, such as solutions or solid oral dosage form including tablets and capsules. Compared to other forms such as non-crystalline or amorphous forms, crystalline forms may provide desired or suitable hygroscopicity, particle size controls, dissolution rate, solubility, purity, physical and chemical stability, manufacturability, yield, and/or process control. Thus, the crystalline forms of the choline salts of of Compound 1 may provide advantages such as improving the manufacturing process of the compound, the stability or storability of a drug product form of the compound, the stability or storability of a drug substance of the compound and/or the bioavailability and/or stability of the compound as an active agent.

The use of certain solvents and/or processes have been found to produce different crystalline forms of the choline salts of Compound 1 which may exhibit one or more of the favorable characteristics described above. The processes for the preparation of the crystalline forms described herein and characterization of these crystalline forms are described in detail below.

In some embodiments, the choline salts described herein, or crystalline forms thereof, are purified or substantially isolated. By "substantially isolated" is meant that the choline salt, or crystalline form thereof is at least partially or substantially separated from the environment in which it was formed or detected. Partial separation can include, for example, a composition enriched in the choline salt, or crystalline form of the invention. Substantial separation can include compositions containing at least about 50%, at least about 60%, at least about 70%, at least about 80%, at least about 90%, at least about 95%, at least about 97%, or at least about 99% by weight of the choline salt, or crystalline form of the invention. In some embodiments, the choline salt, or crystalline form of the invention can be prepared with a purity of about 75% or more, 80% or more, 85% or more, 90% or more, 95% or more, 98% or more, or 99% or more.

The different crystalline forms can be identified by solid state characterization methods such as by X-ray powder diffraction (XRPD). Other characterization methods such as differential scanning calorimetry (DSC) further help identify the form as well as help determine stability and solvent/water content.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, various filters used, the sample mounting procedure, and the particular instrument employed. In some instances, new peaks may be observed or existing peaks may disappear, depending on the type of the instrument or the settings. As used herein, the term "peak" refers to a reflection having a relative height/intensity of at least about 5% of the maximum peak height/intensity. Moreover, instrument variation and other factors can affect the 2-theta values. Thus, peak assignments, such as those reported herein, can vary by plus or minus about 0.2° (2-theta), and the term "substantially" and "about" as used in the context of XRPD herein is meant to encompass the above-mentioned variations.

In the same way, temperature readings in connection with DSC can vary about ±3° C. depending on the instrument, particular settings, sample preparation, etc. Accordingly, a crystalline form reported herein having a DSC thermogram "substantially" as shown in any of the Figures or the term "about" is understood to accommodate such variation.

The present invention provides crystalline forms of certain compounds or salts thereof. In some embodiments, the crystalline form may be substantially anhydrous. In some embodiments, the crystalline form may be hydrated or solvated.

Compound 1 N,N,N-trimethylethanolammonium (Choline) Salt

In some embodiments, Compound 1 can be isolated as a N,N,N-trimethylethanolammonium (choline) salt which can be amorphous or crystalline. In some embodiments, the N,N,N-trimethylethanolammonium (choline) salt of Compound 1 is crystalline.

In some embodiments, the crystalline form of the N,N,N-trimethylethanolammonium salt of Compound 1 is selected from crystalline Material A, crystalline Form I, crystalline Form II, crystalline Form III, crystalline Form IV, crystalline Form V, crystalline Form VI, and crystalline Form VII.

Figure 3:
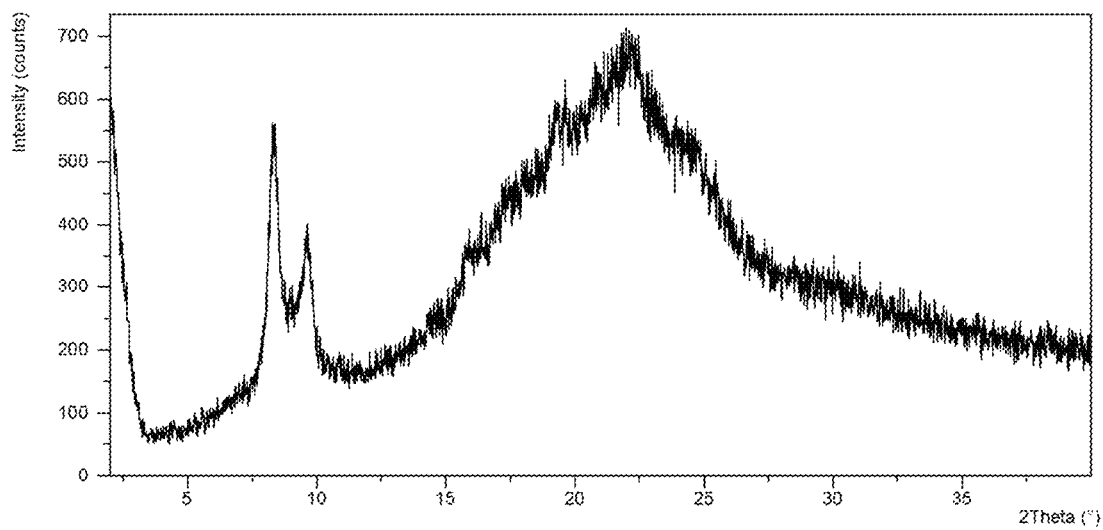
FIG. 3 shows an XRPD pattern characteristic of the N,N,N-trimethylethanolammonium (choline) salt of Compound 1, Material A.

In some embodiments, crystalline Material A of the N,N,N-trimethylethanolammonium salt of Compound 1 has an XRPD profile substantially as shown in FIG. 3.

Figure 4:
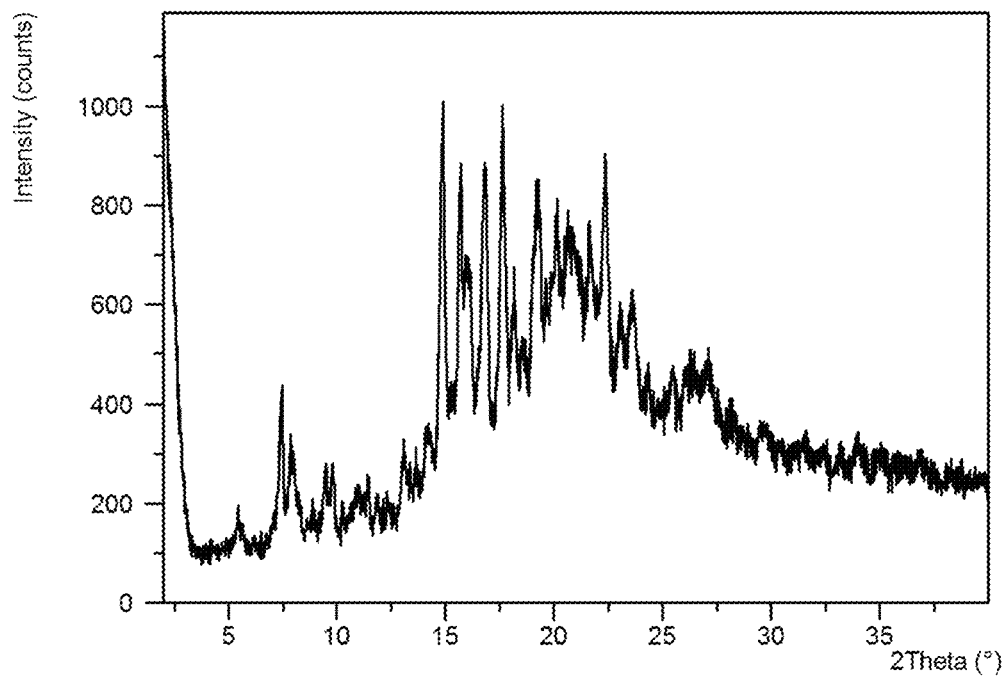
FIG. 4 shows an XRPD pattern characteristic of the N,N,N-trimethylethanolammonium (choline) salt of Compound 1, crystalline Form I.

In some embodiments, crystalline Form I of the N,N,N-trimethylethanolammonium salt of Compound 1 has an XRPD profile substantially as shown in FIG. 4.

In some embodiments, crystalline Form I of the N,N,N-trimethylethanolammonium salt of Compound 1 has at least one, at least two, at least three, at least four, at least five, at least six, at least seven, at least eight, or at least nine XRPD peaks, in terms of 2-theta±0.2°, selected from 5.5°, 7.5°, 7.9°, 14.9°, 15.7°, 16.8°, 17.6°, 19.3°, and 22.4°.

Figure 5:
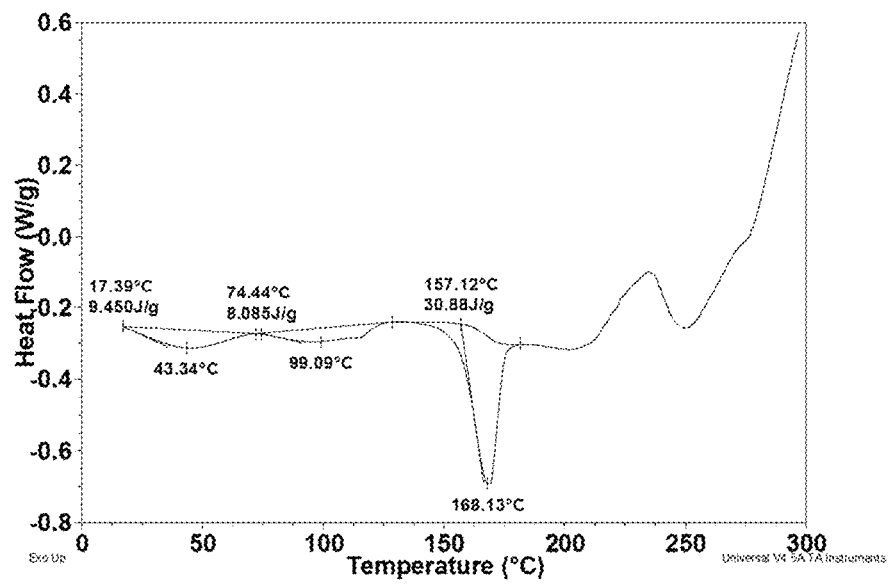
FIG. 5 shows a DSC thermogram characteristic of the N,N,N-trimethylethanolammonium (choline) salt of Compound 1, crystalline Form I.

In some embodiments, crystalline Form I of the N,N,N-trimethylethanolammonium salt of Compound 1 is characterized by a DSC thermogram substantially as shown in FIG. 5.

In some embodiments, crystalline Form I of the N,N,N-trimethylethanolammonium salt of Compound 1 is characterized by a DSC thermogram having a melting onset of about 157° C.

Figure 6:
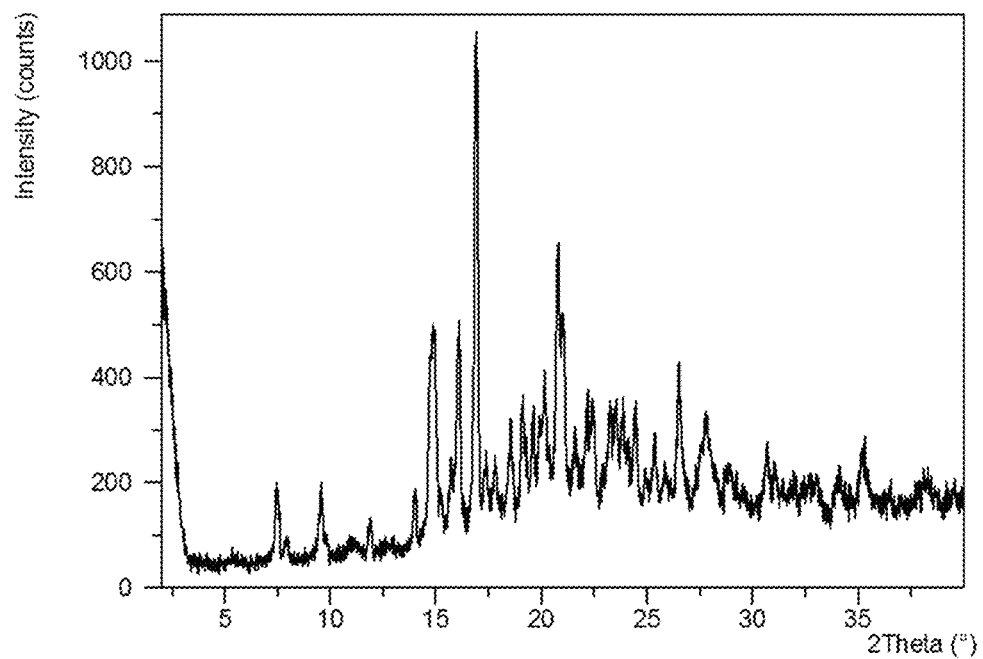
FIG. 6 shows an XRPD pattern characteristic of the N,N,N-trimethylethanolammonium (choline) salt of Compound 1, crystalline Form II.

In some embodiments, crystalline Form II of the N,N,N-trimethylethanolammonium salt of Compound 1 has an XRPD profile substantially as shown in FIG. 6.

In some embodiments, crystalline Form II of the N,N,N-trimethylethanolammonium salt of Compound 1 has at least one, at least two, at least three, at least four, at least five, at least six, at least seven, at least eight, or at least nine XRPD peaks, in terms of 2-theta±0.2°, selected from 7.5°, 9.6°, 14.0°, 14.9°, 16.1°, 16.9°, 20.8°, 21.0°, and 26.5°.

Figure 7:
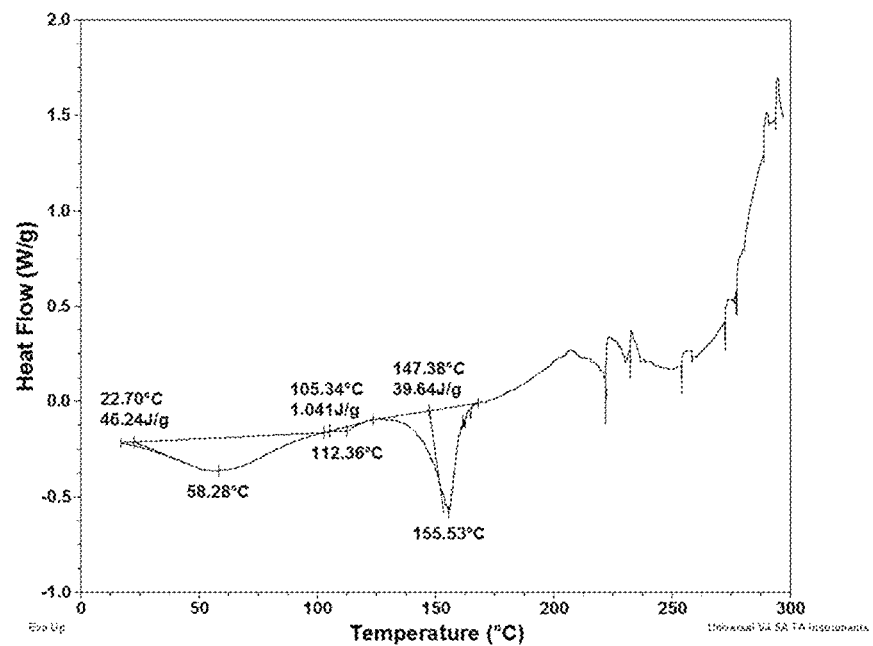
FIG. 7 shows a DSC thermogram characteristic of the N,N,N-trimethylethanolammonium (choline) salt of Compound 1, crystalline Form II.

In some embodiments, crystalline Form II of the N,N,N-trimethylethanolammonium salt of Compound 1 is characterized by a DSC thermogram substantially as shown in FIG. 7.

In some embodiments, crystalline Form II of the N,N,N-trimethylethanolammonium salt of Compound 1 is characterized by a DSC thermogram having a melting onset of about 147° C.

Figure 8:
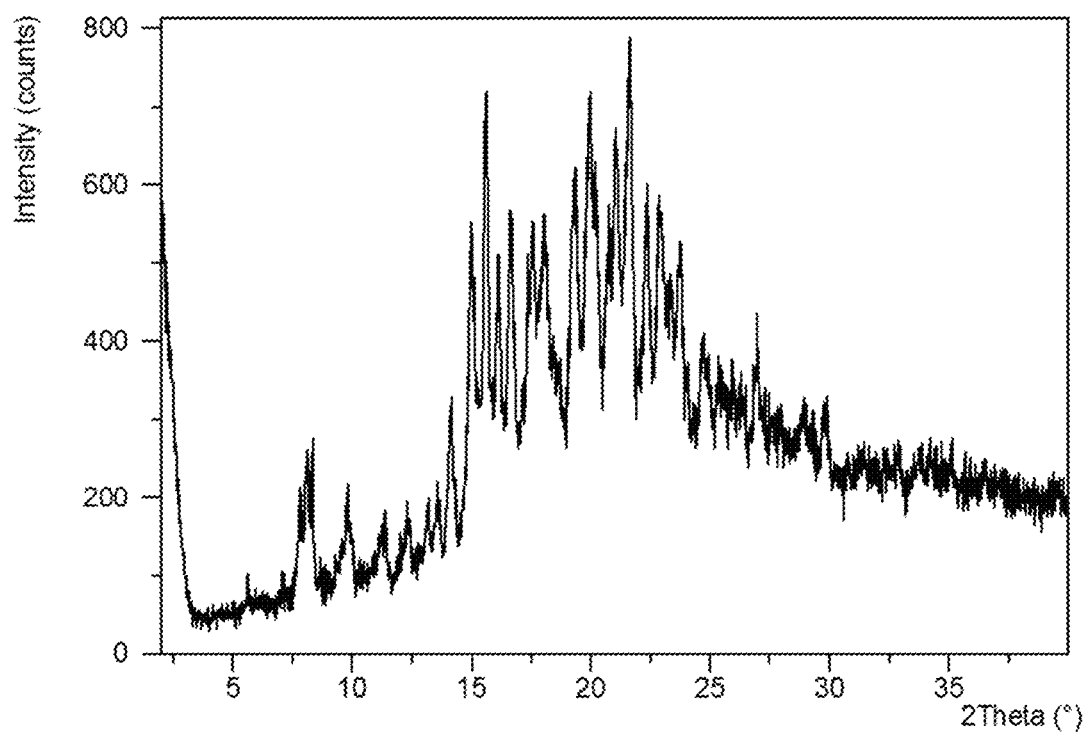
FIG. 8 shows an XRPD pattern characteristic of the N,N,N-trimethylethanolammonium (choline) salt of Compound 1, crystalline Form III.

In some embodiments, crystalline Form III of the N,N,N-trimethylethanolammonium salt of Compound 1 has an XRPD profile substantially as shown in FIG. 8.

In some embodiments, crystalline Form III of the N,N,N-trimethylethanolammonium salt of Compound 1 has at least one, at least two, at least three, at least four, at least five, at least six, at least seven, at least eight, or at least nine XRPD peaks, in terms of 2-theta±0.2°, selected from 7.8°, 8.1°, 8.3°, 15.0°, 15.7°, 16.7°, 20.0°, 21.1°, and 21.7°.

Figure 9:
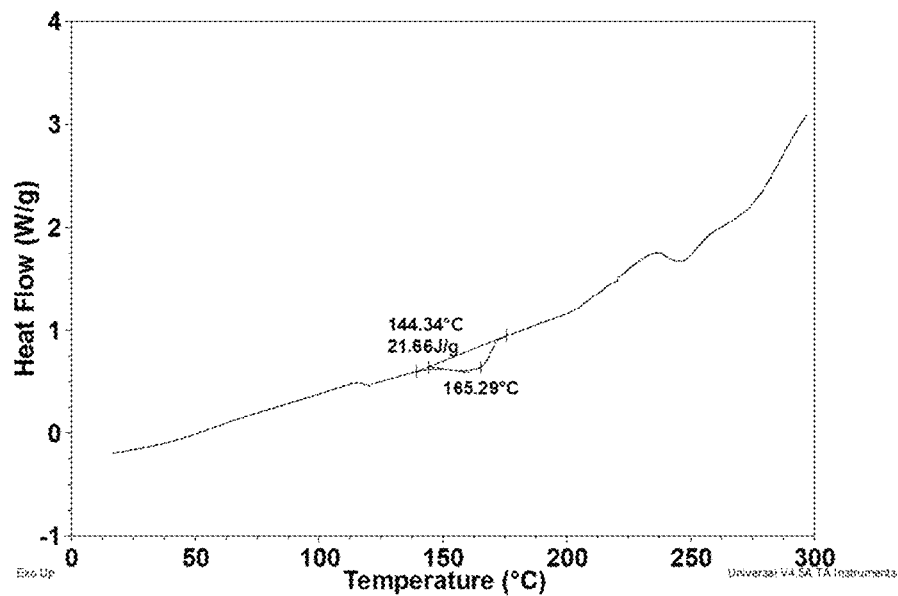
FIG. 9 shows a DSC thermogram characteristic of the N,N,N-trimethylethanolammonium (choline) salt of Compound 1, crystalline Form III.

In some embodiments, crystalline Form III of the N,N,N-trimethylethanolammonium salt of Compound 1 is characterized by a DSC thermogram substantially as shown in FIG. 9.

In some embodiments, crystalline Form III of the N,N,N-trimethylethanolammonium salt of Compound 1 is characterized by a DSC thermogram having a melting onset of about 144° C.

Figure 10:
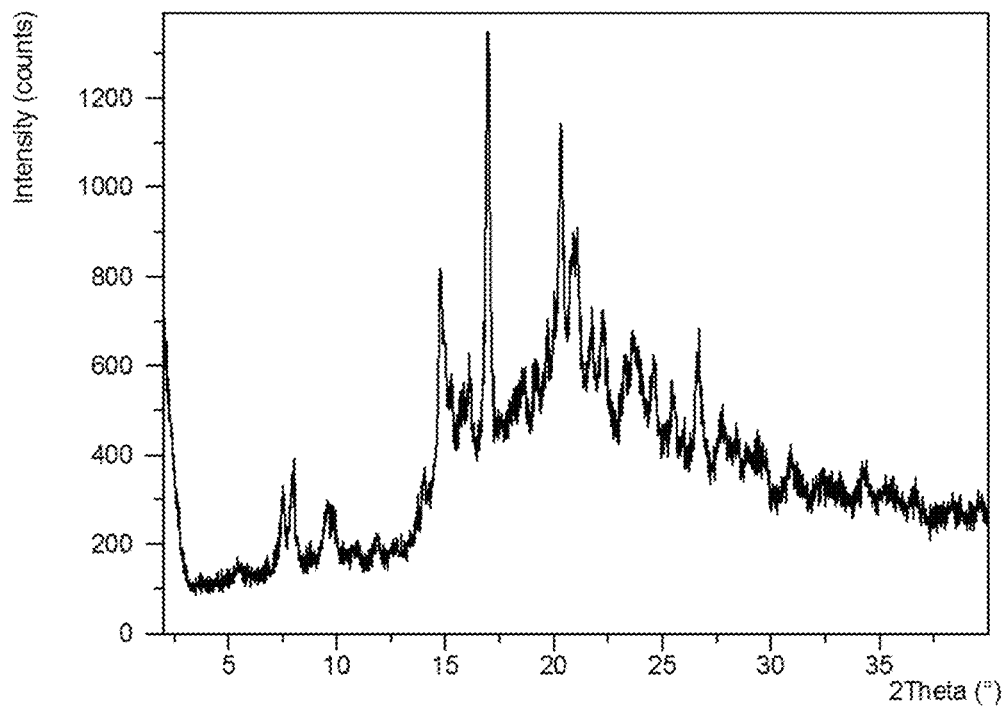
FIG. 10 shows an XRPD pattern characteristic of the N,N,N-trimethylethanolammonium (choline) salt of Compound 1, crystalline Form IV.

In some embodiments, crystalline Form IV of the N,N,N-trimethylethanolammonium salt of Compound 1 has an XRPD profile substantially as shown in FIG. 10.

In some embodiments, crystalline Form IV of the N,N,N-trimethylethanolammonium salt of Compound 1 has at least one, at least two, at least three, at least four, at least five, at least six, at least seven, at least eight, or at least nine XRPD peaks, in terms of 2-theta±0.2°, selected from 7.5°, 8.0°, 14.8°, 16.1°, 17.0°, 20.3°, 21.1°, 24.6°, and 26.7°.

Figure 11:
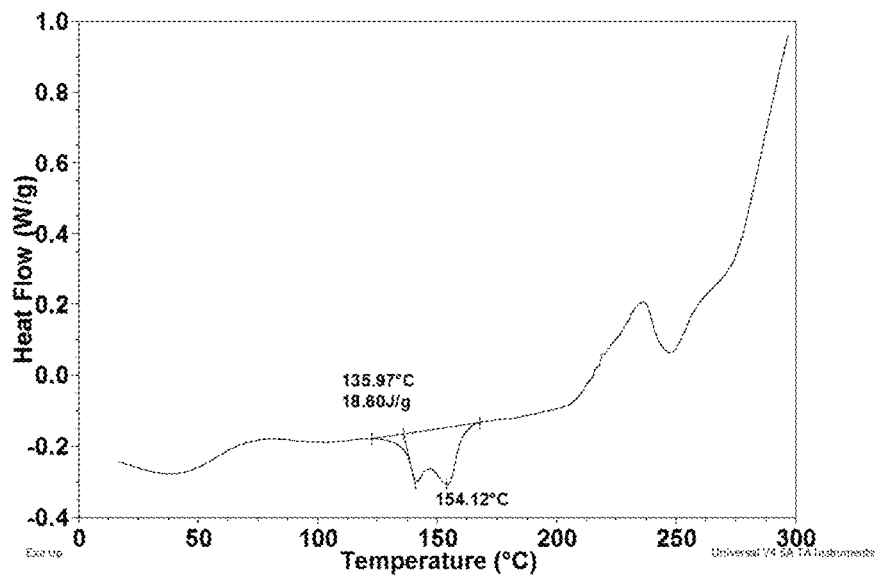
FIG. 11 shows a DSC thermogram characteristic of the N,N,N-trimethylethanolammonium (choline) salt of Compound 1, crystalline Form IV.

In some embodiments, crystalline Form IV of the N,N,N-trimethylethanolammonium salt of Compound 1 is characterized by a DSC thermogram substantially as shown in FIG. 11.

In some embodiments, crystalline Form IV of the N,N,N-trimethylethanolammonium salt of Compound 1 is characterized by a DSC thermogram having a melting onset of about 136° C.

Figure 12:
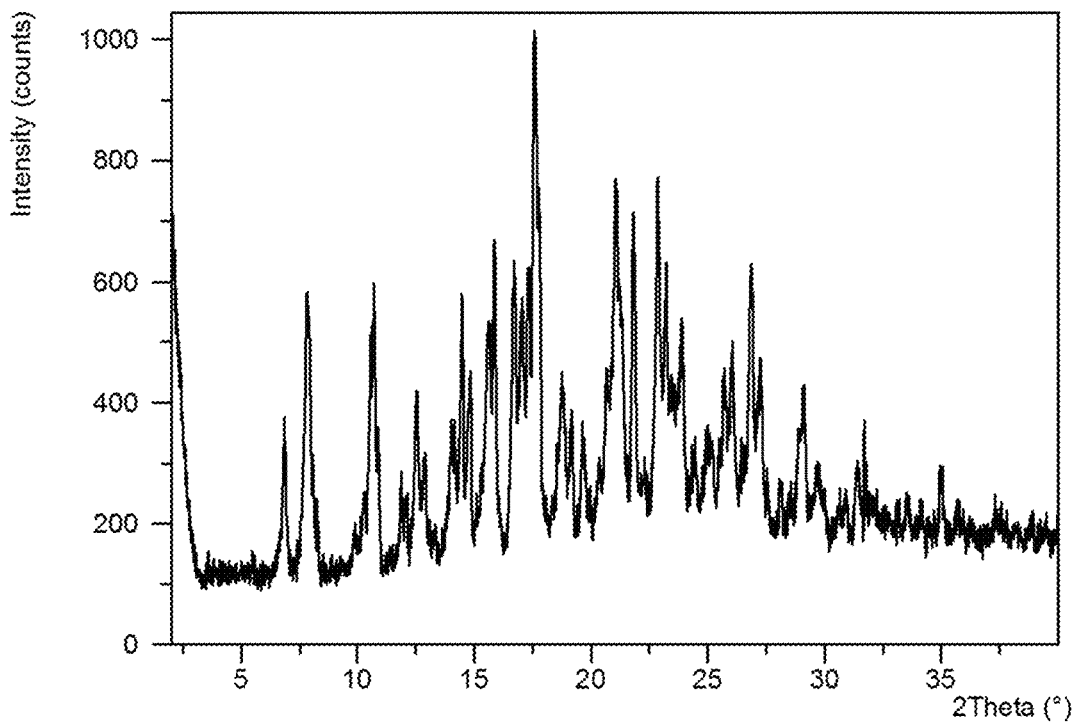
FIG. 12 shows an XRPD pattern characteristic of the N,N,N-trimethylethanolammonium (choline) salt of Compound 1, crystalline Form V.

In some embodiments, crystalline Form V of the N,N,N-trimethylethanolammonium salt of Compound 1 has an XRPD profile substantially as shown in FIG. 12.

In some embodiments, crystalline Form V of the N,N,N-trimethylethanolammonium salt of Compound 1 has at least one, at least two, at least three, at least four, at least five, at least six, at least seven, at least eight, or at least nine XRPD peaks, in terms of 2-theta±0.2°, selected from 6.9°, 7.9°, 10.7°, 16.7°, 17.6°, 21.1°, 21.8°, 22.8°, and 26.9°.

Figure 13:
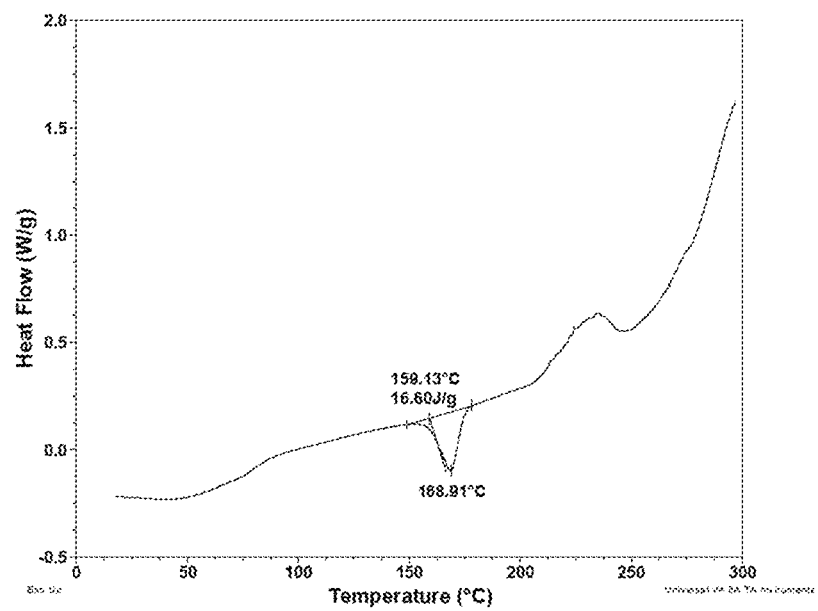
FIG. 13 shows a DSC thermogram characteristic of the N,N,N-trimethylethanolammonium (choline) salt of Compound 1, crystalline Form V.

In some embodiments, crystalline Form V of the N,N,N-trimethylethanolammonium salt of Compound 1 is characterized by a DSC thermogram substantially as shown in FIG. 13.

In some embodiments, crystalline Form V of the N,N,N-trimethylethanolammonium salt of Compound 1 is characterized by a DSC thermogram having a melting onset of about 159° C.

Figure 14:
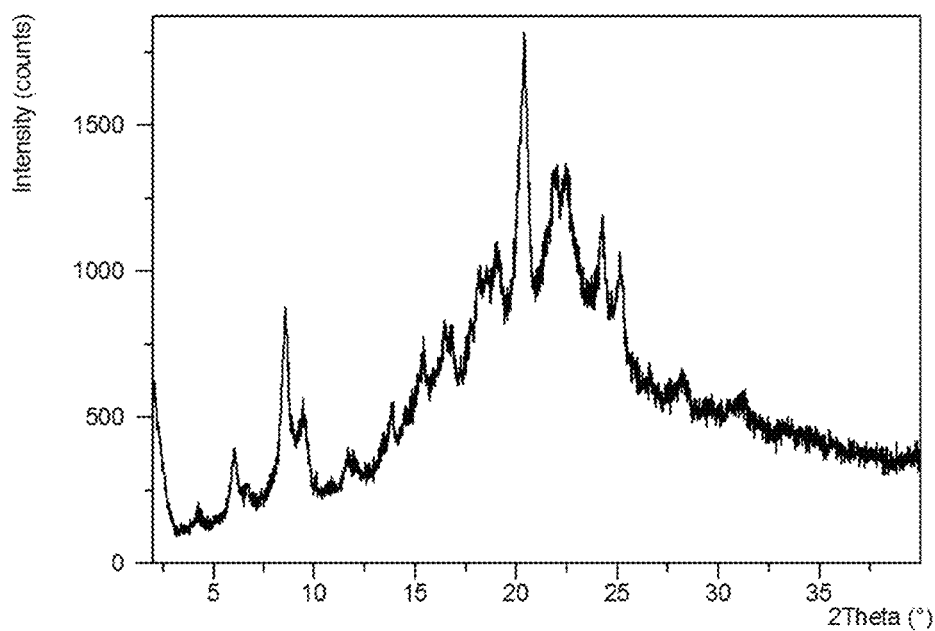
FIG. 14 shows an XRPD pattern characteristic of the N,N,N-trimethylethanolammonium (choline) salt of Compound 1, crystalline Form VI.

In some embodiments, crystalline Form VI of the N,N,N-trimethylethanolammonium salt of Compound 1 has an XRPD profile substantially as shown in FIG. 14.

In some embodiments, crystalline Form VI of the N,N,N-trimethylethanolammonium salt of Compound 1 has at least one, at least two, at least three, at least four, at least five, at least six, at least seven, at least eight, or at least nine XRPD peaks, in terms of 2-theta±0.2°, selected from 6.1°, 8.6°, 9.5°, 15.4°, 20.4°, 21.9°, 22.5°, 24.2°, and 25.2°.

Figure 15:
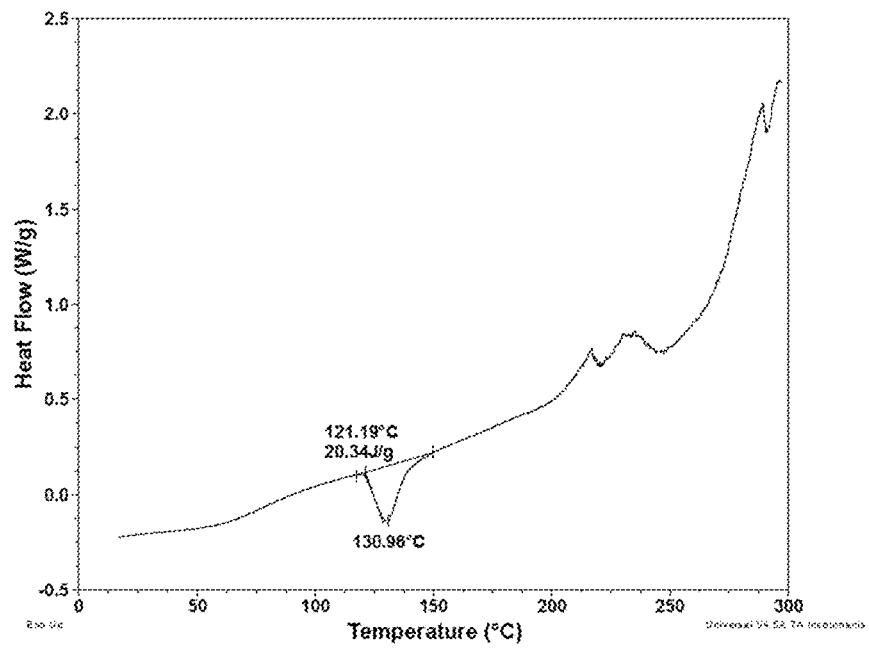
FIG. 15 shows a DSC thermogram characteristic of the N,N,N-trimethylethanolammonium (choline) salt of Compound 1, crystalline Form VI.

In some embodiments, crystalline Form VI of the N,N,N-trimethylethanolammonium salt of Compound 1 is characterized by a DSC thermogram substantially as shown in FIG. 15.

In some embodiments, crystalline Form VI of the N,N,N-trimethylethanolammonium salt of Compound 1 is characterized by a DSC thermogram having a melting onset of about 121° C.

Figure 16:
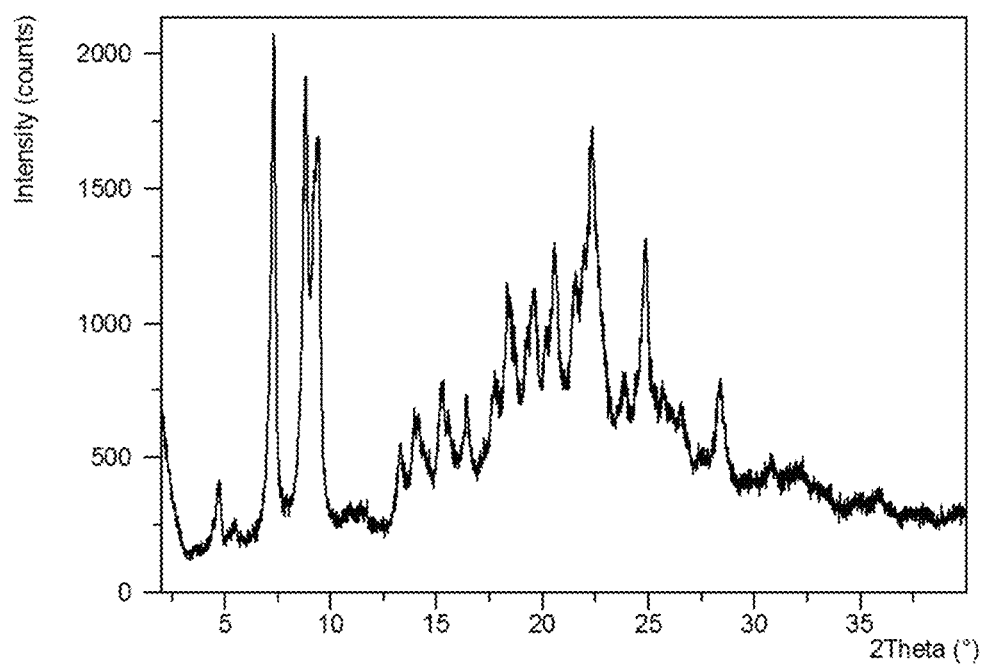
FIG. 16 shows an XRPD pattern characteristic of the N,N,N-trimethylethanolammonium (choline) salt of Compound 1, crystalline Form VII.

In some embodiments, crystalline Form VII of the N,N,N-trimethylethanolammonium salt of Compound 1 has an XRPD profile substantially as shown in FIG. 16.

In some embodiments, crystalline Form VII of the N,N,N-trimethylethanolammonium salt of Compound 1 has at least one, at least two, at least three, at least four, at least five, at least six, at least seven, at least eight, or at least nine XRPD peaks, in terms of 2-theta±0.2°, selected from 4.7°, 7.3°, 8.9°, 9.5°, 18.3°, 20.5°, 22.3°, 24.9°, and 28.4°.

Figure 17:
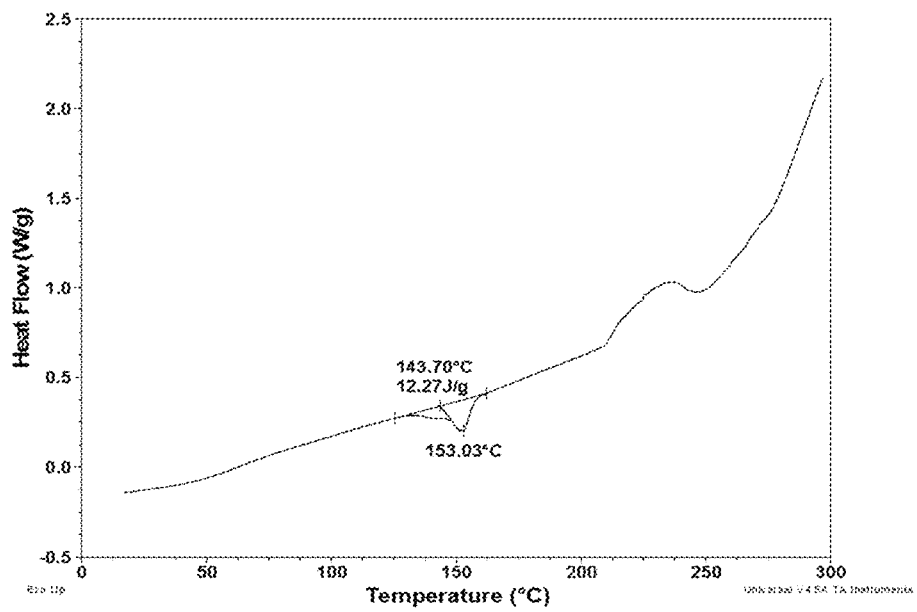
FIG. 17 shows a DSC thermogram characteristic of the N,N,N-trimethylethanolammonium (choline) salt of Compound 1, crystalline Form VII.

In some embodiments, crystalline Form VII of the N,N,N-trimethylethanolammonium salt of Compound 1 is characterized by a DSC thermogram substantially as shown in FIG. 17.

In some embodiments, crystalline Form VII of the N,N,N-trimethylethanolammonium salt of Compound 1 is characterized by a DSC thermogram having a melting onset of about 144° C.

In some embodiments, the crystalline form of the N,N,N-trimethylethanolammonium salt of Compound 1 is solvated.

In some embodiments, the crystalline form of the N,N,N-trimethylethanolammonium salt of Compound 1 is an ethanol solvate.

Figure 18:
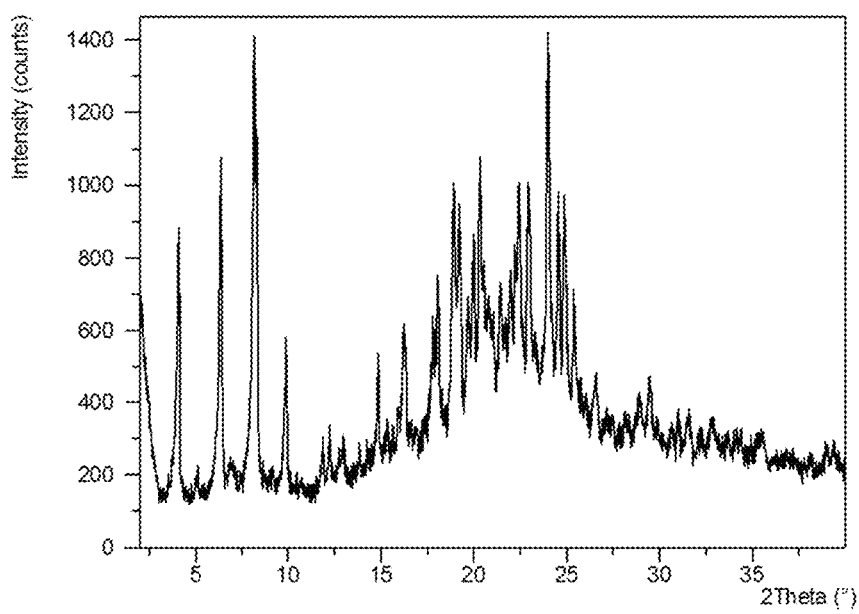
FIG. 18 shows an XRPD pattern characteristic of the ethanol solvate form of the N,N,N-trimethylethanolammonium (choline) salt of Compound 1.

In some embodiments, the crystalline form of the N,N,N-trimethylethanolammonium salt of Compound 1, ethanol solvate has an XRPD profile substantially as shown in FIG. 18.

In some embodiments, the crystalline form of the N,N,N-trimethylethanolammonium salt of Compound 1 is a tetrahydrofuran solvate.

Figure 19:
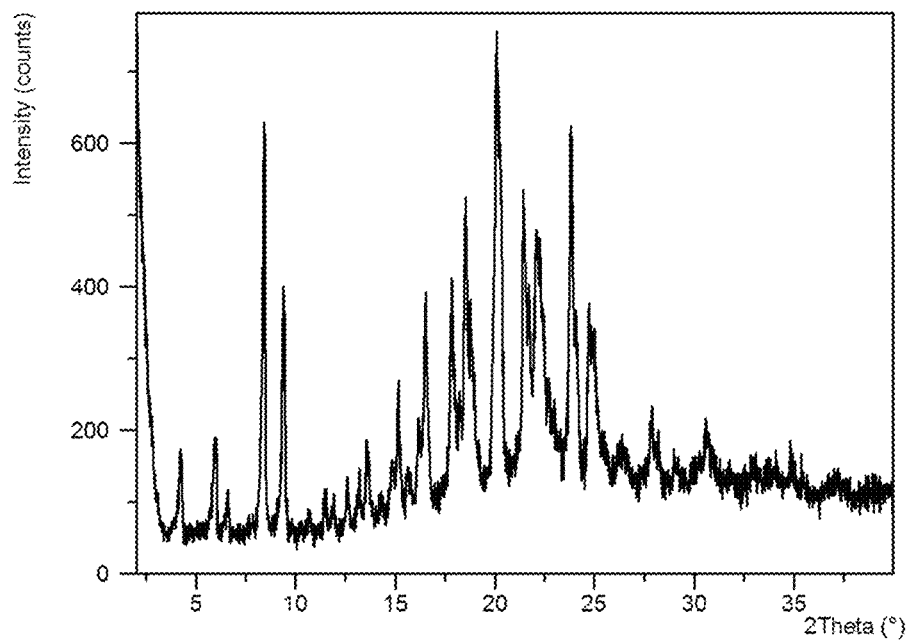
FIG. 19 shows an XRPD pattern characteristic of the tetrahydrofuran solvate form of the N,N,N-trimethylethanolammonium (choline) salt of Compound 1.

In some embodiments, the crystalline form of the N,N,N-trimethylethanolammonium salt of Compound 1, tetrahydrofuran solvate has an XRPD profile substantially as shown in FIG. 19.

In some embodiments, the crystalline form of the N,N,N-trimethylethanolammonium salt of Compound 1 is a methyl tert-butyl ether solvate.

Figure 20:
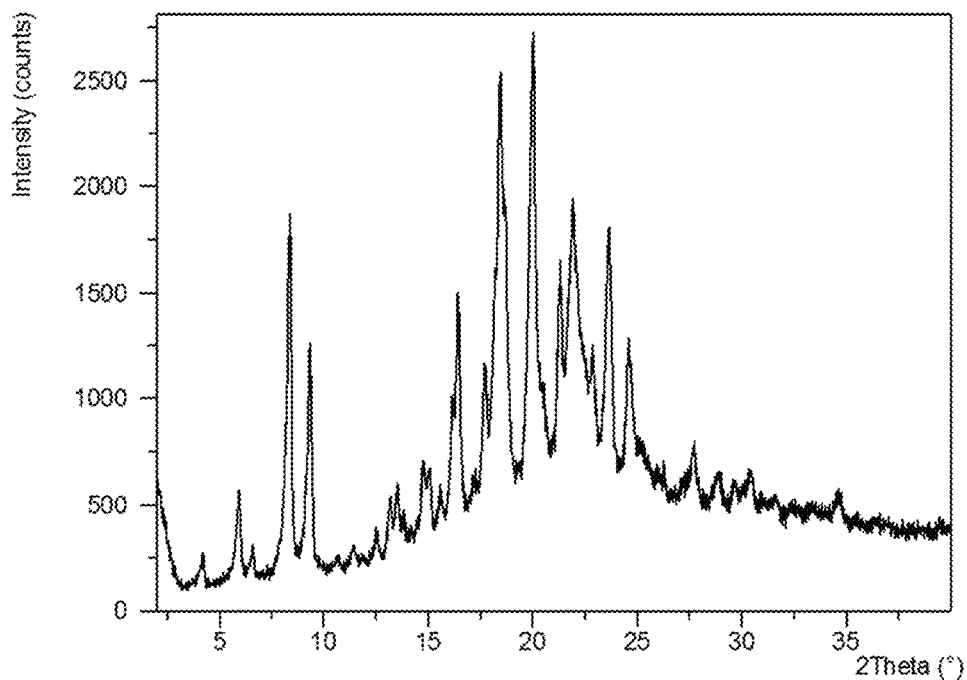
FIG. 20 shows an XRPD pattern characteristic of the methyl tert-butyl ether solvate form of the N,N,N-trimethylethanolammonium (choline) salt of Compound 1.

In some embodiments, the crystalline form of the N,N,N-trimethylethanolammonium salt of Compound 1, methyl tert-butyl ether solvate has an XRPD profile substantially as shown in FIG. 20.

The present application further provides a process of increasing the amount of an isomeric compound of Isomer A:

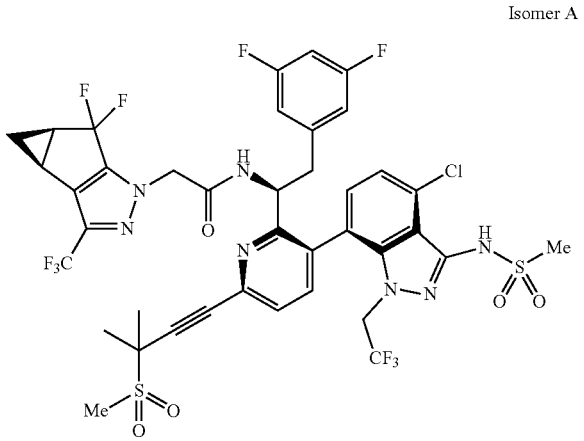

Isomer A relative to an amount of an isomeric compound of Isomer B:

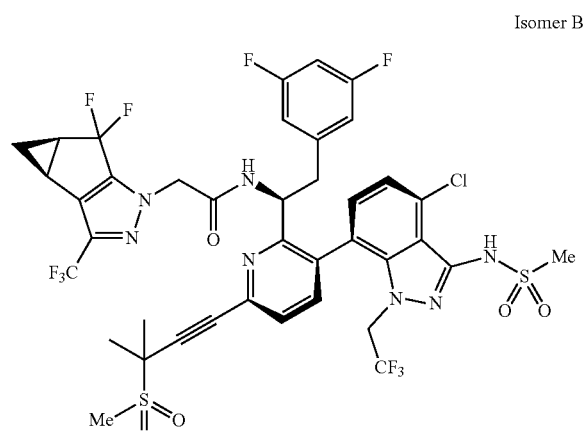

Isomer B or the amount of an isomeric compound of Isomer B relative to the amount of an isomeric compound of Isomer A, in a starting mixture comprising both isomeric compounds, the process comprising:

contacting the starting mixture with N,N,N-trimethylethanolammonium hydroxide in the presence of a solvent to form a N,N,N-trimethylethanolammonium salt mixture of both isomeric compounds, wherein the salt mixture has an increased amount of the isomeric salt of Isomer A relative to the amount of the isomeric salt of Isomer B, or an increased amount of the isomeric salt of Isomer B relative to the amount of the isomeric salt of Isomer A, when compared with the relative amounts of the isomeric compounds of Isomer A and Isomer B in the starting mixture.

In some embodiments, the process comprises increasing the amount of an isomeric compound of Isomer A relative to an amount of an isomeric compound of Isomer B. In some embodiments, the solvent is selected from the group consisting of acetonitrile, 2-methyltetrahydrofuran, isopropylacetate, ethanol, isopropanol, tetrahydrofuran, methyl tert-butyl ether, and isopropyl ether, or any mixture thereof. In some embodiments, the process of increasing the amount of an isomeric compound of Isomer A relative to an amount of an isomeric compound of Isomer B further comprises drying the salt mixture to form a second salt mixture comprising an increased amount of an isomeric compound of Isomer A relative to an amount of an isomeric compound of Isomer B.

In some embodiments, the process comprises increasing the amount of an isomeric compound of Isomer B relative to an amount of an isomeric compound of Isomer A. In some embodiments, the solvent is selected from the group consisting of methanol, isopropanol, dichloromethane, isopropyl ether, heptane, and toluene, or any mixture thereof.

In some embodiments, the choline salt, or crystalline form thereof disclosed herein is enriched in Isomer A. In some embodiments, the choline salt or crystalline form disclosed herein is enriched in Isomer B. As used herein, the term "enriched," refers to an increased amount of a particular compound, salt, or isomeric compound in a mixture when compared with the amount of the compound, salt, or isomeric compound in the mixture prior to being enriched. For example, a mixture enriched in an isomeric compound of Isomer A has an increased amount of the isomeric compound of Isomer A relative to the isomeric compound of Isomer B when compared with the relative amounts of the isomeric compounds of Isomer A and Isomer B in a starting mixture.

The description below is made with the understanding that the present disclosure is to be considered as an exemplification of the claimed subject matter, and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

Unless defined otherwise, all technical and scientific terms used herein have the same meaning as commonly understood by one of ordinary skill in the art.

When trade names are used herein, it is intended to independently include the tradename product and the active pharmaceutical ingredient(s) of the tradename product.

As used herein and in the appended claims, the singular forms "a" and "an", and "the" include plural referents unless the context clearly dictates otherwise. Thus, e.g., reference to "the compound" includes a plurality of such compounds and reference to "the assay" includes reference to one or more assays, and so forth.

"Pharmaceutically acceptable" refers to compounds, salts, compositions, dosage forms and other materials which are useful in preparing a pharmaceutical composition that is suitable for veterinary or human pharmaceutical use.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" refers to a salt of a compound that is pharmaceutically acceptable and that possesses (or can be converted to a form that possesses) the desired pharmacological activity of the parent compound.

"Subject" and "subjects" refers to humans, domestic animals (e.g., dogs and cats), farm animals (e.g., cattle, horses, sheep, goats and pigs), laboratory animals (e.g., mice, rats, hamsters, guinea pigs, pigs, rabbits, dogs, and monkeys), and the like.

As used herein, "treatment" or "treating" is an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and/or c) relieving the disease or condition, e.g., causing the regression of clinical symptoms, ameliorating the disease state, delaying the progression of the disease, increasing the quality of life, and/or prolonging survival.

As used herein, "delaying" development of a disease or condition means to defer, hinder, slow, retard, stabilize and/or postpone development of the disease or condition. This delay can be of varying lengths of time, depending on the history of the disease and/or subject being treated. As is evident to one skilled in the art, a sufficient or significant delay can, in effect, encompass prevention, in that the subject does not develop the disease or condition. For example, a method that "delays" development of AIDS is a method that reduces the probability of disease development in a given time frame and/or reduces extent of the disease in a given time frame, when compared to not using the method. Such comparisons may be based on clinical studies, using a statistically significant number of subjects. For example, the development of AIDS can be detected using known methods, such as confirming a subject's HIV+ status and assessing the subject's T-cell count or other indication of AIDS development, such as extreme fatigue, weight loss, persistent diarrhea, high fever, swollen lymph nodes in the neck, armpits or groin, or presence of an opportunistic condition that is known to be associated with AIDS (e.g., a condition that is generally not present in subjects with functioning immune systems but does occur in AIDS patients). Development may also refer to disease progression that may be initially undetectable and includes occurrence, recurrence and onset.

As used herein, "prevention" or "preventing" refers to a regimen that protects against the onset of the disease or disorder such that the clinical symptoms of the disease do not develop. Thus, "prevention" relates to administration of a therapy (e.g., administration of a therapeutic substance) to a subject before signs of the disease are detectable in the subject (e.g., administration of a therapeutic substance to a subject in the absence of detectable infectious agent (e.g., virus) in the subject). The subject may be an individual at risk of developing the disease or disorder, such as an individual who has one or more risk factors known to be associated with development or onset of the disease or disorder. Thus, the term "preventing HIV infection" refers to administering to a subject who does not have a detectable HIV infection an anti-HIV therapeutic substance. It is understood that the subject for anti-HIV preventative therapy may be an individual at risk of contracting the HIV virus. Further, it is understood that prevention may not result in complete protection against onset of the disease or disorder. In some instances, prevention includes reducing the risk of developing the disease or disorder. The reduction of the risk may not result in complete elimination of the risk of developing the disease or disorder.

As used herein, an "at risk" individual is an individual who is at risk of developing a condition to be treated. An individual "at risk" may or may not have detectable disease or condition, and may or may not have displayed detectable disease prior to the treatment of methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). For example, individuals at risk for AIDS are those having HIV.

As used herein, the term "therapeutically effective amount" or "effective amount" refers to an amount that is effective to elicit the desired biological or medical response, including the amount of a compound that, when administered to a subject for treating a disease, is sufficient to effect such treatment for the disease or to an amount that is effective to protect against the contracting or onset of a disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment outcome. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

"Enantiomers" are a pair of stereoisomers that are non-superimposable mirror images of each other. A 1:1 mixture of a pair of enantiomers is a "racemic" mixture. A mixture of enantiomers at a ratio other than 1:1 is a "scalemic" mixture.

"Diastereoisomers" are stereoisomers that have at least two asymmetric atoms, but which are not mirror-images of each other.

The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds and salts described herein contain one or more asymmetric centers and/or hindered rotation about a bond axis and may thus give rise to enantiomers, diastereomers, and other stereoisomeric forms that may be defined, in terms of absolute stereochemistry, as (R)- or (S)-. The present disclosure is meant to include all such possible isomers, including racemic mixtures, scalemic mixtures, diastereomeric mixtures, optically pure forms and intermediate mixtures. Optically active (R)- and (S)-isomers may be prepared using chiral synthons or chiral reagents, or resolved using conventional techniques.

Except as expressly defined otherwise, the present disclosure includes all tautomers of compounds detailed herein, even if only one tautomer is expressly represented (e.g., both tautomeric forms are intended and described by the presentation of one tautomeric form where a pair of two tautomers may exist). For example, if reference is made to a compound containing an amide (e.g., by structure or chemical name), it is understood that the corresponding imidic acid tautomer is included by this disclosure and described the same as if the amide were expressly recited either alone or together with the imidic acid. Where more than two tautomers may exist, the present disclosure includes all such tautomers even if only a single tautomeric form is depicted by chemical name and/or structure.

It is understood by one skilled in the art that this disclosure also includes any salt disclosed herein may be enriched at any or all atoms above naturally occurring isotopic ratios with one or more isotopes such as, but not limited to, deuterium ($^2$H or D).

Disclosed are also choline salts of Compound 1 in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such salts may increase resistance to metabolism, and thus may be useful for increasing the half-life of the compounds when administered to a mammal. See, e.g., Foster, "Deuterium Isotope Effects in Studies of Drug Metabolism", Trends Pharmacol. Sci., 5(12):524-527 (1984). Such salts are synthesized by means well known in the art, for example by employing starting materials in which one or more hydrogen atoms have been replaced by deuterium.

Examples of isotopes that can be incorporated into the disclosed salts also include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled salts can generally be prepared by conventional techniques known to those skilled in the art or by processes analogous to a lower predicted hepatic clearance relative to compounds A and B (about 9 and about 4 time reagent in place of the non-labeled reagent previously employed.

Compounds described herein may have chiral centers and/or geometric isomeric centers (E- and Z-isomers), and it is to be understood that all such optical, enantiomeric, diastereoisomeric and geometric isomers are encompassed. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s).

In a preferred embodiment, the current disclosure relates to the use of the choline salts and crystalline forms of the invention in treating a Retroviridae viral infection including an infection caused by the HIV virus comprising administering a therapeutically effective amount of the choline salt or crystalline form to a subject in need thereof.

In a preferred embodiment, the current disclosure relates to the use of the choline salts and crystalline forms of the invention in treating a Retroviridae viral infection including an infection caused by the HIV virus comprising administering a therapeutically effective amount of the choline salt or crystalline form to a subject in need thereof.

It is a desirable goal to discover a compound, a choline salt, or crystalline form thereof having a low $EC_{50}$. The $EC_{50}$ value refers to the concentration of a compound in an assay that achieves 50% of the maximum efficacy. A compound, salt, or crystalline form with a lower $EC_{50}$ achieves similar efficacy with lower compound, salt, or crystalline form concentration relative to a compound, salt, or crystalline form with a higher $EC_{50}$. Thus, a lower $EC_{50}$ is generally preferred for drug development.

It is a desirable goal to discover a compound, pharmaceutically acceptable salt, or crystalline form thereof that has good physical and/or chemical stability. An increase in overall stability of a compound, salt, or crystalline form can provide an increase in circulation time in the body. With less degradation, a stable compound, salt, or crystalline form can be administered in lower doses and still maintain efficacy. Also, with less degradation, there is less concern about by-products from degradation of a compound or salt.

It is a desirable goal to discover a compound, pharmaceutically acceptable salt, or crystalline form thereof that has improved pharmacokinetic and/or pharmacodynamic profiles and long half-life. It is advantageous for a drug to have a moderate or low clearance and a long half-life, as this can lead to a good bioavailability and high exposure in systemic exposure. Reducing the clearance and increasing half-life time of a compound, salt, or crystalline form could reduce the daily dose required for efficacy and therefore give a better efficacy and safety profile. Thus, improved pharmacokinetic and/or pharmacodynamic profiles and long half-life can provide for better patient compliance.

It is a desirable goal to discover a compound, a pharmaceutically acceptable salt, or crystalline form thereof that has good pharmacokinetic profile from a slow release injectable formulation. It is advantageous for a drug to have a low $EC_{50}$ and long acting pharmacokinetics, as this can lead to low frequency of administration. Reducing the frequency of administration can provide for better patient compliance. Reducing the frequency of administration can be desirable for patients with difficult or limited access to health care.

Methods of Use

In some embodiments, the choline salts or crystalline forms disclosed herein are used for preventing an HIV infection in a subject. In some embodiments, the choline salts or crystalline forms disclosed herein are used for preventing an HIV infection in a subject at risk for infection. In some embodiments, the choline salts or crystalline forms disclosed herein are used for pre-exposure prophylaxis (PrEP) to reduce the risk of sexually acquired HIV-1. It is believed that the pharmaceutically acceptable salts or crystalline forms disclosed herein are active against major HIV-1 mutants selected by clinical Protease Inhibitors (PIs), nucleoside reverse transcriptase inhibitors (NRTIs), Non-Nucleoside Reverse Transcriptase Inhibitors (NNRTIs), and Integrase inhibitors (INSTIs).

In certain embodiments, a method for treating or preventing an HIV infection in a subject (e.g., a human), comprising administering a choline salt of Compound 1, or crystalline form thereof, to the subject is disclosed.

In some embodiments, a method for treating or preventing an HIV infection in a subject (e.g., a human), comprising administering a choline salt of Compound 1, or crystalline form thereof, to the subject is disclosed.

In certain embodiments, a method for inhibiting the replication of the HIV virus, treating AIDS or delaying the onset of AIDS in a subject (e.g., a human), comprising administering a choline salt of Compound 1, or crystalline form thereof, to the subject is disclosed.

In some embodiments, a method for inhibiting the replication of the HIV virus, treating AIDS or delaying the onset of AIDS in a subject (e.g., a human), comprising administering a choline salt of Compound 1, or crystalline form thereof, to the subject is disclosed.

In certain embodiments, a method for preventing an HIV infection in a subject (e.g., a human), comprising administering a choline salt of Compound 1, or crystalline form thereof, to the subject is disclosed. In certain embodiments, the subject is at risk of contracting the HIV virus, such as a subject who has one or more risk factors known to be associated with contracting the HIV virus.

In some embodiments, a method for preventing an HIV infection in a subject (e.g., a human), comprising administering a therapeutically effective amount of a choline salt of Compound 1, or crystalline form thereof, to the subject is disclosed. In certain embodiments, the subject is at risk of contracting the HIV virus, such as a subject who has one or more risk factors known to be associated with contracting the HIV virus.

In certain embodiments, a method for treating an HIV infection in a subject (e.g., a human), comprising administering a choline salt of Compound 1, or crystalline form thereof, to the subject is disclosed.

In some embodiments, a method for treating an HIV infection in a subject (e.g., a human), comprising administering a choline salt of Compound 1, or crystalline form thereof, to the subject is disclosed.

In certain embodiments, a method for treating an HIV infection in a subject (e.g., a human), comprising administering to the subject in need thereof a therapeutically effective amount of a choline salt of Compound 1, or crystalline form thereof, in combination with a therapeutically effective amount of one or more (e.g., one, two, three, or four; or one or two; or one to three; or one to four) additional therapeutic agents selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, and combinations thereof is disclosed. In certain embodiments, a method for treating an HIV infection in a subject (e.g., a human), comprising administering to the subject in need thereof a therapeutically effective amount of a choline salt of Compound 1, or crystalline form thereof, in combination with a therapeutically effective amount of one or more (e.g., one, two, three, or four; or one or two; or one to three; or one to four) additional therapeutic agents selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or any combinations thereof is disclosed.

In some embodiments, a method for treating an HIV infection in a subject (e.g., a human), comprising administering to the subject in need thereof a therapeutically effective amount of a choline salt of Compound 1, or crystalline form thereof, in combination with a therapeutically effective amount of one or more (e.g., one, two, three, or four; or one or two; or one to three; or one to four) additional therapeutic agents selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, and combinations thereof is disclosed. In certain embodiments, a method for treating an HIV infection in a subject (e.g., a human), comprising administering to the subject in need thereof a therapeutically effective amount of a choline salt of Compound 1, or crystalline form thereof, in combination with a therapeutically effective amount of one or more (e.g., one, two, three, or four; or one or two; or one to three; or one to four) additional therapeutic agents selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or any combinations thereof is disclosed.

In certain embodiments, a method for treating an HIV infection in a subject (e.g., a human), comprising administering to the subject in need thereof a therapeutically effective amount of a pharmaceutically acceptable salt of Compound 1, or a cocrystal or crystalline form thereof, in combination with a therapeutically effective amount of one or more (e.g., one, two, three, or four; or one or two; or one to three; or one to four) additional therapeutic agents selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, and HIV nucleoside reverse transcriptase translocation inhibitors.

In certain embodiments, a choline salt of Compound 1, or crystalline form thereof, for use in medical therapy of an HIV infection (e.g. HIV-1 or the replication of the HIV virus (e.g. HIV-1) or AIDS or delaying the onset of AIDS in a subject (e.g., a human)) is disclosed.

In some embodiments, a choline salt of Compound 1, or crystalline form thereof, for use in medical therapy of an HIV infection (e.g. HIV-1 or the replication of the HIV virus (e.g. HIV-1) or AIDS or delaying the onset of AIDS in a subject (e.g., a human)) is disclosed.

In certain embodiments, a choline salt of Compound 1, or crystalline form thereof, for use in the manufacture of a medicament for treating an HIV infection or the replication of the HIV virus or AIDS or delaying the onset of AIDS in a subject (e.g., a human) is disclosed. One embodiment relates to a choline salt of Compound 1, or crystalline form thereof, for use in the prophylactic or therapeutic treatment of an HIV infection or AIDS or for use in the therapeutic treatment or delaying the onset of AIDS.

In some embodiments, a choline salt of Compound 1, or crystalline form thereof for use in the manufacture of a medicament for treating an HIV infection or the replication of the HIV virus or AIDS or delaying the onset of AIDS in a subject (e.g., a human) is disclosed. One embodiment relates to a choline salt of Compound 1, or crystalline form thereof, for use in the prophylactic or therapeutic treatment of an HIV infection or AIDS or for use in the therapeutic treatment or delaying the onset of AIDS.

In certain embodiments, the use of a choline salt of Compound 1, or crystalline form thereof, for the manufacture of a medicament for an HIV infection in a subject (e.g., a human) is disclosed. In certain embodiments, a choline salt of Compound 1, or crystalline form thereof, for use in the prophylactic or therapeutic treatment of an HIV infection is disclosed.

In some embodiments, the use of a choline salt of Compound 1, or crystalline form thereof, for the manufacture of a medicament for an HIV infection in a subject (e.g., a human) is disclosed. In certain embodiments, a choline salt of Compound 1, or crystalline form thereof, for use in the prophylactic or therapeutic treatment of an HIV infection is disclosed.

In certain embodiments, in the methods of use, the administration is to a subject (e.g., a human) in need of the treatment. In certain embodiments, in the methods of use, the administration is to a subject (e.g., a human) who is at risk of developing AIDS.

Disclosed herein is a choline salt of Compound 1, or crystalline form thereof, for use in therapy. In one embodiment, the choline salt of Compound 1, or crystalline form thereof, is for use in a method of treating an HIV infection or the replication of the HIV virus or AIDS or delaying the onset of AIDS in a subject (e.g., a human).

In some embodiments, disclosed herein is a choline salt of Compound 1, or crystalline form thereof, for use in therapy. In some embodiments, the choline salt of Compound 1, or crystalline form thereof, is for use in a method of treating an HIV infection or the replication of the HIV virus or AIDS or delaying the onset of AIDS in a subject (e.g., a human).

Also disclosed herein is a choline salt of Compound 1, or crystalline form thereof, for use in a method of treating or preventing HIV infection in a subject in need thereof. In certain embodiments, a choline salt of Compound 1, or crystalline form thereof, for use in a method of treating HIV infection in a subject in need thereof is provided. In certain embodiments, the subject in need thereof is a human who has been infected with HIV. In certain embodiments, the subject in need thereof is a human who has been infected with HIV but who has not developed AIDS. In certain embodiments, the subject in need thereof is a subject at risk for developing AIDS. In certain embodiments, the subject in need thereof is a human who has been infected with HIV and who has developed AIDS.

In some embodiments, disclosed herein is a choline salt of Compound 1, or crystalline form thereof, for use in a method of treating or preventing HIV infection in a subject in need thereof. In certain embodiments, a choline salt of Compound 1, or crystalline form thereof, for use in a method of treating HIV infection in a subject in need thereof is provided. In certain embodiments, the subject in need thereof is a human who has been infected with HIV. In certain embodiments, the subject in need thereof is a human who has been infected with HIV but who has not developed AIDS. In certain embodiments, the subject in need thereof is a subject at risk for developing AIDS. In certain embodiments, the subject in need thereof is a human who has been infected with HIV and who has developed AIDS.

In one embodiment, a choline salt of Compound 1, or crystalline form thereof, in combination with one or more (e.g. one, two, three, or four; or one or two; or one to three; or one to four) additional therapeutic agents as described herein for use in a method of treating or preventing HIV infection in a subject in need thereof is provided. In one embodiment, said additional therapeutic agents are selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or any combinations thereof. In one embodiment, said additional therapeutic agents are selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, and combinations thereof.

In some embodiments, a choline salt of Compound 1, or crystalline form thereof, in combination with one or more (e.g. one, two, three, or four; or one or two; or one to three; or one to four) additional therapeutic agents as described herein for use in a method of treating or preventing HIV infection in a subject in need thereof is provided. In one embodiment, said additional therapeutic agents are selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or any combinations thereof. In one embodiment, said additional therapeutic agents are selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, and combinations thereof.

In one embodiment, a choline salt of Compound 1, or crystalline form thereof, in combination with a first additional therapeutic agent selected from the group consisting of tenofovir alafenamide fumarate, tenofovir alafenamide, and tenofovir alafenamide hemifumarate, and a second additional therapeutic agent, wherein the second additional therapeutic agent is emtricitabine, is provided for use in a method of treating or preventing HIV infection in a subject in need thereof. In a particular embodiment, a choline salt of Compound 1, or crystalline form thereof, in combination with a first additional therapeutic agent selected from the group consisting of tenofovir disoproxil fumarate, tenofovir disoproxil, and tenofovir disoproxil hemifumarate, and a second additional therapeutic agent, wherein the second additional therapeutic agent is emtricitabine, is provided for use in a method of treating or preventing HIV infection in a subject in need thereof.

In some embodiments, a choline salt of Compound 1, or crystalline form thereof, in combination with a first additional therapeutic agent selected from the group consisting of tenofovir alafenamide fumarate, tenofovir alafenamide, and tenofovir alafenamide hemifumarate, and a second additional therapeutic agent, wherein the second additional therapeutic agent is emtricitabine, is provided for use in a method of treating or preventing HIV infection in a subject in need thereof. In a particular embodiment, a choline salt of Compound 1, or crystalline form thereof, in combination with a first additional therapeutic agent selected from the group consisting of tenofovir disoproxil fumarate, tenofovir disoproxil, and tenofovir disoproxil hemifumarate, and a second additional therapeutic agent, wherein the second additional therapeutic agent is emtricitabine, is provided for use in a method of treating or preventing HIV infection in a subject in need thereof.

In some embodiments, a pharmaceutically acceptable salt of Compound 1, or a cocrystal or crystalline form thereof, is provided in combination with at least one additional therapeutic agent selected from the group consisting of:

(1) nucleoside reverse transcriptase translocation inhibitors ("NRTTIs"), such as 4'-Ethynyl-2-fluoro-2'-deoxyadenosine triphosphate (also known as MK-8591 and EFdA);

(2) nucleoside or nucleotide reverse-transcriptase inhibitors ("NRTIs"), such as tenofovir alafenamide fumarate, tenofovir alafenamide, tenofovir alafenamide hemifumarate, GS-9131, and GS-9148;

(3) non-nucleoside or non-nucleotide reverse transcriptase inhibitors ("NNRTIs"), such as efavirenz, etravirine, rilpivirine, nevirapine, and delavirdine;

(4) protease Inhibitors ("PIs"), such as amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, and TMC-31091; and (5) integrase strand transfer inhibitors ("INSTIs"), such as Bictegravir, cabotegravir, raltegravir, and dolutegravir.

In a particular embodiment, a choline salt of Compound 1, or crystalline form thereof, is provided for use to prevent HIV infection from taking hold if the individual is exposed to the virus and/or to keep the virus from establishing a permanent infection and/or to prevent the appearance of symptoms of the disease and/or to prevent the virus from reaching detectable levels in the blood, for example for pre-exposure prophylaxis (PrEP) or post-exposure prophylaxis (PEP). Accordingly, in certain embodiments, methods for reducing the risk of acquiring HIV (e.g., HIV-1 and/or HIV-2) are provided. For example, methods for reducing the risk of acquiring HIV (e.g., HIV-1 and/or HIV-2) comprise administration of a choline salt of Compound 1, or crystalline form thereof. In certain embodiments, methods for reducing the risk of acquiring HIV (e.g., HIV-1 and/or HIV-2) comprise administration of a choline salt of Compound 1, or crystalline form thereof, in combination with one or more additional therapeutic agents. In certain embodiments, methods for reducing the risk of acquiring HIV (e.g., HIV-1 and/or HIV-2) comprise administration of a pharmaceutical composition comprising a therapeutically effective amount of a choline salt of Compound 1, or crystalline form thereof, and a choline excipient.

In some embodiments, a choline salt of Compound 1, or crystalline form thereof, is provided for use to prevent HIV infection from taking hold if the individual is exposed to the virus and/or to keep the virus from establishing a permanent infection and/or to prevent the appearance of symptoms of the disease and/or to prevent the virus from reaching detectable levels in the blood, for example for pre-exposure prophylaxis (PrEP) or post-exposure prophylaxis (PEP). Accordingly, in certain embodiments, methods for reducing the risk of acquiring HIV (e.g., HIV-1 and/or HIV-2) are provided. For example, methods for reducing the risk of acquiring HIV (e.g., HIV-1 and/or HIV-2) comprise administration of a choline salt of Compound 1, or crystalline form thereof. In certain embodiments, methods for reducing the risk of acquiring HIV (e.g., HIV-1 and/or HIV-2) comprise administration of a choline salt of Compound 1, or crystalline form thereof, in combination with one or more additional therapeutic agents. In certain embodiments, methods for reducing the risk of acquiring HIV (e.g., HIV-1 and/or HIV-2) comprise administration of a pharmaceutical composition comprising a therapeutically effective amount of a choline salt of Compound 1, or crystalline form thereof, and a choline excipient.

In certain embodiments, methods for reducing the risk of acquiring HIV (e.g., HIV-1 and/or HIV-2) comprise administration of a choline salt of Compound 1, or crystalline form thereof, in combination with safer sex practices. In certain embodiments, methods for reducing the risk of acquiring HIV (e.g., HIV-1 and/or HIV-2) comprise administration to an individual at risk of acquiring HIV. Examples of individuals at high risk for acquiring HIV include, without limitation, an individual who is at risk of sexual transmission of HIV.

In some embodiments, methods for reducing the risk of acquiring HIV (e.g., HIV-1 and/or HIV-2) comprise administration of a choline salt of Compound 1, or crystalline form thereof, in combination with safer sex practices. In certain embodiments, methods for reducing the risk of acquiring HIV (e.g., HIV-1 and/or HIV-2) comprise administration to an individual at risk of acquiring HIV. Examples of individuals at high risk for acquiring HIV include, without limitation, an individual who is at risk of sexual transmission of HIV.

In certain embodiments, the reduction in risk of acquiring HIV is at least about 40%, 50%, 60%, 70%, 80%, 90%, or 95%. In certain embodiments, the reduction in risk of acquiring HIV is at least about 75%. In certain embodiments, the reduction in risk of acquiring HIV is about 80%, 85%, or 90%.

In another embodiment, the use of a choline salt of Compound 1, or crystalline form thereof, for the manufacture of a medicament for the treatment of an HIV infection in a human being having or at risk of having the infection is disclosed.

In some embodiments, the use of a choline salt of Compound 1, or crystalline form thereof, for the manufacture of a medicament for the treatment of an HIV infection in a human being having or at risk of having the infection is disclosed.

Also disclosed herein is a choline salt of Compound 1, or crystalline form thereof, for use in the therapeutic treatment or delaying the onset of AIDS.

In some embodiments, disclosed herein is a choline salt of Compound 1, or crystalline form thereof, for use in the therapeutic treatment or delaying the onset of AIDS.

Also disclosed herein is a choline salt of Compound 1, or crystalline form thereof, for use in the prophylactic or therapeutic treatment of an HIV infection.

In some embodiments, disclosed herein is a choline salt of Compound 1, or crystalline form thereof, for use in the prophylactic or therapeutic treatment of an HIV infection.

In certain embodiments, a choline salt of Compound 1, or crystalline form thereof, can be used as a research tool.

Routes of Administration

The choline salt of Compound 1, or crystalline form thereof, (also referred to herein as the active ingredient) can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with, for example, the condition of the recipient. In certain embodiments, the compounds disclosed can be dosed parenterally. In certain embodiments, the compounds disclosed can be dosed intravenous, subcutaneous, or intramuscular. In certain embodiments, the compounds, salts, and crystalline forms disclosed are orally bioavailable and can be dosed orally.

In some embodiments, the choline salt of Compound 1, or crystalline form thereof, may be administered with a syringe suitable for administration of the compound. In some embodiments, the syringe is disposable. In some embodiments, the syringe is reusable. In some embodiments, the syringe is pre-filled with the choline salt of Compound 1, or crystalline form thereof.

In some embodiments, the pharmaceutically acceptable salt of Compound 1, or a cocrystal or crystalline form thereof, may be administered via injection, using an injection device. In some embodiments, the injection device is or includes a syringe, which can be employed manually, or as part of a syringe-containing injection device, such as, but not limited to, one with a needle safety shield. A wide variety of injection devices can be used, such as, for example and not limited to, a handheld or wearable autoinjector, a handheld or wearable manual injector, an on-body injector, a syrette, a jet injector, or a pen injector, each of which can be reusable or disposable.

In some embodiments, the choline salt of Compound 1, or crystalline form thereof, may be administered with an autoinjector comprising a syringe. In some embodiments, the syringe is disposable. In some embodiments, the syringe is reusable. In some embodiments, the syringe is pre-filled with the choline salt of Compound 1, or crystalline form thereof.

Dosing Regimen

The choline salt of Compound 1, or crystalline form thereof, may be administered to a subject in accordance with an effective dosing regimen for a desired period of time or duration, such as at least about one day, at least about one week, at least about one month, at least about 2 months, at least about 3 months, at least about 4 months, at least about 6 months, or at least about 12 months or longer. In one variation, the salt or crystalline form is administered on a daily or intermittent schedule. In one variation, the salt or crystalline form is administered on a monthly schedule. In one variation, the salt or crystalline form is administered every two months. In one variation, the salt or crystalline form is administered every three months. In one variation, the salt or crystalline form is administered every four months. In one variation, the salt or crystalline form is administered every five months. In one variation, the salt or crystalline form is administered every 6 months.

In some embodiments, the choline salt of Compound 1, or crystalline form thereof, may be administered to a subject at least about one month, at least about 4 months, or at least about 6 months. In some embodiments, the choline salt of Compound 1, or crystalline form thereof, may be subcutaneously administered to a subject at least about one month. In some embodiments, the choline salt of Compound 1, or crystalline form thereof, may be subcutaneously or intramuscularly administered to a subject at least about 4 months, or at least about 6 months.

The dosage or dosing frequency of the choline salt of Compound 1, or crystalline form thereof, may be adjusted over the course of the treatment, based on the judgment of the administering physician.

In some embodiments, the dosage or dosing frequency of the choline salt of Compound 1, or crystalline form thereof, may be adjusted over the course of the treatment, based on the judgment of the administering physician.

The choline salt of Compound 1, or crystalline form thereof may be administered to a subject (e.g., a human) in an effective amount. In certain embodiments, the choline salt of Compound 1, or crystalline form thereof is administered once daily.

In some embodiments, the choline salt of Compound 1, or crystalline form thereof, may be administered to a subject (e.g., a human) in an therapeutically effective amount. In some embodiments, the choline salt of Compound 1, or crystalline form thereof, is administered once daily. In some embodiments, the choline salt of Compound 1, or crystalline form thereof, is administered monthly. In some embodiments, the choline salt of Compound 1, or crystalline form thereof, is administered every three months. In some embodiments, the choline salt of Compound 1, or crystalline form thereof, is administered every four months. In some embodiments, the choline salt of Compound 1, or crystalline form thereof, is administered every six months.

A choline salt of Compound 1, or crystalline form thereof, disclosed herein may be administered in a dosage amount that is effective. For example, the dosage amount can be from 1 mg to 1000 mg of compound. In certain embodiments, the dosage amount is about 1, 10, 20, 30, 40, 50, 60, 70, 80, 90, 95, 100, 105, 110, 120, 130, 140, or 150 mg of compound. In certain embodiments the dosage amount is about 100, 150, 200, 250, 300, 350, 400, 450, 500, 550, 600, 650, 700, 750, 800, 850, 900, 950, or 1000 mg.

In some embodiments, the choline salt of Compound 1, or crystalline form thereof, is administered in a once daily dose. In some embodiments, the choline salt of Compound 1, or crystalline form thereof, is administered in a once daily dose of about 1 mg.

In some embodiments, the choline salt of Compound 1, or crystalline form thereof, is administered monthly. In some embodiments, the choline salt of Compound 1, or crystalline form thereof, is administered monthly at a dose of about 100 mg.

In some embodiments, the choline salt of Compound 1, or crystalline form thereof, is administered every 6 months. In some embodiments, the choline salt of Compound 1, or crystalline form thereof, is administered every 6 months at a dose of about 600 mg.

Combination Therapies

In certain embodiments, a method for treating or preventing an HIV infection in a human having or at risk of having the infection is provided, comprising administering to the human a therapeutically effective amount of a choline salt of Compound 1, or crystalline form thereof, disclosed herein in combination with a therapeutically effective amount of one or more (e.g., one, two, three, or four; or one or two; or one to three; or one to four) additional therapeutic agents. In one embodiment, a method for treating an HIV infection in a human having or at risk of having the infection is provided, comprising administering to the human a therapeutically effective amount of a choline salt of Compound 1, or crystalline form thereof, disclosed herein in combination with a therapeutically effective amount of one or more (e.g., one, two, three, or four; or one or two; or one to three; or one to four) additional therapeutic agents.

In some embodiments, a method for treating or preventing an HIV infection in a human having or at risk of having the infection is provided, comprising administering to the human a therapeutically effective amount of a choline salt of Compound 1, or crystalline form thereof, in combination with a therapeutically effective amount of one or more (e.g., one, two, three, or four; or one or two; or one to three; or one to four) additional therapeutic agents. In one embodiment, a method for treating an HIV infection in a human having or at risk of having the infection is provided, comprising administering to the human a therapeutically effective amount of a choline salt of Compound 1, or crystalline form thereof, in combination with a therapeutically effective amount of one or more (e.g., one, two, three, or four; or one or two; or one to three; or one to four) additional therapeutic agents.

In one embodiment, pharmaceutical compositions comprising a choline salt of Compound 1, or crystalline form thereof, in combination with one or more (e.g., one, two, three, or four; or one or two; or one to three; or one to four) additional therapeutic agents, and a choline excipient are provided.

In some embodiments, pharmaceutical compositions comprising a choline salt of Compound 1, or crystalline form thereof, in combination with one or more (e.g., one, two, three, or four; or one or two; or one to three; or one to four) additional therapeutic agents, and a choline excipient are provided.

In certain embodiments, the present disclosure provides a method for treating an HIV infection, comprising administering to a subject in need thereof a therapeutically effective amount of a choline salt of Compound 1, or crystalline form thereof, in combination with a therapeutically effective amount of one or more additional therapeutic agents which are suitable for treating an HIV infection.

In certain embodiments, the present disclosure provides a method for treating an HIV infection, comprising administering to a subject in need thereof a therapeutically effective amount of a choline salt of Compound 1, or crystalline form thereof, in combination with a therapeutically effective amount of one or more additional therapeutic agents which are suitable for treating an HIV infection.

In certain embodiments, a choline salt of Compound 1, or crystalline form thereof, disclosed herein is combined with one, two, three, four, or more additional therapeutic agents. In certain embodiments, a choline salt of Compound 1, or crystalline form thereof, disclosed herein is combined with one additional therapeutic agent. In certain embodiments, a choline salt of Compound 1, or crystalline form thereof, disclosed herein is combined with two additional therapeutic agents. In other embodiments, a choline salt of Compound 1, or crystalline form thereof, disclosed herein is combined with three additional therapeutic agents. In further embodiments, a choline salt of Compound 1, or crystalline form thereof, disclosed herein is combined with four additional therapeutic agents. The one, two, three, four, or more additional therapeutic agents can be different therapeutic agents selected from the same class of therapeutic agents, and/or they can be selected from different classes of therapeutic agents.

In some embodiments, a choline salt of Compound 1, or crystalline form thereof, disclosed herein is combined with one, two, three, four, or more additional therapeutic agents. In certain embodiments, a choline salt of Compound 1, or crystalline form thereof, disclosed herein is combined with one additional therapeutic agent. In certain embodiments, a choline salt of Compound 1, or crystalline form thereof, disclosed herein is combined with two additional therapeutic agents. In other embodiments, a choline salt of Compound 1, or crystalline form thereof, disclosed herein is combined with three additional therapeutic agents. In further embodiments, a choline salt of Compound 1, or crystalline form thereof, disclosed herein is combined with four additional therapeutic agents. The one, two, three, four, or more additional therapeutic agents can be different therapeutic agents selected from the same class of therapeutic agents, and/or they can be selected from different classes of therapeutic agents.

Administration of HIV Combination Therapy

In certain embodiments, a choline salt of Compound 1, or crystalline form thereof, disclosed herein is administered with one or more additional therapeutic agents. Co-administration of a choline salt of Compound 1, or crystalline form thereof, disclosed herein with one or more additional therapeutic agents generally refers to simultaneous or sequential administration of a choline salt of Compound 1, or crystalline form thereof, and one or more additional therapeutic agents, such that therapeutically effective amounts of the choline salt of Compound 1, or crystalline form thereof, and the one or more additional therapeutic agents are both present in the body of the subject. When administered sequentially, the combination may be administered in two or more administrations.

In some embodiments, a choline salt of Compound 1, or crystalline form thereof, disclosed herein is administered with one or more additional therapeutic agents. Co-administration of a choline salt of Compound 1, or crystalline form thereof, disclosed herein with one or more additional therapeutic agents generally refers to simultaneous or sequential administration of the choline salt of Compound 1, or crystalline form thereof, and one or more additional therapeutic agents, such that therapeutically effective amounts of the a choline salt of Compound 1, or crystalline form thereof, and the one or more additional therapeutic agents are both present in the body of the subject. When administered sequentially, the combination may be administered in two or more administrations.

Co-administration includes administration of unit dosages of the choline salt of Compound 1, or crystalline form thereof, before or after administration of unit dosages of one or more additional therapeutic agents. For example, the choline salt of Compound 1, or crystalline form thereof, may be administered within seconds, minutes, or hours of the administration of the one or more additional therapeutic agents. In some embodiments, a unit dose of a choline salt of Compound 1, or crystalline form thereof, is administered first, followed within seconds or minutes by administration of a unit dose of one or more additional therapeutic agents. Alternatively, a unit dose of one or more additional therapeutic agents is administered first, followed by administration of a unit dose of a choline salt of Compound 1, or crystalline form thereof, within seconds or minutes. In other embodiments, a unit dose of a choline salt of Compound 1, or crystalline form thereof, is administered first, followed, after a period of hours (e.g., 1-12 hours), by administration of a unit dose of one or more additional therapeutic agents. In yet other embodiments, a unit dose of one or more additional therapeutic agents is administered first, followed, after a period of hours (e.g., 1-12 hours), by administration of a unit dose of a choline salt of Compound 1, or crystalline form thereof.

In certain embodiments, a choline salt of Compound 1, or crystalline form thereof, disclosed herein is combined with one or more additional therapeutic agents in a unitary dosage form for simultaneous administration to a subject. In certain embodiments, such a unitary dosage form can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. In certain embodiments, the compounds disclosed can be dosed parenterally. In certain embodiments, the unitary dosage form can be dosed intravenous, subcutaneous, or intramuscular. In certain embodiments, the unitary dosage form is orally bioavailable and can be dosed orally. In certain embodiments, the unitary dosage form can be a solid dosage form for oral administration.

The choline salt of Compound 1, or crystalline form thereof, disclosed herein in combination with one or more additional therapeutic agents can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. In certain embodiments, the choline salt of Compound 1, or crystalline form thereof, disclosed herein can be dosed parenterally. In certain embodiments, the choline salt of Compound 1, or crystalline form thereof, disclosed herein can be dosed intravenous, subcutaneous, or intramuscular. In certain embodiments, the choline salt of Compound 1, or crystalline form thereof, disclosed herein are orally bioavailable and can be dosed orally.

In certain embodiments, a choline salt of Compound 1, or crystalline form thereof, disclosed herein is formulated as a tablet, which may optionally contain one or more other compounds useful for treating HIV. In certain embodiments, the tablet can one or more other compounds useful for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, a pharmaceutically acceptable salt of Compound 1, or a cocrystal or crystalline form thereof, disclosed herein is formulated as a tablet, which may optionally contain one or more other compounds useful for treating HIV. In certain embodiments, the tablet can one or more other compounds useful for treating HIV, such as HIV nucleoside reverse transcriptase translocation inhibitors, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, such tablets are suitable for once daily dosing.

HIV Combination Therapy

In some embodiments, a pharmaceutically acceptable salt of Compound 1, or a cocrystal or crystalline form thereof, disclosed herein is administered with at least one additional therapeutic agent.

In the above embodiments, the additional therapeutic agent may be an anti-HIV agent selected from the group consisting of combination drugs for treating HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In some embodiments, the additional therapeutic agent is selected from the group consisting of combination drugs for HIV, other drugs for treating HIV, HIV nucleoside reverse transcriptase translocation inhibitors, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof. In some embodiments, the additional therapeutic agent is selected from immunomodulators, immunotherapeutic agents, antibody-drug conjugates, gene modifiers, gene editors (such as CRISPR/Cas9, zinc finger nucleases, homing nucleases, synthetic nucleases, TALENs), and cell therapies such as chimeric antigen receptor T-cell, CAR-T (e.g., YESCARTA® (axicabtagene ciloleucel)), and engineered T cell receptors, TCR-T.

HIV Combination Drugs

Examples of combination drugs include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; cabotegravir and rilpivirine; cabotegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine; lamivudine+abacavir+zidovudine; lamivudine+abacavir; lamivudine+tenofovir disoproxil fumarate; lamivudine+zidovudine+nevirapine; lopinavir+ritonavir; lopinavir+ritonavir+abacavir+lamivudine; lopinavir+ritonavir+zidovudine+lamivudine; tenofovir+lamivudine; and tenofovir disoproxil fumarate+emtricitabine+rilpivirine hydrochloride; lopinavir, ritonavir, zidovudine and lamivudine; Vacc-4x and romidepsin; and APH-0812.

Other HIV Drugs

Examples of other drugs for treating HIV include acemannan, alisporivir, BanLec, deferiprone, Gamimune, metenkefalin, naltrexone, Prolastin, REP 9, RPI-MN, VSSP, Hlviral, SB-728-T, 1,5-dicaffeoylquinic acid, rHIV7-shl-TAR-CCRSRZ, AAV-eCD4-Ig gene therapy, MazF gene therapy, BlockAide, ABX-464, AG-1105, APH-0812, BIT-225, CYT-107, HGTV-43, HPH-116, HS-10234, IMO-3100, IND-02, MK-1376, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

HIV Nucleoside Reverse Transcriptase Translocation Inhibitors

Examples of HIV nucleoside reverse transcriptase translocation inhibitors ("NRTTIs") include 4'-Ethynyl-2-fluoro-2'-deoxyadenosine triphosphate (also known as MK-8591 and EFdA).

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, AIC-292, KM-023, and VM-1500. Further examples of non-nucleoside reverse transcriptase inhibitors are disclosed in U.S. Patent Publication No. US2016/0250215.

Examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, GS-9131, GS-9148, and KP-1461.

In some embodiments, examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, GS-9131, GS-9148, KP-1461, and 4'-ethynyl-2-fluoro-2'-deoxyadenosine (EFdA).

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169 and cabotegravir.

Examples of HIV non-catalytic site, or allosteric, integrase inhibitors (NCINI) include CX-05045, CX-05168, and CX-14442.

HIV Entry Inhibitors

Examples of HIV entry (fusion) inhibitors include cenicriviroc, CCR5 inhibitors, gp41 inhibitors, CD4 attachment inhibitors, gp120 inhibitors, and CXCR4 inhibitors.

Examples of CCR5 inhibitors include aplaviroc, vicriviroc, maraviroc, cenicriviroc, PRO-140, adaptavir (RAP-101), nifeviroc (TD-0232), anti-GP120/CD4 or CCR5 bispecific antibodies, B-07, MB-66, polypeptide C25P, TD-0680, and vMIP (Haimipu).

Examples of gp41 inhibitors include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

Examples of CD4 attachment inhibitors include ibalizumab and CADA analogs

Examples of gp120 inhibitors include Radha-108 (receptol) 3B3-PE38, BanLec, bentonite-based nanomedicine, fostemsavir tromethamine, IQP-0831, and BMS-663068

Examples of CXCR4 inhibitors include plerixafor, ALT-1188, N15 peptide, and vMIP (Haimipu).

HIV Maturation Inhibitors

Examples of HIV maturation inhibitors include BMS-955176 and GSK-2838232.

Latency Reversing Agents

Examples of latency reversing agents include histone deacetylase (HDAC) inhibitors, proteasome inhibitors such as velcade, protein kinase C (PKC) activators, BET-bromodomain 4 (BRD4) inhibitors, ionomycin, PMA, SAHA (suberanilohydroxamic acid, or suberoyl, anilide, and hydroxamic acid), IL-15, JQ1, disulfram, amphotericin B, and ubiquitin inhibitors such as largazole analogs, and GSK-343.

Examples of HDAC inhibitors include romidepsin, vorinostat, and panobinostat.

Examples of PKC activators include indolactam, prostratin, ingenol B, and DAG-lactones.

Capsid Inhibitors

Examples of capsid inhibitors include capsid polymerization inhibitors or capsid disrupting compounds, HIV nucleocapsid p7 (NCp7) inhibitors such as azodicarbonamide, HIV p24 capsid protein inhibitors, AVI-621, AVI-101, AVI-201, AVI-301, and AVI-CAN1-15 series.

Immune-Based Therapies

Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 agonists; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; rintatolimod, polymer polyethyleneimine (PEI); gepon; rintatolimod; IL-12; WF-10; VGV-1; MOR-22; BMS-936559; CYT-107, interleukin-15/Fc fusion protein, normferon, peginterferon alfa-2a, peginterferon alfa-2b, recombinant interleukin-15, RPI-MN, GS-9620, and IR-103.

Phosphatidylinositol 3-kinase (PI3K) Inhibitors

Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

HIV Antibodies, Bispecific Antibodies, and "Antibody-like" Therapeutic Proteins

Examples of HIV antibodies, bispecific antibodies, and "antibody-like" therapeutic proteins include DARTs®, DUOBODIES®, BITES®, XmAbs®, TandAbs®, Fab derivatives, bnABs (broadly neutralizing HIV-1 antibodies), BMS-936559, TMB-360, and those targeting HIV gp120 or gp41, antibody-Recruiting Molecules targeting HIV, anti-CD63 monoclonal antibodies, anti-GB virus C antibodies, anti-GP120/CD4, CCR5 bispecific antibodies, anti-nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, MB-66

Examples of those targeting HIV in such a manner include bavituximab, UB-421, C2F5, C2G12, C4E10, C2F5+C2G12+C4E10, 3-BNC-117, PGT145, PGT121, MDX010 (ipilimumab), VRC01, A32, 7B2, 10E8, VRC-07-523, VRC-HIVMAB080-00-AB, MGD-014 and VRC07.

Pharmacokinetic Enhancers

Examples of pharmacokinetic enhancers include cobicistat and ritonavir.

Additional Therapeutic Agents

Examples of additional therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

HIV Vaccines

Examples of HIV vaccines include peptide vaccines, recombinant subunit protein vaccines, live vector vaccines, DNA vaccines, CD4-derived peptide vaccines, vaccine combinations, rgp120 (AIDSVAX), ALVAC HIV (vCP1521)/AIDSVAX B/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-05, VAC-3S, multiclade DNA recombinant adenovirus-5 (rAd5), Pennvax-G, Pennvax-GP, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multi-HIV (FIT-06), gp140[delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, TVI-HIV-1, Ad-4 (Ad4-env Clade C+Ad4-mGag), EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICH-vac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV-1 vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4x+romidepsin, variant gp120 polypeptide vaccine, rAd5 gag-pol env A/B/C vaccine.

HIV Combination Therapy

In a particular embodiment, a choline salt of Compound 1, or crystalline form thereof, disclosed herein is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In some embodiments, a choline salt of Compound 1, or crystalline form thereof, disclosed herein is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; abacavir sulfate; 4'-ethynyl-2-fluoro-2'-deoxyadenosine (EFdA); and Bictegravir, or a pharmaceutically acceptable salt thereof.

It will be appreciated by one of skill in the art that the additional therapeutic agents listed above may be included in more than one of the classes listed above. The particular classes are not intended to limit the functionality of those compounds listed in those classes.

In a specific embodiment a choline salt of Compound 1, or crystalline form thereof, disclosed herein is combined with one or two HIV nucleoside or nucleotide inhibitors of reverse transcriptase. In a specific embodiment, a choline salt of Compound 1, or crystalline form thereof, disclosed herein is combined with an HIV nucleoside or nucleotide inhibitor of reverse transcriptase and an HIV non-nucleoside inhibitor of reverse transcriptase. In another specific embodiment, a choline salt of Compound 1, or crystalline form thereof, disclosed herein is combined with an HIV nucleoside or nucleotide inhibitor of reverse transcriptase, and an HIV protease inhibiting compound. In an additional embodiment, a choline salt of Compound 1, or crystalline form thereof, disclosed herein is combined with an HIV nucleoside or nucleotide inhibitor of reverse transcriptase, an HIV non-nucleoside inhibitor of reverse transcriptase, and a pharmacokinetic enhancer. In certain embodiments, a choline salt of Compound 1, or crystalline form thereof, disclosed herein is combined with at least one HIV nucleoside inhibitor of reverse transcriptase, an integrase inhibitor, and a pharmacokinetic enhancer. In another embodiment, a choline salt of Compound 1, or crystalline form thereof, disclosed herein is combined with two HIV nucleoside or nucleotide inhibitors of reverse transcriptase.

In some embodiments, a choline salt of Compound 1, or crystalline form thereof, disclosed herein is combined with one or two HIV nucleoside or nucleotide inhibitors of reverse transcriptase. In a specific embodiment, a choline salt of Compound 1, or crystalline form thereof, disclosed herein is combined with an HIV nucleoside or nucleotide inhibitor of reverse transcriptase and an HIV non-nucleoside inhibitor of reverse transcriptase. In another specific embodiment, a choline salt of Compound 1, or crystalline form thereof, disclosed herein is combined with an HIV nucleoside or nucleotide inhibitor of reverse transcriptase, and an HIV protease inhibiting compound. In an additional embodiment, a choline salt of Compound 1, or crystalline form thereof, disclosed herein is combined with an HIV nucleoside or nucleotide inhibitor of reverse transcriptase, an HIV non-nucleoside inhibitor of reverse transcriptase, and a pharmacokinetic enhancer. In certain embodiments, a choline salt of Compound 1, or crystalline form thereof, disclosed herein is combined with at least one HIV nucleoside inhibitor of reverse transcriptase, an integrase inhibitor, and a pharmacokinetic enhancer. In another embodiment, a choline salt of Compound 1, or crystalline form thereof, disclosed herein is combined with two HIV nucleoside or nucleotide inhibitors of reverse transcriptase.

In a particular embodiment, a choline salt of Compound 1, or crystalline form thereof, disclosed herein is combined with abacavir sulfate, tenofovir, tenofovir disoproxil, tenofovir disoproxil fumarate, tenofovir disoproxil hemifumarate, tenofovir alafenamide, tenofovir alafenamide fumarate or tenofovir alafenamide hemifumarate.

In some embodiments, a choline salt of Compound 1, or crystalline form thereof, disclosed herein is combined with abacavir sulfate, tenofovir, tenofovir disoproxil, tenofovir disoproxil fumarate, tenofovir disoproxil hemifumarate, tenofovir alafenamide, tenofovir alafenamide fumarate, tenofovir alafenamide hemifumarate, bictegravir (or a choline salt thereof), or 4'-ethynyl-2-fluoro-2'-deoxyadenosine (EFdA).

In a particular embodiment, a choline salt of Compound 1, or crystalline form thereof, disclosed herein is combined with tenofovir, tenofovir disoproxil, tenofovir disoproxil fumarate, tenofovir alafenamide, tenofovir alafenamide fumarate or tenofovir alafenamide hemifumarate.

In some embodiments, a choline salt of Compound 1, or crystalline form thereof, disclosed herein is combined with tenofovir, tenofovir disoproxil, tenofovir disoproxil fumarate, tenofovir alafenamide, tenofovir alafenamide fumarate, tenofovir alafenamide hemifumarate, bictegravir (or a pharmaceutically acceptable salt thereof), or 4'-ethynyl-2-fluoro-2'-deoxyadenosine (EFdA).

In some embodiments, a choline salt of Compound 1, or crystalline form thereof, disclosed herein a choline salt of Compound 1, or crystalline form thereof, disclosed herein is combined with a first additional therapeutic agent selected from the group consisting of abacavir sulfate, tenofovir, tenofovir disoproxil, tenofovir disoproxil fumarate, tenofovir alafenamide, tenofovir alafenamide fumarate and tenofovir alafenamide hemifumarate, and a second additional therapeutic agent selected from the group consisting of emtricitabine and lamivudine.

In a particular embodiment, a choline salt of Compound 1, or crystalline form thereof, disclosed herein is combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine. In a particular embodiment, a choline salt of Compound 1, or crystalline form thereof, disclosed herein is combined with a first additional therapeutic agent selected from the group consisting of tenofovir alafenamide fumarate, tenofovir alafenamide, and tenofovir alafenamide hemifumarate, and a second additional therapeutic agent, wherein the second additional therapeutic agent is emtricitabine. In a particular embodiment, a choline salt of Compound 1, or crystalline form thereof, disclosed herein is combined with a first additional therapeutic agent selected from the group consisting of tenofovir disoproxil fumarate, tenofovir disoproxil, and tenofovir disoproxil hemifumarate, and a second additional therapeutic agent, wherein the second additional therapeutic agent is emtricitabine. In some embodiments, the choline salt of Compound 1, or crystalline form thereof, and the first and second additional therapeutic agents as disclosed above are administered simultaneously. Optionally, the choline salt of Compound 1, or crystalline form thereof, and the first and second additional therapeutic agents as disclosed above are combined in a unitary dosage form for simultaneous administration to a subject. In other embodiments, the choline salt of Compound 1, or crystalline form thereof, and the first and second additional therapeutic agents as disclosed above are administered sequentially.

In some embodiments, a choline salt of Compound 1, or crystalline form thereof, disclosed herein is combined with bictegravir or a pharmaceutically acceptable salt thereof.

In some embodiments, a pharmaceutically acceptable salt of Compound 1, or a cocrystal or crystalline form thereof, disclosed herein is combined with 4'-ethynyl-2-fluoro-2'-deoxyadenosine (EFdA).

A choline salt of Compound 1, or crystalline form thereof, disclosed herein may be combined with one or more additional therapeutic agents in any dosage amount of the choline salt of Compound 1, or crystalline form thereof (e.g., from 1 mg to 1000 mg of the salt or crystalline form).

In some embodiments, a choline salt of Compound 1, or crystalline form thereof, disclosed herein may be combined with one or more additional therapeutic agents in any dosage amount of the choline salt of Compound 1, or crystalline form thereof (e.g., from 1 mg to 1000 mg of the salt or crystalline form).

In certain embodiments, a choline salt of Compound 1, or crystalline form thereof, disclosed herein is combined with 5-30 mg tenofovir alafenamide fumarate, tenofovir alafenamide hemifumarate, or tenofovir alafenamide, and 200 mg emtricitabine. In certain embodiments, a choline salt of Compound 1, or crystalline form thereof, disclosed herein is combined with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, a choline salt of Compound 1, or crystalline form thereof, disclosed herein is combined with 10 mg tenofovir alafenamide fumarate, tenofovir alafenamide hemifumarate, or tenofovir alafenamide, and 200 mg emtricitabine. In certain embodiments, a choline salt of Compound 1, or crystalline form thereof, disclosed herein is combined with 25 mg tenofovir alafenamide fumarate, tenofovir alafenamide hemifumarate, or tenofovir alafenamide, and 200 mg emtricitabine. A choline salt of Compound 1, or crystalline form thereof, disclosed herein may be combined with the agents provided herein in any dosage amount of the salt or crystalline form (e.g., from 1 mg to 1000 mg of the salt or crystalline form) the same as if each combination of dosages were specifically and individually listed.

In certain embodiments, a choline salt of Compound 1, or crystalline form thereof, disclosed herein, is combined with 200-400 mg tenofovir disoproxil fumarate, tenofovir disoproxil hemifumarate, or tenofovir disoproxil, and 200 mg emtricitabine. In certain embodiments, a choline salt of Compound 1, or crystalline form thereof, disclosed herein is combined with 200-250, 200-300, 200-350, 250-350, 250-400, 350-400, 300-400, or 250-400 mg tenofovir disoproxil fumarate, tenofovir disoproxil hemifumarate, or tenofovir disoproxil, and 200 mg emtricitabine. In certain embodiments, a choline salt of Compound 1, or crystalline form thereof, disclosed herein is combined with 300 mg tenofovir disoproxil fumarate, tenofovir disoproxil hemifumarate, or tenofovir disoproxil, and 200 mg emtricitabine. A choline salt of Compound 1, or crystalline form thereof, disclosed herein may be combined with the agents provided herein in any dosage amount of the salt or crystalline form (e.g., from 1 mg to 1000 mg of the salt or crystalline form) the same as if each combination of dosages were specifically and individually listed.

In some embodiments, a choline salt of Compound 1, or crystalline form thereof, disclosed herein is combined with 20-80 mg of bictegravir or a choline salt thereof. A choline salt of Compound 1, or crystalline form thereof, disclosed herein may be combined with the agents provided herein in any dosage amount of the salt or crystalline form (e.g., from 1 mg to 1000 mg of the salt or crystalline form) the same as if each combination of dosages were specifically and individually listed.

In one embodiment, kits comprising a choline salt of Compound 1, or crystalline form thereof, disclosed herein in combination with one or more (e.g., one, two, three, one or two, or one to three) additional therapeutic agents are provided.

In some embodiments, kits comprising a choline salt of Compound 1, or crystalline form thereof, disclosed herein in combination with one or more (e.g., one, two, three, one or two, or one to three) additional therapeutic agents are provided.

Pharmaceutical Compositions

Pharmaceutical compositions disclosed herein comprise a choline salt of Compound 1, or crystalline form thereof, disclosed herein together with one or more pharmaceutically acceptable excipients and optionally other therapeutic agents. Pharmaceutical compositions containing the active ingredient may be in any form suitable for the intended method of administration.

In some embodiments, pharmaceutical compositions disclosed herein comprise a choline salt of Compound 1, or crystalline form thereof, disclosed herein together with one or more pharmaceutically acceptable excipients and optionally other therapeutic agents. Pharmaceutical compositions containing the active ingredient may be in any form suitable for the intended method of administration.

Pharmaceutical compositions comprising the choline salt of Compound 1, or crystalline form thereof, disclosed herein may be prepared with conventional carriers (e.g., inactive ingredient or excipient material) which may be selected in accord with ordinary practice. Tablets may contain excipients including glidants, fillers, binders and the like. Aqueous compositions may be prepared in sterile form, and when intended for delivery by other than oral administration generally may be isotonic. All compositions may optionally contain excipients such as those set forth in the Rowe et al, Handbook of Pharmaceutical Excipients, 5th edition, American Pharmacists Association, 1986. Excipients can include ascorbic acid and other antioxidants, chelating agents such as EDTA, carbohydrates such as dextrin, hydroxyalkylcellulose, hydroxyalkylmethylcellulose, stearic acid and the like.

While it is possible for the active ingredient to be administered alone, it may be preferable to present the active ingredient as pharmaceutical compositions. The compositions, both for veterinary and for human use, comprise at least the choline salt of Compound 1, or crystalline form thereof, disclosed herein together with one or more acceptable carriers and optionally other therapeutic ingredients. In one embodiment, the pharmaceutical composition comprises a choline salt of Compound 1, or crystalline form thereof, a pharmaceutically acceptable excipient, and a therapeutically effective amount of one or more (e.g., one, two, three, or four; or one or two; or one to three; or one to four) additional therapeutic agents as defined hereinbefore. In one embodiment, the pharmaceutical composition comprises a choline salt of Compound 1, or crystalline form thereof, a pharmaceutically acceptable excipient, and one other therapeutic ingredient. The carrier(s) are "acceptable" in the sense of being compatible with the other ingredients of the composition and physiologically innocuous to the recipient thereof.

The compositions include those suitable for various administration routes. The compositions may conveniently be presented in unit dosage form and may be prepared by any of the methods well known in the art of pharmacy. Such methods include the step of bringing into association the active ingredient with one or more inactive ingredients (e.g., a carrier, pharmaceutical excipient, etc.). The compositions may be prepared by uniformly and intimately bringing into association the active ingredient with liquid carriers or finely divided solid carriers or both, and then, if necessary, shaping the product. Techniques and formulations generally are found in Remington: The Science and Practice of Pharmacy, 21$^{st}$ Edition, Lippincott Wiliams and Wilkins, Philadelphia, Pa., 2006.

Compositions described herein that are suitable for oral administration may be presented as discrete units (a unit dosage form) including but not limited to capsules, cachets or tablets each containing a predetermined amount of the active ingredient.

When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

In some embodiments, disclosed herein are oral dosage forms (e.g., tablets), which may be prepared from hot melt extrusion or spray-drying dispersion (SDD) technologies.

In some embodiments, disclosed herein are hard capsules filled with powder, beads, or granules containing the active ingredient in admixture with non-toxic pharmaceutically acceptable excipient which are suitable for manufacture of hard or soft capsules. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc.

In some embodiments, disclosed herein are hard or soft capsules filled with liquid or semi-solid mixtures containing the active ingredient in admixture with non-toxic pharmaceutically acceptable excipient which are suitable for manufacture of hard or soft capsules. These excipients may be, for example, solubilizing oils such as maize oil, sesame oil, or corn oil; medium chain triglycerides and related esters, such as, derivitized palm kernel oil or coconut oil; self-emulsifying lipid systems (SEDDS or SMEDDS), such as caprylic triglyceride or propylene glycol monocaprylate; viscosity modifiers, such as, cetyl alcohol, steryl alcohol, glycerol stearate; and solubilizing agents and surfactants, such as polyethylene glycol, propylene glycol, glycerin, ethanol, polyethoxylated castor oil, poloxamers, or polysorbates.

The pharmaceutical compositions of the present disclosure may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3- butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

In some embodiments, the sterile injectable preparation disclosed herein may also be a sterile injectable solution or suspension prepared from a reconstituted lyophilized powder in a non-toxic parenterally acceptable diluent or solvent, such as a solution in 1,3-butane-diol. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. In certain embodiments the suspension is a microsuspension. In certain embodiments the suspension is a nanosuspension.

In some embodiments, formulations suitable for parenteral administration (e.g., intramuscular (IM) and subcutaneous (SC) administration) will include one or more excipients. Excipients should be compatible with the other ingredients of the formulation and physiologically innocuous to the recipient thereof. Examples of suitable excipients are well known to the person skilled in the art of parenteral formulation and may be found e.g., in Handbook of Pharmaceutical Excipients (eds. Rowe, Sheskey & Quinn), 6th edition 2009.

Examples of solubilizing excipients in a parenteral formulation (e.g., an SC or IM formulation) include, but are not limited to, polysorbates (such as polysorbate 20 or 80) and poloxamers (such as poloxamer 338, 188, or 207). In some embodiments, disclosed herein is a parenteral administration (e.g., an SC or IM formulation) that comprises a choline salt of Compound 1, or crystalline form thereof, disclosed herein and a poloxamer, in particular poloxamer 338. In some embodiments, the amount of poloxamer (e.g., poloxamer 388) in a parenteral administration disclosed herein is less than about 5%, such as less than about 3%, about 2%, about 1%, or about 0.5%.

In some embodiments, the parenteral formulation (e.g., an SC or IM formulation) disclosed herein is an aqueous suspension. In some embodiments, the parenteral formulation (e.g., an SC or IM formulation) disclosed herein is an aqueous suspension that comprises a choline salt of Compound 1, or crystalline form thereof, disclosed herein and saline. In some embodiments, the parenteral formulation (e.g., an SC or IM formulation) disclosed herein is an aqueous suspension that comprises a choline salt of Compound 1, or crystalline form thereof, disclosed herein saline, and a poloxamer (such as poloxamer 338, 188, or 207).

In certain embodiments, the composition is disclosed as a solid dosage form, including a solid injectable dosage form, such as a solid depot form.

The amount of active ingredient that may be combined with the inactive ingredients to produce a dosage form may vary depending upon the intended treatment subject and the particular mode of administration. For example, in some embodiments, a dosage form for oral administration to humans may contain approximately 1 to 1000 mg of active material formulated with an appropriate and convenient amount of carrier material (e.g., inactive ingredient or excipient material). In certain embodiments, the carrier material varies from about 5 to about 95% of the total compositions (weight:weight).

It should be understood that in addition to the ingredients particularly mentioned above the compositions of these embodiments may include other agents conventional in the art having regard to the type of composition in question, for example those suitable for oral administration may include flavoring agents.

In certain embodiments, a composition comprising an active ingredient disclosed herein in one variation does not contain an agent that affects the rate at which the active ingredient is metabolized. Thus, it is understood that compositions comprising a choline salt of Compound 1, or crystalline form thereof, in certain embodiments do not comprise an agent that would affect (e.g., slow, hinder or retard) the metabolism of the choline salt of Compound 1, or crystalline form thereof, or any other active ingredient administered separately, sequentially or simultaneously with the salt or crystalline form. It is also understood that any of the methods, kits, articles of manufacture and the like detailed herein in certain embodiments do not comprise an agent that would affect (e.g., slow, hinder or retard) the metabolism of a choline salt of Compound 1, or crystalline form thereof, or any other active ingredient administered separately, sequentially or simultaneously with the choline salt of Compound 1, or crystalline form thereof.

Kits and Articles of Manufacture

The present disclosure relates to a kit comprising a choline salt of Compound 1, or crystalline form thereof, disclosed herein. In one embodiment, the kit may comprise one or more additional therapeutic agents as described hereinbefore. The kit may further comprise instructions for use, e.g., for use in inhibiting an HIV reverse transcriptase, such as for use in treating an HIV infection or AIDS or as a research tool. The instructions for use are generally written instructions, although electronic storage media (e.g., magnetic diskette or optical disk) containing instructions are also acceptable.

The present disclosure also relates to a pharmaceutical kit comprising one or more containers comprising a choline salt of Compound 1, or crystalline form thereof, disclosed herein. Optionally associated with such container(s) can be a notice in the form prescribed by a governmental agency regulating the manufacture, use or sale of pharmaceuticals, which notice reflects approval by the agency for the manufacture, use or sale for human administration. Each component (if there is more than one component) can be packaged in separate containers or some components can be combined in one container where cross-reactivity and shelf life permit. The kits may be in unit dosage forms, bulk packages (e.g., multi-dose packages) or sub-unit doses. Kits may also include multiple unit doses of the compounds and instructions for use and be packaged in quantities sufficient for storage and use in pharmacies (e.g., hospital pharmacies and compounding pharmacies).

In some embodiments, the present disclosure also relates to a pharmaceutical kit comprising one or more containers comprising a choline salt of Compound 1, or crystalline form thereof, disclosed herein. Optionally associated with such container(s) can be a notice in the form prescribed by a governmental agency regulating the manufacture, use or sale of pharmaceuticals, which notice reflects approval by the agency for the manufacture, use or sale for human administration. Each component (if there is more than one component) can be packaged in separate containers or some components can be combined in one container where cross-reactivity and shelf life permit. The kits may be in unit dosage forms, bulk packages (e.g., multi-dose packages) or sub-unit doses. Kits may also include multiple unit doses of the compounds and instructions for use and be packaged in quantities sufficient for storage and use in pharmacies (e.g., hospital pharmacies and compounding pharmacies).

Also disclosed are articles of manufacture comprising a unit dosage of a choline salt of Compound 1, or crystalline form thereof, disclosed herein in suitable packaging for use in the methods described herein. Suitable packaging is known in the art and includes, for example, vials, vessels, ampules, bottles, jars, flexible packaging and the like. An article of manufacture may further be sterilized and/or sealed.

EXAMPLES

General Methods
X-Ray Powder Diffraction (XRPD)
XRPD patterns were collected on a PANanalytical XPERT-PRO diffractometer at ambient conditions under the following experimental settings: 45 KV, 40 mA, Kα1=1.5406 Å, scan range 2 to 40°, step size 0.0084 or 0.0167°, measurement time: 5 min.
Differential Scanning Calorimetry (DSC)
DSC thermograms were collected on a TA Instruments Q2000 system equipped with a 50 position auto-sampler. The calibration for energy and temperature was carried out using certified indium. Typically 1-5 mg of each sample, in a pin-holed aluminium pan, was heated at 10° C./min from 25° C. to 300° C. A purge of dry nitrogen at 50 mL/min was maintained over the sample throughout the measurement. The onset of the melting endotherm was reported as the melting point.
Proton Nuclear Magnetic Resonance ($^1$H NMR)
$^1$H NMR spectra were collected on a Varian 400-MR 400 MHz instrument with 7620AS sample changer. The default proton parameters are as follows: spectral width: 14 to −2 ppm (6397.4 Hz); relaxation delay: 1 sec; pulse: 45 degrees; acquisition time: 2.049 sec; number of scans or repetitions: 8; temperature: 25° C. Samples were prepared in dimethyl sulfoxide-d6, unless otherwise stated. Off-line analysis was carried out using MestReNova software.

Intermediate 1. tert-Butyl (S)-(1-(3,6-dibromopyridin-2-yl)-2-(3,5-difluorophenyl)ethyl)carbamate

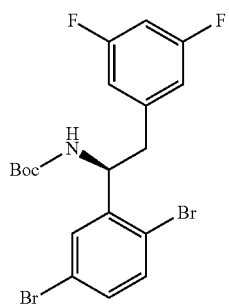 [SMILES: CC(C)(C)OC(=O)N[C@@H](Cc1cc(F)cc(F)c1)c1cc(Br)ccc1Br]

Step 1. (S)—N-((3,6-Dibromopyridin-2-yl)methylene)-2-methylpropane-2-sulfinamide

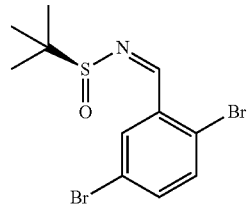 [SMILES: CC(C)(C)[S@](=O)/N=C\c1cc(Br)ccc1Br]

3,6-Dibromopicolinaldehyde (76.0 g, 0.287 mol) and (S)-2-methylpropane-2-sulfinamide (36.51 g, 0.301 mol) were combined in NMP (N-methyl-2-pyrrolidone) (200 mL). To the reaction mixture was added $Cs_2CO_3$ (41.94 g, 0.316 mol) as a solid in one portion. The reaction mixture was stirred for about 2 h then cooled to about 5° C. Water (1.3 L) was added to the reaction mixture. The resulting suspension was stirred for about 1 h, solids isolated by filtration, washed with water (5×100 mL) and dried to provide the title compound. MS (m/z) 368.9 [M+H]$^+$.

Step 2. (S)—N—((S)-1-(3,6-Dibromopyridin-2-yl)-2-(3,5-difluorophenyl)ethyl)-2-methylpropane-2-sulfinamide

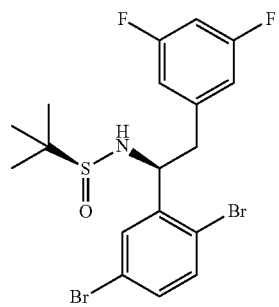 [SMILES: CC(C)(C)[S@](=O)N[C@@H](Cc1cc(F)cc(F)c1)c1cc(Br)ccc1Br]

A reaction vessel was charged with (S)—N-((3,6-dibromopyridin-2-yl)methylene)-2-methylpropane-2-sulfinamide (65.5 g, 177.95 mmol) followed by DMF (dimethylformamide) (260 mL). The mixture was stirred for about 5 min until homogeneous and the solution was cooled to about 8° C. To the reaction mixture was added (3,5-difluorobenzyl) zinc bromide (0.5 M in tetrahydrofuran (THF), 516.04 mL) dropwise over about 90 mins. The mixture was stirred for about an additional 2.5 h. To the reaction mixture, 5% AcOH (acetic acid) in water (640 mL) was added over about 10 mins followed by CPME (cyclopentyl methyl ether) (320 mL) in one portion. The mixture was stirred for about 5 mins, warmed to room temperature, and the layers were separated. The organic layer was washed with 5% AcOH (320 mL) then treated with 0.5M NaOH (330 mL) and washed with brine. The organic layer was collected, dried with $Na_2SO_4$, and filtered. To the crude mixture was added MeOH (methanol) (33 mL). To the stirring mixture was added dropwise 3M HCl in CPME (128 mL) over about 15 mins. After stirring for about 1 h, the precipitate was removed by filtration. The filtrate was diluted with hexane (300 mL) and the product was extracted with water (450 mL). The aqueous layer was basified with 8M NaOH and extracted with CPME (375 mL). The organic layer was washed with brine, dried over $Na_2SO_4$ and filtered to provide the title compound in solution which was used directly in the next reaction. MS (m/z) 497.0 $[M+H]^+$.

Step 3. (S)-1-(3,6-dibromopyridin-2-yl)-2-(3,5-difluorophenyl)ethan-1-amine

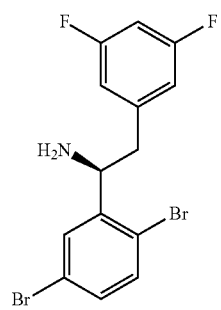 [SMILES: N[C@@H](Cc1cc(F)cc(F)c1)c1cc(Br)ccc1Br]

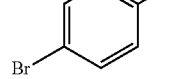

The resulting solution of (S)—N—((S)-1-(3,6-dibromopyridin-2-yl)-2-(3,5-difluorophenyl)ethyl)-2-methylpropane-2-sulfinamide was diluted with CPME to a volume of 700 mL to which acetonitrile (350 mL) was added. To the stirring mixture, concentrated HCl (37%, 16.4 mL) was added dropwise over about 10 mins at room temperature. The thick slurry was vigorously stirred for about 4 h. The solids were filtered and washed with 2:1 CPME (cyclopropyl methyl ether):ACN to provide the title compound. MS (m/z) 393.3 $[M+H]^+$.

Step 4. tert-Butyl (S)-(1-(3,6-dibromopyridin-2-yl)-2-(3,5-difluorophenyl)ethyl)carbamate A reaction vessel was charged with 2-MeTHF (2-methyltetrahydrofuran) (190 mL), water (190 mL) and (S)-1-(3,6-dibromopyridin-2-yl)-2-(3,5-difluorophenyl)ethan-1-amine (46.9 g, 0.11 mol) followed by portionwise addition of $NaHCO_3$ (30.34 g, 0.36 mol). The reaction mixture was cooled to about 5° C. and di-tert-butyl dicarbonate (27.47 g, 0.13 mol) was added. The reaction mixture was stirred at about 0° C. for about 2 h and ambient temperature for about 2 h. The reaction mixture was diluted with water and extracted with MTBE (methyl tert-butyl ether). The organic layers were washed with brine, dried and concentrated. Crude compound was purified by column chromatography on silica to provide the title compound. MS (m/z) 492.8 $[M+H]^+$. $^1$H NMR (400 MHz, Methanol-$d_4$) δ 7.85 (d, 1H), 7.42 (d, 1H), 6.90-6.72 (m, 3H), 5.33 (dd, 1H), 3.10 (dd, 1H), 2.92 (dd, 1H), 1.36 (s, 9H).

Intermediate 2. 4-Chloro-7-(4,4,5,5-tetramethyl-1,3,2-dioxaborolan-2-yl)-1-(2,2,2-trifluoroethyl)-1H-indazol-3-amine

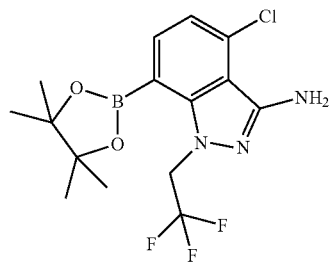 [SMILES: CC1(C)OB(c2ccc(Cl)c3c(N)nn(CC(F)(F)F)c23)OC1(C)C]

Step 1. 7-Bromo-4-chloro-1H-indazol-3-amine

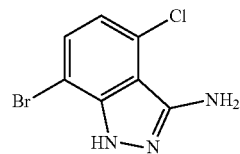 [SMILES: Nc1n[nH]c2c(Br)ccc(Cl)c12]

To 3-bromo-6-chloro-2-fluorobenzonitrile (13.9 g, 59.3 mmol) in EtOH (ethanol) (60 mL) was added hydrazine monohydrate (5.77 mL). The reaction mixture was heated to about 80° C. for about 3 h. After cooling to ambient temperature, EtOH (20 mL) was added to allow for stirring. The solids were isolated by filtration, washed with cold EtOH, and dried to provide the title compound. MS (m/z) 247.9 $[M+H]^+$.

Step 2. 7-Bromo-4-chloro-1-(2,2,2-trifluoroethyl)-1H-indazol-3-amine

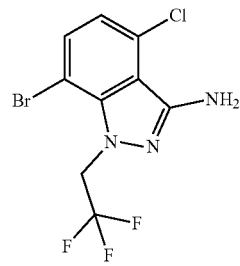 [SMILES: Nc1nn(CC(F)(F)F)c2c(Br)ccc(Cl)c12]

A reactor was charged with 7-bromo-4-chloro-1H-indazol-3-amine (397.2 g, 1.6 mol) and $Cs_2CO_3$ (1052 g, 3.2 mol) then diluted with DMF (dimethylformamide) (4000 mL). To this was slowly added 2,2,2-trifluoroethyl trifluoromethanesulfonate (463.2 g, 1.9 mol) via addition funnel. Upon completion of the addition, the reaction mixture was allowed to stir for about 1 hour, at which time, $H_2O$ (16 L) was added slowly. Upon completion of the addition, the mixture was allowed to stir for about 12 hours at about 15° C. The slurry was filtered and the collected solids were suspended in DMF (800 mL). To this was added $H_2O$ (4800 mL) and the resulting solids were collected by filtration and dried to provide the title compound. MS (m/z) 330.1 [M+H]⁺.

Step 3. 4-Chloro-7-(4,4,5,5-tetramethyl-1,3,2-dioxaborolan-2-yl)-1-(2,2,2-trifluoroethyl)-1H-indazol-3-amine A reaction vessel was charged with 7-bromo-4-chloro-1-(2,2,2-trifluoroethyl)-1H-indazol-3-amine (15.00 g, 45.66 mmol), bis(pinacolato)diboron (17.39 g, 68.49 mmol), potassium propionate (15.36 g, 136.98 mmol), dioxane (90 mL) and DMF (dimethylformamide) (30 mL). Bis(triphenylphosphine)palladium(II) dichloride (0.64 g, 0.91 mmol) was added and the reaction solution degassed by bubbling argon for about 2 min. The reaction mixture was heated to about 105° C. for about 4 hrs. After cooling to ambient temperature, the reaction mixture was filtered through a pad of Celite and silica gel washing with EtOAc. The filtrate was washed with 5% LiCl solution and brine. The organic layers were separated, dried, and concentrated under reduced pressure. The residue was treated with IPAc/heptane (1/10) at about 60° C. then cooled to ambient temperature and stirred for about 15 h. The solids were collected by filtration and dried to afford the title compound. MS (m/z) 376.7 [M+H]⁺ ¹H NMR (400 MHz, DMSO-d₆) δ 7.69 (d, 1H), 7.06 (d, 1H), 5.55 (s, 2H), 5.45 (q, 2H), 1.32 (s, 12H).

Intermediate 3. 2-((3bS,4aR)-5,5-Difluoro-3-(trifluoromethyl)-3b,4,4a,5-tetrahydro-1H-cyclopropa[3,4]cyclopenta[1,2-c]pyrazol-1-yl)acetic acid

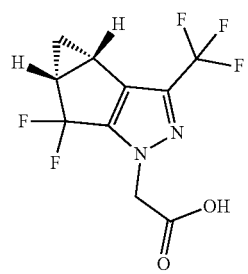 [SMILES: O=C(O)Cn1nc(C(F)(F)F)c2c1C(F)(F)[C@@H]1C[C@H]21]

Step 1. Lithium 2,2,2-trifluoro-1-(3-oxobicyclo[3.1.0]hexan-2-ylidene)ethan-1-olate

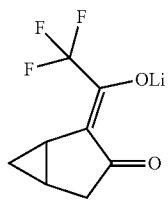

A reactor was charged with bicyclo[3.1.0]hexan-3-one (95.6 g, 0.99 mol) and ethyl 2,2,2-trifluoroacetate (113.2 mL, 0.95 mol) and THF (50 mL). The reaction mixture was cooled to about 0° C. LiHMDS (Lithium bis(trimethylsilyl)amide) (1 L of 1.0M solution in THF, 1 mol) was added via an addition funnel at a rate to maintain internal temperature at below about 1° C. After the addition was complete, hexanes (235 mL) was added in a steady stream via an addition funnel and stirred for about 15 min. The resultant solids were collected by filtration, washed with hexanes (3×400 mL), and dried to provide the title compound.

Step 2. Ethyl 2-(3-(trifluoromethyl)-3b,4,4a,5-tetrahydro-1H-cyclopropa[3,4]cyclopenta[1,2-c]pyrazol-1-yl)acetate

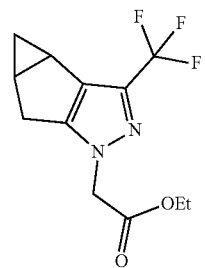 [SMILES: CCOC(=O)Cn1nc(C(F)(F)F)c2c1CC1CC21]

A reactor was charged with lithium 2,2,2-trifluoro-1-(3-oxobicyclo[3.1.0]hexan-2-ylidene)ethan-1-olate (177.2 g, 0.89 mol) and EtOH (ethanol) (779 mL). The temperature was brought to and maintained at about 0° C. HCl in dioxane (4.0 N, 443 mL) was added via an addition funnel followed by the addition of solid ethyl hydrazinoacetate HCl salt (138.4 g, 0.90 mol). The reaction temperature was adjusted to about 35° C. After about 1 h, the reaction volume was reduced by ~40% by distillation at reduced pressure. Water (1.3 L) was added with vigorous agitation and temperature adjusted to about 15° C. The resultant solids were collected by filtration, washed with water (3×500 mL), hexanes (3×400 mL), and dried to provide the title compound. MS (m/z) 275.1 [M+H]⁺.

Step 3. Ethyl 2-(5-oxo-3-(trifluoromethyl)-3b,4,4a,5-tetrahydro-1H-cyclopropa[3,4]cyclopenta[1,2-c]pyrazol-1-yl)acetate

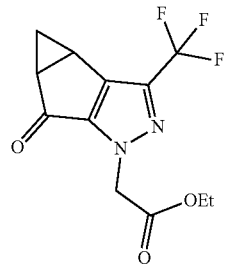 [SMILES: O=C(O)Cn1nc(C(F)(F)F)c2c1C(=O)C1CC21]

A reactor was charged with ethyl 2-(3-(trifluoromethyl)-3b,4,4a,5-tetrahydro-1H-cyclopropa[3,4]cyclopenta[1,2-c]pyrazol-1-yl)acetate (291.2 g, 1.06 mol), I (acetonitrile) (1.65 L) and water (825 mL) to which N-hydroxyphthalimide (17.4 g, 0.103 mol) and NaClO₂ (41.0 g, 0.45 mol, ~20% of total amount to be added) were added. The reaction mixture was heated to about 50° C. and the remaining NaClO₂ (163.0 g, 1.80 mol) was added in five portions over about 2 h. After consumption of starting material, the temperature was adjusted to about 20° C. and aqueous sodium bisulfite (40% w/w, 350 mL) was added via an addition funnel. Ethyl acetate (1.75 L) was added and the layers were separated. The aqueous layer was back extracted with EtOAc (ethyl acetate) (500 mL). The organic layers were combined and washed with saturated aqueous NaHCO₃ (500 mL) and 1:1 water/brine (500 mL). The organic layer was concentrated under reduced pressure and co-evaporated with IPAc (isopropyl acetate) (300 mL). The crude solid was crystallized from a mixture of IPAc/heptane. The resultant solids were collected by filtration, washed with heptane, and dried to provide the title compound. MS (m/z) 289.0 [M+H]⁺.

Step 4. 2-(5-Oxo-3-(trifluoromethyl)-3b,4,4a,5-tetrahydro-1H-cyclopropa[3,4]cyclopenta[1,2-c]pyrazol-1-yl)acetic acid

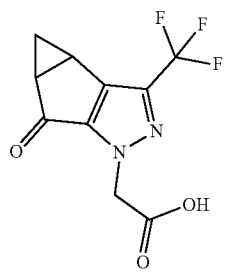

To a solution of ethyl 2-(5-oxo-3-(trifluoromethyl)-3b,4,4a,5-tetrahydro-1H-cyclopropa[3,4]cyclopenta[1,2-c]pyrazol-1-yl)acetate (80.40 g, 278.95 mmol) in 2-MeTHF (167 mL) was added 2M aqueous sodium hydroxide (167 mL). After about 25 minutes of stirring at room temperature, the reaction mixture was diluted with 2-MeTHF and was slowly acidified by the dropwise addition of concentrated HCl. The organic layer was isolated and the aqueous layer was extracted with an additional portion of 2-MeTHF. The combined organic layers were washed with saturated aqueous sodium chloride, then dried over sodium sulfate, filtered, and concentrated. The resulting oil was taken in ethyl acetate. Hexanes was added with vigorous stirring until solid formation was observed. The solid was isolated by filtration and dried to provide the title compound. MS (m/z) 259.00 [M–H]⁻.

Step 5. 2-(3-(Trifluoromethyl)-4,4a-dihydrospiro [cyclopropa[3,4]cyclopenta[1,2-c]pyrazole-5,2'-[1,3] dithiolane]-1(3bH)-yl)acetic acid

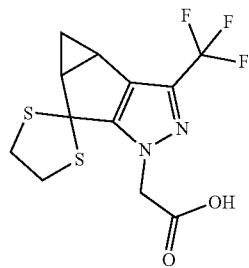 [SMILES: O=C(O)Cn1nc(C(F)(F)F)c2c1C1(SCCS1)C1CC21]

To a solution of 2-(5-oxo-3-(trifluoromethyl)-3b,4,4a,5-tetrahydro-1H-cyclopropa[3,4]cyclopenta[1,2-c]pyrazol-1-yl)acetic acid (3.0 g, 11.5 mmol) in DCM (dichloromethane) (25 mL) was added 1,2-ethanedithiol (1.07 mL, 12.68 mmol) followed by boron trifluoride-acetic acid complex (4.0 mL, 28.8 mmol). The reaction mixture was stirred at room temperature overnight. To the reaction mixture was added water (60 mL) and 2-MeTHF (60 mL). The organic layer was isolated, dried over sodium sulfate, filtered, and concentrated. The crude was dissolved in ethyl acetate (2 mL) and the solution diluted with hexanes (12 mL) with vigorous stirring to provide a solid. The solid was isolated by filtration and dried to provide the title compound. MS (m/z) 337.12 [M+H]⁺.

Step 6. 2-(5,5-Difluoro-3-(trifluoromethyl)-3b,4,4a, 5-tetrahydro-1H-cyclopropa[3,4]cyclopenta[1,2-c] pyrazol-1-yl)acetic acid

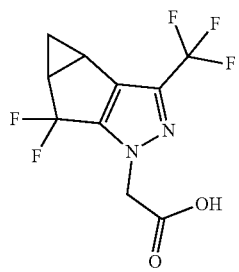 [SMILES: O=C(O)Cn1nc(C(F)(F)F)c2c1C(F)(F)C1CC21]

To a suspension of 1,3-dibromo-5,5-dimethylhydantoin (12.75 g, 44.6 mmol) in DCM (35 mL) was added pyridine hydrofluoride (5.0 mL) at about 0° C. The suspension was stirred at about 0° C. for about 10 minutes. To the suspension was added a solution of 2-(3-(trifluoromethyl)-4,4a-dihydrospiro[cyclopropa[3,4]cyclopenta[1,2-c]pyrazole-5,2'-[1,3]dithiolane]-1(3bH)-yl)acetic acid (5.00 g, 14.9 mmol) dropwise. After addition was complete, the reaction mixture was stirred at about 0° C. for about an additional 15 minutes. The reaction mixture was poured into saturated aqueous sodium bicarbonate solution (300 mL) with vigorous stirring. The organic layer was removed and the aqueous layer was acidified to pH ~1 with concentrated HCl. The aqueous phase was extracted with three portions of MTBE (methyl tert-butyl ether). The combined organic layers were dried over sodium sulfate, filtered, and concentrated. The resulting solid was taken in MTBE (16 mL) and filtered to remove any resulting solid. The solution was then extracted with 2N NaOH (16 mL). The aqueous layer was diluted with water (16 mL) with vigorous stirred and stirred at room temperature for about 15 minutes. The resulting solid was removed by filtration. The aqueous layer was acidified by slow, dropwise addition of concentrated HCl to pH ~1 with vigorous stirring to provide a solid precipitate. The solid was isolated by filtration to provide the title compound. MS (m/z) 281.12 [M+H]⁺.

Step 7. 2-((3bS,4aR)-5,5-Difluoro-3-(trifluoromethyl)-3b,4,4a,5-tetrahydro-1H-cyclopropa[3,4]cyclopenta[1,2-c]pyrazol-1-yl)acetic acid 2-(5,5-Difluoro-3-(trifluoromethyl)-3b,4,4a,5-tetrahydro-1H-cyclopropa[3,4]cyclopenta[1,2-c]pyrazol-1-yl)acetic acid was separated to its constituent enantiomers (2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (Intermediate 3) and 2-((3bR,4aS)-5,5-difluoro-3-(trifluoromethyl)-3b,4,4a,5-tetrahydro-1H-cyclopropa[3,4]cyclopenta[1,2-c]pyrazol-1-yl)acetic acid), by chiral supercritical fluid chromatography (SFC) under the following conditions: Instrument: Thar 350 preparative SFC; Column: ChiralPak IC-10 u, 300×50 mmI.D; Mobile phase: 35% Isopropanol (0.1% $NH_3.H_2O$) and $CO_2$; Flow rate: 200 mL/min; Column temperature: 38° C.; UV detection: 220 nm; Sample preparation: Compound was dissolved in isopropanol to ~45 mg/mL; Injection: 6.5 mL per injection. Analytical SFC [mobile phase: A for $CO_2$ and B for Isopropanol (0.05% DEA); Gradient: B 20%; A; Flow rate: 2.35 mL/min; Column: Chiralpak IC-3, 150×4.6 mm, 3 μm; Wavelength: 254 nm]. The desired isomer, 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid, eluted at t=3.39 min; $^1$H NMR (400 MHz, Chloroform-d) δ 4.93 (s, 2H), 2.52-2.43 (m, 2H), 1.44-1.38 (m, 1H), 1.15 (m, 1H).

Intermediate 4:
3-methyl-3-(methylsulfonyl)but-1-yne

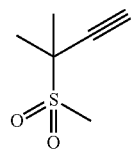

To a stirred suspension of sodium methanesulfinate (18.47 g, 175.5 mmol) and copper(I) chloride (1.45 g, 14.6 mmol) in DMF (dimethylformamide) (50 mL) was added 3-chloro-3-methylbut-1-yne (15.00 g, 146.3 mmol, 16.4 mL) dropwise. The resulting reaction mixture was heated to about 40° C. and stirred for about 16 h. The reaction mixture was cooled to room temperature and diluted with EtOAc. The solution was washed with water and brine. The organic layer was collected and dried over sodium sulfate, then filtered. The solution was concentrated under vacuum and purified by silica gel chromatography to provide the title compound. Mp: 114.8-115.5° C. $^1$H NMR (400 MHz, Chloroform-d) δ 3.04 (s, 3H), 2.58 (s, 1H), 1.67 (s, 6H).

Example 1. N—((S)-1-(3-(4-Chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-03bS,4aR)-5,5-difluoro-3-(trifluoromethyl)-3b,4,4a,5-tetrahydro-M-cyclopropa[3,4]cyclopenta[1,2-c]pyrazol-1-yl)acetamide (Compound 1)

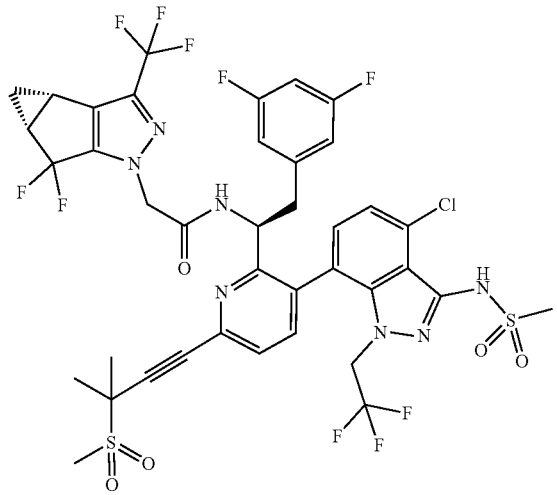 [SMILES: CC(C)(C#Cc1ccc(-c2ccc(Cl)c3c(NS(C)(=O)=O)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(C)(=O)=O]

Step 1. tert-Butyl (S)-(1-(3-bromo-6-(3-methyl-3-(methylsulfonyl)but-1-yn-1-yl)pyridin-2-yl)-2-(3,5-difluorophenyl)ethyl)carbamate

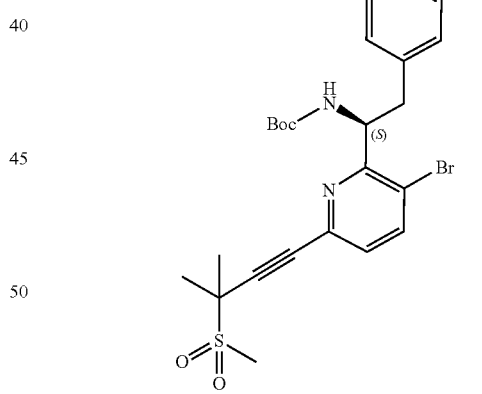

A reactor was charged with tert-butyl (S)-(1-(3,6-dibromopyridin-2-yl)-2-(3,5-difluorophenyl)ethyl)carbamate (Intermediate 1, 50.00 g, 101.8 mmol), 3-methyl-3-methylsulfonyl-but-1-yne (17.86 g, 122.2 mmol), DMF (dimethylformamide) (90 mL) and Et$_3$N (trimethylamine) (42.5 mL, 305.4 mmol). The reaction mixture was heated to about 50° C. Bis(triphenylphosphine)palladium(II) dichloride (2.14 g, 3.1 mmol) and copper(I) iodide (0.58 g, 3.1 mmol) were added. After about 30 min, the reaction mixture was diluted with MeCN (acetonitrile) (200 mL) and then 7% aq. NH$_4$Cl (200 mL) was added dropwise. A slurry was formed and adjusted to ambient temperature. After about 3 h, the solids were collected by filtration. The cake was washed with MeCN/water (1:1, 75 mL) twice and MTBE (methyl tert-butyl ether) (75 mL). The solid was dried to provide the title compound. MS (m/z) 556 [M+H]$^+$. $^1$H NMR (400 MHz, Chloroform-d) δ 7.84 (d, J=8.2 Hz, 1H), 7.29-7.15 (m, 1H), 6.70-6.55 (m, 2H), 5.79 (d, J=9.0 Hz, 1H), 5.57-5.45 (m, 1H), 3.21-3.05 (m, 4H), 2.99-2.88 (m, 1H), 1.80 (s, 6H), 1.40* (s, 7H), 1.30* (s, 2H). *denotes presence of atropisomers in 4.6:1 ratio.

Step 2. tert-Butyl (S)-(1-(3-(3-amino-4-chloro-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)carbamate

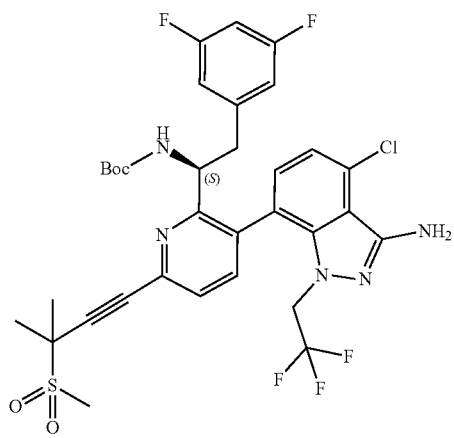

tert-Butyl (S)-(1-(3-bromo-6-(3-methyl-3-(methylsulfonyl)but-1-yn-1-yl)pyridin-2-yl)-2-(3,5-difluorophenyl)ethyl)carbamate (1000.0 mg, 1.79 mmol), 4-chloro-7-(4,4,5,5-tetramethyl-1,3,2-dioxaborolan-2-yl)-1-(2,2,2-trifluoroethyl)-1H-indazol-3-amine (808.5 mg, 2.15 mmol), [1,1'-bis(diphenylphosphino)ferrocene]dichloropalladium(II) (65.6 mg, 0.09 mmol), and cesium carbonate (876.7 mg, 2.69 mmol) were charged in a round bottom flask and placed under argon. Dioxane (10 mL) and water (2 mL) were added, and the suspension was degassed by bubbling argon for about one minute. After degassing, the reaction flask was fitted with a reflux condenser and heated to about 80° C. for overnight. The reaction mixture was cooled to room temperature, and the aqueous layer was removed. The organic layer was concentrated under vacuum, and the resulting residue was purified by silica gel column chromatography to provide the title compound. MS (m/z) 726.1 [M+H]$^+$. $^1$H NMR (400 MHz, Chloroform-d) δ 7.69-7.55 (m), 7.55-7.42 (m), 7.16-7.06 (m), 7.07-6.96 (m), 6.89 (d), 6.60 (tt), 6.44 (dd), 6.20 (d), 6.16 (d), 6.08 (s), 5.69-5.53 (m), 5.29 (s), 5.26 (d), 4.95-4.85 (m), 4.64 (q), 4.59-4.46 (m), 4.36-4.19 (m), 3.94-3.76 (m), 3.64-3.54 (m), 3.18 (s), 3.17 (s), 3.01-2.84 (m), 2.78-2.68 (m), 1.86-1.82 (m), 1.38 (s), 1.34 (s), 1.26 (s), 1.23 (s), 1.15 (s).

Step 3. tert-Butyl (S)-(1-(3-(4-chloro-3-(N-(methylsulfonyl)methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)carbamate

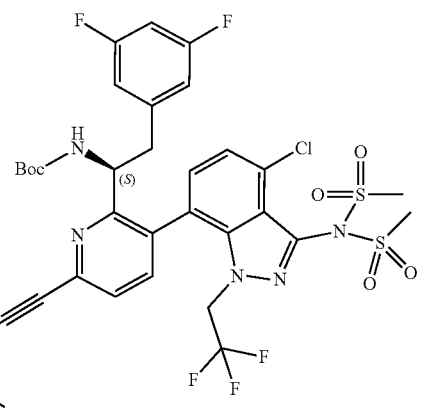

tert-Butyl (S)-(1-(3-(3-amino-4-chloro-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)carbamate (37.89 g, 52.18 mmol) was dissolved in methylene chloride (380 mL) with stirring at ambient temperature. To it was added triethylamine (21.82 mL, 156.54 mmol) followed by slow addition of methanesulfonyl chloride (8.08 mL, 104.36 mmol). When the reaction was complete, water (200 mL) was added and stirred for about 0.5 hours. The organic layer was separated and the aqueous layer was extracted with methylene chloride once. The combined organic layers were washed with water and brine, dried over MgSO$_4$, filtered and concentrated to a small volume. Hexanes was added. The liquid suspension was decanted. The remaining solid was dried under reduced pressure to afford the title compound. MS (m/z): 882.69 [M+H]$^+$. $^1$H NMR (400 MHz, Methanol-d$_4$) δ 7.87 (d), 7.83 (d), 7.76 (s), 7.74 (s), 7.69 (s), 7.67 (s), 7.65 (s), 7.52-7.47 (m), 7.46 (s), 7.37 (d), 7.33 (d), 7.11-7.03 (m), 4.79-4.55 (m), 4.51 (t), 4.36 (dt), 4.20-4.05 (m), 3.64 (s), 3.62 (s), 3.60 (s), 3.59 (s), 3.23 (s), 3.04 (d), 3.01 (d), 2.95-2.83 (m), 1.81 (s), 1.34 (s), 1.29 (s), 0.98 (s).

Step 4. (S)—N-(7-(2-(1-Amino-2-(3,5-difluorophenyl)ethyl)-6-(3-methyl-3-(methylsulfonyl)but-1-yn-1-yl)pyridin-3-yl)-4-chloro-1-(2,2,2-trifluoroethyl)-1H-indazol-3-yl)-N-(methylsulfonyl)methanesulfonamide

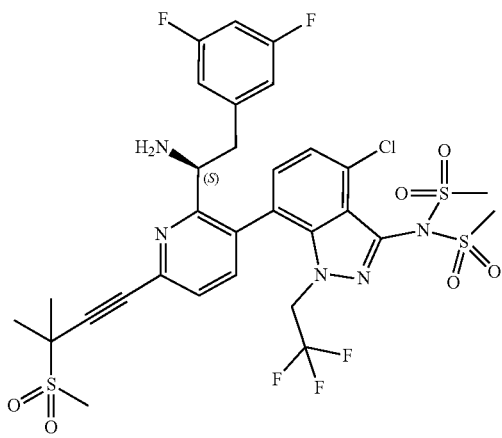

To tert-Butyl (S)-(1-(3-(4-chloro-3-(N-(methylsulfonyl)methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)carbamate (39 g, 44 mmol) dissolved in methylene chloride (120 mL) was added trifluoroacetic acid (80 mL). The reaction mixture was stirred at ambient temperature for about 50 minutes. The reaction mixture was diluted with methylene chloride and slowly poured into ice cold saturated aqueous NaHCO$_3$. The organic layer was separated, washed with water and brine, dried over MgSO$_4$, filtered and concentrated to dryness to afford the title compound. MS (m/z): 782.84 [M+H]$^+$. $^1$H NMR (400 MHz, Chloroform-d) δ 7.61 (d), 7.54-7.44 (m), 7.40 (d), 7.33 (d), 7.20 (d), 6.66-6.57 (m), 6.44 (d), 6.33 (d), 6.17 (d), 4.64 (s), 3.68 (s), 3.64 (s), 3.61 (s), 3.55 (s), 3.19 (s), 3.05 (dd), 2.85-2.72 (m), 1.86 (s), 1.62 (s).

Step 5. N—((S)-1-(3-(4-Chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (S)—N-(7-(2-(1-Amino-2-(3,5-difluorophenyl)ethyl)-6-(3-methyl-3-(methylsulfonyl)but-1-yn-1-yl)pyridin-3-yl)-4-chloro-1-(2,2,2-trifluoroethyl)-1H-indazol-3-yl)-N-(methylsulfonyl)methanesulfonamide (1757 mg, 2.25 mmol), 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (Intermediate 3, 666 mg, 2.36 mmol), and HATU (1-[bis(dimethylamino)methylene]-1H-1,2,3-triazolo[4,5-b]pyridinium 3-oxid hexafluorophosphate) (854 mg, 2.25 mmol) were charged in a round bottom flask and dissolved in DMF (dimethylformamide) (10.0 mL). To the solution was added N,N-diisopropylethylamine (0.80 mL, 4.49 mmol) at a rapid dropwise rate. After addition was complete, the reaction mixture was stirred at room temperature for about 15 minutes to provide the intermediate N—((S)-1-(3-(4-chloro-3-(N-(methylsulfonyl)methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide which was not isolated (MS (m/z) 1046.65 [M+H]$^+$). To the solution was added 2N aq. sodium hydroxide solution (5.0 mL). The mixture was stirred at room temperature for about 30 minutes. The reaction mixture was partitioned between water and ethyl acetate. The organic layer was collected and washed with two portions of 5% lithium chloride solution followed by brine. The organic layer was isolated, dried over sodium sulfate, filtered, and concentrated under vacuum. The resulting residue was purified by silica gel column chromatography to yield the title compound as an amorphous solid. MS (m/z) 968.24 [M+H]$^+$. $^1$H NMR (400 MHz, Methanol-d$_4$) δ 7.87-7.57 (m), 7.33-7.09 (m), 6.80-6.70 (m), 6.54 (d), 6.47 (d), 6.37-6.19 (m), 5.02-4.94 (m), 4.90-4.70 (m), 4.70-4.51 (m), 3.94 (dq), 3.32-3.28 (m), 3.23 (d), 3.07 (dd, J=13.1, 7.6 Hz), 2.93 (dd), 2.68-2.35 (m), 1.81 (s), 1.41 (q), 1.12-1.00 (m). $^{19}$F NMR (377 MHz, Methanol-d$_4$) δ −63.65, −71.78 (t), −72.35 (t), −82.75 (dd), −105.70 (ddd), −111.73 to −113.10 (m).

Example 2. N—((S)-1-(3-(4-Chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide N,N,N-trimethylethanolammonium (Choline) Salt 100 mg of Compound 1 and 25 mg of choline hydroxide solution (50% in water, 1 eq.) were stirred in about 1 mL isopropyl alcohol (IPA). The mixture was dried to afford amorphous solids. About 1 mL IPA was added to the solids, which remained as amorphous solids after stirring for about 2 hours. 10 μL of water was added, and the solids were mostly dissolved. The solution was held at about 21° C. and it crystallized over several days. The crystals, which were obtained after filtration and drying at about 50° C. under vacuum, were designated as the N,N,N-trimethylethanolammonium (choline) salt of Compound 1, crystalline Form I. $^1$H-NMR showed that the N,N,N-trimethylethanolammonium (choline) salt of Compound 1, crystalline Form I was enriched in Isomer B, as shown in FIG. 1 (top trace).

Figure 2:
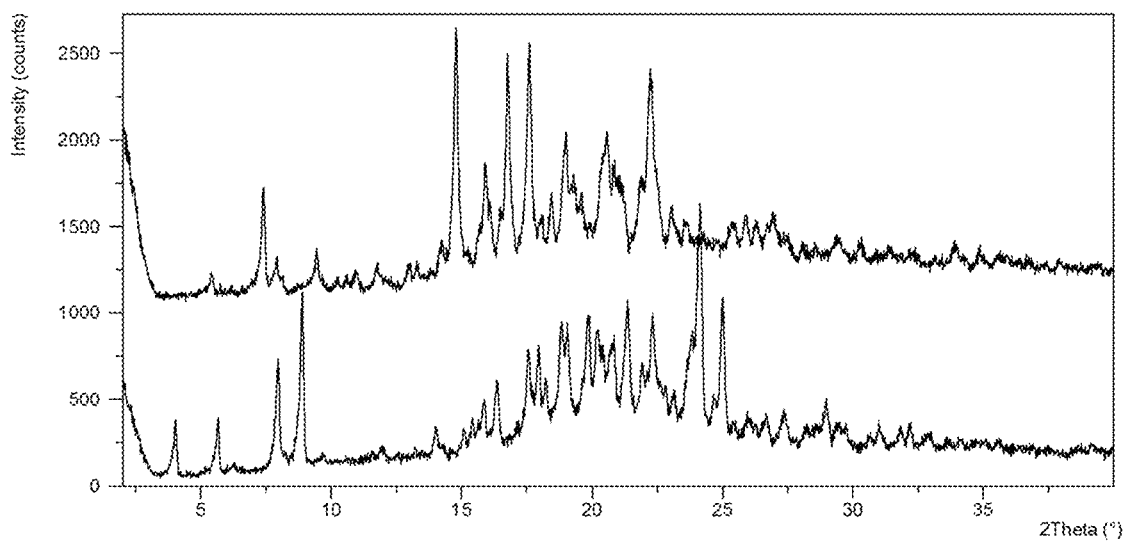
FIG. 2 shows an XRPD pattern characteristic of the N,N,N-trimethylethanolammonium (choline) salt of Compound 1 from isopropyl alcohol (top trace: bulk crystals; bottom trace: needles).

The crystals from the experiment described above were initially bulky crystals. After two months at ambient conditions in a sealed vial without agitation, the crystals became needles. XRPD showed a different pattern for the needles, when compared to the original bulky crystals, as shown in FIG. 2.

1H-NMR spectrum confirmed the needle crystals were still the choline salt, but enriched in Isomer A (FIG. 1, bottom trace). UPLC (Ultra Performance Liquid Chromatography) analysis showed that it contains about 64.8% Isomer A and about 35.1% Isomer B. After drying, this material lost crystallinity, as shown in FIG. 3 and was designated as the N,N,N-trimethylethanolammonium (choline) salt of Compound 1, Material A. Additional experiments were conducted by stirring either the N,N,N-trimethylethanolammonium (choline) salt of Compound 1, crystalline Form I or Material A in other solvents at about 22° C. The salts formed from MeOH, DCM, or toluene were enriched in Isomer B and the salts from MeCN, 2-MeTHF, i-PrOAc, EtOH, THF, or MTBE were enriched in Isomer A.

Form I

The N,N,N-trimethylethanolammonium (choline) salt of Compound 1, crystalline Form I was enriched in Isomer B and were prepared as described above. The XRPD pattern of the N,N,N-trimethylethanolammonium (choline) salt of Compound 1, crystalline Form I is shown in FIG. 4. A list of 2-theta peaks is provided in Table 1 below.

TABLE 1

| Peak No. | 2-theta | Rel. Int. (%) |
| --- | --- | --- |
| 1 | 5.5 | 7 |
| 2 | 7.5 | 41 |
| 3 | 7.9 | 23 |
| 4 | 9.8 | 16 |
| 5 | 13.1 | 12 |
| 6 | 14.2 | 11 |
| 7 | 14.9 | 100 |
| 8 | 15.7 | 73 |
| 9 | 16.0 | 45 |
| 10 | 16.8 | 68 |
| 11 | 17.6 | 78 |
| 12 | 19.3 | 46 |
| 13 | 20.8 | 35 |
| 14 | 21.6 | 36 |
| 15 | 22.4 | 57 |
| 16 | 23.6 | 25 |
| 17 | 26.8 | 12 |

The DSC thermogram of the N,N,N-trimethylethanolammonium (choline) salt of Compound 1, crystalline Form I is shown in FIG. 5 and exhibited a melting onset of about 157° C.

Form II

The N,N,N-trimethylethanolammonium (choline) salt of Compound 1, crystalline Form II was enriched in Isomer B and was obtained by slurrying the N,N,N-trimethylethanolammonium (choline) salt of Compound 1, crystalline Form I in MeOH/IPE (1:1 mixture by volume) for one week at about 22° C., filtering, and drying the solids at about 22 to about 50° C. under vacuum.

The XRPD pattern of the N,N,N-trimethylethanolammonium (choline) salt of Compound 1, crystalline Form II is shown in FIG. 6. A list of 2-theta peaks is provided in Table 2 below.

TABLE 2

| Peak No. | 2-theta | Rel. Int. (%) |
| --- | --- | --- |
| 1 | 7.5 | 16 |
| 2 | 9.6 | 15 |
| 3 | 14.0 | 11 |
| 4 | 14.7 | 36 |
| 5 | 14.9 | 43 |
| 6 | 16.1 | 43 |
| 7 | 16.9 | 100 |
| 8 | 18.5 | 17 |
| 9 | 19.1 | 21 |
| 10 | 19.6 | 19 |
| 11 | 20.2 | 22 |
| 12 | 20.8 | 56 |
| 13 | 21.0 | 36 |
| 14 | 22.5 | 18 |
| 15 | 23.3 | 16 |
| 16 | 24.5 | 20 |
| 17 | 25.4 | 11 |
| 18 | 26.5 | 28 |
| 19 | 27.8 | 18 |
| 20 | 30.7 | 13 |
| 21 | 33.0 | 6 |
| 22 | 34.1 | 7 |
| 23 | 35.2 | 11 |

The DSC thermogram of the N,N,N-trimethylethanolammonium (choline) salt of Compound 1, crystalline Form II is shown in FIG. 7 and exhibited a melting onset of about 147° C.

Form III

The N,N,N-trimethylethanolammonium (choline) salt of Compound 1, crystalline Form III was enriched in Isomer B and obtained by slurrying the N,N,N-trimethylethanolammonium (choline) salt of Compound 1, crystalline Form I or Material A in DCM/heptane mixture (1:1 mixture by volume) at about 22° C. for about 24 h, filtering, and drying the solids at about 50° C. under vacuum.

The XRPD pattern of the N,N,N-trimethylethanolammonium (choline) salt of Compound 1, crystalline Form III is shown in FIG. 8. A list of 2-theta peaks is provided in Table 3 below.

TABLE 3

| Peak No. | 2-theta | Rel. Int. (%) |
| --- | --- | --- |
| 1 | 7.8 | 30 |
| 2 | 8.1 | 29 |
| 3 | 8.3 | 23 |
| 4 | 9.8 | 16 |
| 5 | 11.4 | 8 |
| 6 | 12.3 | 7 |
| 7 | 13.6 | 4 |
| 8 | 14.1 | 15 |
| 9 | 15.0 | 36 |
| 10 | 15.7 | 100 |
| 11 | 16.2 | 31 |
| 12 | 16.7 | 46 |
| 13 | 17.6 | 35 |
| 14 | 18.1 | 31 |
| 15 | 19.2 | 28 |
| 16 | 19.4 | 30 |
| 17 | 20.0 | 53 |
| 18 | 21.1 | 37 |
| 19 | 21.7 | 53 |
| 20 | 22.3 | 17 |
| 21 | 23.0 | 26 |
| 22 | 23.7 | 20 |
| 23 | 24.8 | 8 |
| 24 | 26.9 | 10 |

The DSC thermogram of the N,N,N-trimethylethanolammonium (choline) salt of Compound 1, crystalline Form III is shown in FIG. 9 and exhibited a melting onset of about 144° C.

Form IV

The N,N,N-trimethylethanolammonium (choline) salt of Compound 1, crystalline Form IV is enriched in Isomer B and was obtained by slurrying the N,N,N-trimethylethanolammonium (choline) salt of Compound 1, crystalline Form I or Material A in toluene for about 2 weeks at about 22° C., filtering, and drying the solids at about 50° C. under vacuum. The XRPD pattern of the N,N,N-trimethylethanolammonium (choline) salt of Compound 1, crystalline Form IV is shown in FIG. 10. A list of 2-theta peaks is provided in Table 4 below.

TABLE 4

| Peak No. | 2-theta | Rel. Int. (%) |
| --- | --- | --- |
| 1 | 7.5 | 20 |
| 2 | 8.0 | 24 |
| 3 | 9.5 | 12 |
| 4 | 9.9 | 10 |
| 5 | 11.9 | 7 |
| 6 | 14.0 | 11 |
| 7 | 14.8 | 57 |

TABLE 4-continued

| Peak No. | 2-theta | Rel. Int. (%) |
|---|---|---|
| 8 | 16.1 | 19 |
| 9 | 17.0 | 100 |
| 10 | 18.6 | 11 |
| 11 | 19.7 | 21 |
| 12 | 20.3 | 72 |
| 13 | 21.1 | 44 |
| 14 | 21.7 | 22 |
| 15 | 22.3 | 25 |
| 16 | 23.7 | 23 |
| 17 | 24.6 | 21 |
| 18 | 25.6 | 9 |
| 19 | 26.7 | 29 |
| 20 | 27.7 | 12 |
| 21 | 29.6 | 7 |
| 22 | 30.9 | 12 |

The DSC thermogram of the N,N,N-trimethylethanolammonium (choline) salt of Compound 1, crystalline Form IV is shown in FIG. 11 and exhibited a melting onset of about 136° C.

Form V

The N,N,N-trimethylethanolammonium (choline) salt of Compound 1, Form V was enriched in Isomer A and was prepared by slurrying the N,N,N-trimethylethanolammonium (choline) salt of Compound 1, Material A in MeCN/IPE (1:1 mixture by volume) at about 22° C., filtering, and drying the solids at about 50° C. under vacuum.

The XRPD pattern of the N,N,N-trimethylethanolammonium (choline) salt of Compound 1, crystalline Form V is shown in FIG. 12. A list of 2-theta peaks is provided in Table 5 below.

TABLE 5

| Peak No. | 2-theta | Rel. Int. (%) |
|---|---|---|
| 1 | 6.9 | 28 |
| 2 | 7.9 | 54 |
| 3 | 10.7 | 52 |
| 4 | 11.9 | 15 |
| 5 | 12.5 | 31 |
| 6 | 12.9 | 19 |
| 7 | 14.0 | 20 |
| 8 | 14.5 | 49 |
| 9 | 14.8 | 34 |
| 10 | 15.6 | 43 |
| 11 | 15.9 | 61 |
| 12 | 16.7 | 53 |
| 13 | 17.0 | 45 |
| 14 | 17.3 | 53 |
| 15 | 17.6 | 100 |
| 16 | 17.8 | 62 |
| 17 | 18.7 | 28 |
| 18 | 19.1 | 22 |
| 19 | 19.6 | 18 |
| 20 | 21.1 | 65 |
| 21 | 21.8 | 59 |
| 22 | 22.8 | 62 |
| 23 | 23.2 | 45 |
| 24 | 23.9 | 33 |
| 25 | 24.4 | 6 |
| 26 | 25.1 | 10 |
| 27 | 25.7 | 24 |
| 28 | 26.0 | 29 |
| 29 | 26.9 | 48 |
| 30 | 27.3 | 29 |
| 31 | 28.1 | 9 |
| 32 | 29.1 | 26 |
| 33 | 31.4 | 11 |
| 34 | 31.7 | 22 |
| 35 | 35.0 | 12 |

The DSC thermogram of the N,N,N-trimethylethanolammonium (choline) salt of Compound 1, crystalline Form V is shown in FIG. 13 and exhibited a melting onset of about 159° C.

Form VI

The N,N,N-trimethylethanolammonium (choline) salt of Compound 1, crystalline Form VI was enriched in Isomer A and was prepared by slurrying the N,N,N-trimethylethanolammonium (choline) salt of Compound 1, Material A in 2-MeTHF at about 22° C. for about 24 h, filtering, and drying the solids at about 50° C. under vacuum.

The XRPD pattern of the N,N,N-trimethylethanolammonium (choline) salt of Compound 1, crystalline Form VI is shown in FIG. 14. A list of 2-theta peaks is provided in Table 6 below.

TABLE 6

| Peak No. | 2-theta | Rel. Int. (%) |
|---|---|---|
| 1 | 4.2 | 5 |
| 2 | 6.1 | 21 |
| 3 | 8.6 | 63 |
| 4 | 9.5 | 26 |
| 5 | 11.7 | 9 |
| 6 | 13.8 | 14 |
| 7 | 15.4 | 20 |
| 8 | 16.6 | 18 |
| 9 | 18.3 | 25 |
| 10 | 19.1 | 28 |
| 11 | 20.4 | 100 |
| 12 | 21.9 | 53 |
| 13 | 22.5 | 55 |
| 14 | 24.2 | 37 |
| 15 | 25.2 | 34 |
| 16 | 28.3 | 9 |

The DSC thermogram of the N,N,N-trimethylethanolammonium (choline) salt of Compound 1, Form VI is shown in FIG. 15 and exhibited a melting onset of about 121° C.

Form VII

The N,N,N-trimethylethanolammonium (choline) salt of Compound 1, crystalline Form VII was enriched in Isomer A and was prepared by slurrying the N,N,N-trimethylethanolammonium (choline) salt of Compound 1, Material A in i-PrOAc at about 22° C. for about 24 h, filtering, and drying the solids at about 50° C. under vacuum.

The XRPD pattern The N,N,N-trimethylethanolammonium (choline) salt of Compound 1, crystalline Form VII is shown in FIG. 16. A list of 2-theta peaks is provided in Table 7 below.

TABLE 7

| Peak No. | 2-theta | Rel. Int. (%) |
|---|---|---|
| 1 | 4.7 | 13 |
| 2 | 5.5 | 3 |
| 3 | 7.3 | 100 |
| 4 | 8.9 | 88 |
| 5 | 9.5 | 76 |
| 6 | 13.3 | 13 |
| 7 | 14.0 | 15 |
| 8 | 15.2 | 18 |
| 9 | 16.4 | 15 |
| 10 | 17.6 | 9 |
| 11 | 18.3 | 29 |
| 12 | 19.6 | 24 |
| 13 | 20.5 | 32 |
| 14 | 21.5 | 27 |
| 15 | 22.3 | 55 |
| 16 | 23.9 | 9 |
| 17 | 24.9 | 36 |

TABLE 7-continued

| Peak No. | 2-theta | Rel. Int. (%) |
|---|---|---|
| 18 | 26.5 | 8 |
| 19 | 28.4 | 18 |
| 20 | 30.7 | 3 |
| 21 | 35.8 | 3 |

The DSC thermogram of the N,N,N-trimethylethanolammonium (choline) salt of Compound 1, crystalline Form VII is shown in FIG. 17 and exhibited a melting onset of about 144° C.

Example 3. N—((S)-1-(3-(4-Chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-M-cyclopropa[3,4]cyclopenta[1,2-c]pyrazol-1-yl) acetamide N,N,N-trimethylethanolammonium (Choline) Salt, Ethanol Solvate The ethanol solvate form of the N,N,N-trimethylethanolammonium (choline) salt of Compound 1 was enriched in Isomer A and was prepared by slurrying the N,N,N-trimethylethanolammonium (choline) salt of Compound 1, crystalline Form I or Material A in EtOH/heptane mixture (1:1 mixture by volume) at about 22° C. for about 24 h. The XRPD pattern of the ethanol solvate form is shown in FIG. 18. After drying, this material lost crystallinity.

Example 4. N—((S)-1-(3-(4-Chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-M-cyclopropa[3,4]cyclopenta[1,2-c]pyrazol-1-yl) acetamide N,N,N-trimethylethanolammonium (Choline) Salt, Tetrahydrofuran (THF) Solvate The tetrahydrofuran (THF) solvate form of the N,N,N-trimethylethanolammonium (choline) salt of Compound 1 was enriched in Isomer A and was prepared by slurrying the N,N,N-trimethylethanolammonium (choline) salt of Compound 1, crystalline Form I or Material A in THF/heptane mixture (1:1 mixture by volume) at about 22° C. for about 24 h. The XRPD pattern of the tetrahydrofuran solvate form is shown in FIG. 19. After drying, this material lost crystallinity.

Example 5. N—((S)-1-(3-(4-Chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-03bS,4aR)-5,5-difluoro-3-(trifluoromethyl)-3b,4,4a,5-tetrahydro-M-cyclopropa[3,4]cyclopenta[1,2-c]pyrazol-1-yl) acetamide N,N,N-trimethylethanolammonium (Choline) Salt, Methyl Tert-Butyl Ether (MTBE) Solvate The methyl tert-butyl ether (MTBE) solvate form of the N,N,N-trimethylethanolammonium (choline) salt of Compound 1 was enriched in Isomer A and was prepared by slurrying the N,N,N-trimethylethanolammonium (choline) salt of Compound 1, Material A in MTBE at about 22° C. for about two weeks. The XRPD pattern of the methyl tert-butyl ether (MTBE) solvate is shown in FIG. 20. After drying, this material lost crystallinity.

Representative synthesis of the compounds described herein can also be found in U.S. patent application Ser. No. 15/680,041, filed Aug. 17, 2017, which published as U.S. Patent Application No. 2018-0051005 A1 on Feb. 22, 2018, the entire contents of which are incorporated herein by reference in their entireties.

BIOLOGICAL EXAMPLES

Example A

Test A: Antiviral Assay in MT4 Cells

For the antiviral assay, 0.4 µL of 189× test concentration of 3-fold serially diluted compound in DMSO was added to 40 µL of cell growth medium (RPMI 1640, 10% FBS, 1% Penicillin-Streptomycin, 1% L-Glutamine, 1% HEPES) in each well of 384-well plate (10 concentrations) in quadruplicate.

1 mL Aliquots of MT4 cells were pre-infected for 3 hours at 37° C. with 25 µL of cell growth medium (mock-infected) or a fresh 1:250 dilution of an HIV-IIIb concentrated ABI stock (0.004 m.o.i.). Infected and uninfected cells were diluted in cell growth media and 35 µL (2000 cells) was added to each well of the assay plates.

Assay plates were then maintained in a humidified, 5% $CO_2$ incubator at 37° C. After 5 days of incubation, 25 µL of 2× concentrated CellTiter-Glo™ Reagent (catalog #G7573, Promega Biosciences, Inc., Madison, Wis.) was added to each well of the assay plate. Cell lysis was carried out by incubating at room temperature for 10 minutes and then chemiluminescence was read using an Envision plate reader (PerkinElmer). $EC_{50}$ values were calculated as the compound concentration that caused a 50% decrease in luminescence signal, a measure of HIV-1 replication.

As described in Examples B-D, Compound 1 provides advantages compared to structurally close compounds (herein designated as Compounds A and B) disclosed in U.S. Patent Publication Nos. 2014/0296266A1 and 2014/0303164A1:

Compound A

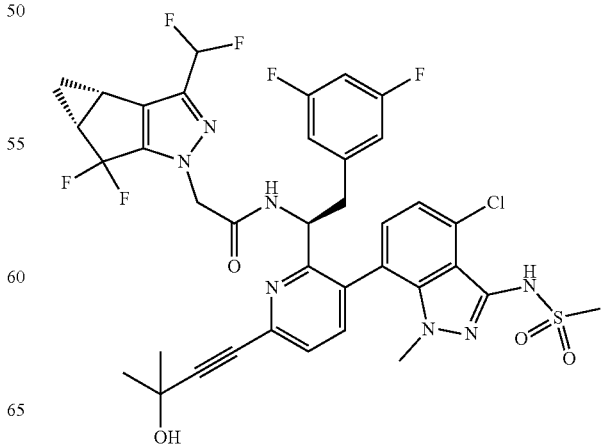

-continued

Compound B

[Chemical structure of Compound B]

Example B

Test B: Cytotoxicity Assay

Compound cytotoxicity and the corresponding $CC_{50}$ values was determined using the same protocol as described in the antiviral assay (Test A) except that uninfected cells were used.

The compound of the present disclosure demonstrates antiviral activity (Test A) as depicted in Table A in comparison to Compound A and Compound B.

TABLE A

| Compound | $EC_{50}$ (nM) | $CC_{50}$ (nM) |
|---|---|---|
| Compound 1 | 0.185 | 30068 |
| Compound A | 1.715 | 21839 |
| Compound B | 2.991 | 14491 |

Example C

Test C. Pharmacokinetic Analysis Following Intravenous Administration to Sprague-Dawley Rats and Beagle Dogs and Cynomologous Monkeys

Test Article and Formulation

Compound 1 IV administration was formulated in 5% ethanol, 20% PG, 45% PEG 300, 30% pH 2 (0.01N HCl) water at 0.5 mg/mL. Compound A and Compound B intravenous infusion doses were formulated in a sterile solution of 5% ethanol, 45% PEG 400 and 50% water (pH 2.0) at 0.5 mg/mL. All IV formulations were in solution.

Animals Used

Each rat IV dosing group consisted of 3 male SD rats. At dosing, the animals generally weighed between 0.317 and 0.355 kg. The animals were fasted overnight prior to dose administration and up to 4 hr after dosing. Each dog IV dosing group consisted of 3 male, naïve beagle dogs. At dosing, the animals weighed ~10-12 kg. The animals were fasted overnight prior to dose administration and up to 2 hr after dosing.

Each cynomolgus (cyno) monkey IV dosing group consisted of 3 male, naïve cyno monkeys At dosing, the animals weighed ~3.2-4 kg. The animals were fasted overnight prior to dose administration and up to 2 hr after dosing.

Dosing

For the IV infusion group, the test compound was administered by intravenous infusion over 30 minutes. The rate of infusion was adjusted according to the body weight of each animal to deliver a dose of 1 mg/kg at 2 mL/kg.

Sample Collection

Serial venous blood samples (approximately 0.4 mL each for rat and 1.0 mL for dog) were taken at specified time points after dosing from each animal. The blood samples were collected into Vacutainer™ tubes (Becton-Disckinson Corp, New Jersey, USA) containing EDTA as the anticoagulant and were immediately placed on wet ice pending centrifugation for plasma. Centrifugation began within 1 hour of collection. All samples were placed into 96-well tubes and maintained on dry ice prior to storage at approximately −70° C.

Determination of the Concentrations of Compound 1 in Plasma

An LC/MS/MS method was used to measure the concentration of test compounds in plasma.

Calculations

Non-compartmental pharmacokinetic analysis was performed on the plasma concentration-time data. A summary of pharmacokinetic parameters are shown in Tables B and C below.

TABLE B

| Compound | Rat CL (L/h/kg) | Rat $V_{ss}$ (L/kg) | Rat $t_{1/2}$ (h) | Dog CL (L/h/kg) | Dog $V_{ss}$ (L/kg) | Dog $t_{1/2}$ (h) | Cyno CL (L/h/kg) | Cyno $V_{ss}$ (L/kg) | Cyno $t_{1/2}$ (h) |
|---|---|---|---|---|---|---|---|---|---|
| Compound 1 | 0.05 | 1.8 | 28 | 0.07 | 1.6 | 22 | 0.24 | 2.7 | 12 |
| Compound A | 0.50 | 1.0 | 2 | 0.25 | 0.8 | 4 | 0.45 | 1.18 | 2.3 |
| Compound B | 0.43 | 1.4 | 3 | 0.28 | 1.3 | 6 | 0.42 | 1.59 | 3.4 |

CL: observed clearance;
Vss: volume of distribution at steady state;
$t_{1/2}$: terminal half-life

TABLE C

| Compound | Rat $C_{max}$ | Rat $AUC_{inf}$ (µM · h) | Dog $C_{max}$ | Dog $AUC_{inf}$ (µM · h) | Cyno $C_{max}$ | Cyno $AUC_{inf}$ (µM · h) |
|---|---|---|---|---|---|---|
| Compound 1 | 1.8 | 19 | 2.2 | 14.8 | 1.3 | 4.5 |
| Compound A | 1.4 | 2.7 | 2.1 | 5 | 1.8 | 2.6 |

TABLE C-continued

| Compound | Rat $C_{max}$ | Rat $AUC_{inf}$ (µM · h) | Dog $C_{max}$ | Dog $AUC_{inf}$ (µM · h) | Cyno $C_{max}$ | Cyno $AUC_{inf}$ (µM · h) |
|---|---|---|---|---|---|---|
| Compound B | 1.1 | 2.7 | 1.4 | 4.3 | 1.4 | 2.9 |

$AUC_{inf}$: Area Under the Curve from t = 0 to infinity;
$C_{max}$: Maximum plasma concentration Example D Test D. Metabolic Stability in Cultured Human Liver Hepatocytes Radiolabelled test compounds, wherein tritium was introduced into the structure in place of one or more hydrogens, were prepared according to known methods in the art.

The radiolabelled compounds were incubated in pooled cryopreserved hepatocytes at a substrate concentration of 0.25 µM and radioactivity concentration of 10 µCi/mL. The final hepatocyte concentration was 1 million cells/mL. The hepatocyte/compound reaction mixture was dissolved in InVitroGRO™ KHB buffer (catalog #Z99074, BioreclamationIVT, Inc., Baltimore, Md.) at pH 7.4. The incubations were performed in duplicate. A cell free control and a positive control were included in the incubations. The incubations were carried out with gentle shaking in a 37° C. incubator under a humid atmosphere of 95% air/5% $CO_2$ (v/v). Aliquots (100 mL) were removed after 0, 1, 3, and 6 hours and added to 200 mL quenching solution that comprised 0.1% (v/v) TFA in 5% water/95% acetonitrile (v/v). The samples were placed on a shaker for 10 min, followed by centrifugation at 3000 g for 30 min. The samples of the supernatant were analyzed on a Dionex HPLC/PerkinElmer Flow Scintillation Analyzer as described below.

Liquid Chromatography—Radiochromatography

Quantification was done by comparison of radiolabeled metabolites and parent peaks measured on a Radiomatic 625TR Flow Scintillation Analyzer coupled to a Dionex/Chromeleon chromatography system. The column was a Phenomenex Synergi fusion RP (150×4.6 mm, 4 mm) maintained at 32 degrees Celsius. Mobile Phase A consisted of 0.1% (v/v) TFA in 99% water/1% acetonitrile (v/v). Mobile Phase B consisted of 0.1% (v/v) TFA in 5% water/95% acetonitrile (v/v). The flow rate was 1 mL/min using a sample injection volume of 100 mL. Gradient was as following: Mobile phase B was linearly increased from 2% to 75% over 47 min, maintained at 75% for 3 min, changed back to 2%, maintained at 2% for 10 min.

Metabolic stability was determined by measuring the change in relative abundance of metabolites and parent over time and calculating from it the rate of disappearance of the parent compound. The stability data was utilized to calculate predicted human hepatic clearance values according to methods known in the art. The predicted human hepatic clearance values are shown in Table D below.

TABLE D

|  | Predicted Human Hepatic Clearance (L/hr/kg) |
|---|---|
| Compound 1 | 0.01 |
| Compound A | 0.09 |
| Compound B | 0.04 |

The following can be deduced from the above comparative data:

Compound 1 is more potent in an HIV antiviral assay relative to compounds A and B (about 9 and about 16 times more potent, respectively). Compound 1 has a longer in vivo terminal half-life in rat relative to compounds A and B (about 14 and about 9 times longer, respectively). Compound 1 has a lower in vivo clearance in rat relative to compounds A and B (about 10 and about 8.6 times lower, respectively). Compound 1 has a longer in vivo terminal half-life in dog relative to compounds A and B (about 5 and about 4 times longer, respectively). Compound 1 has a lower in vivo clearance in dog relative to compounds A and B (about 3 and about 4 times lower, respectively). Compound 1 is more stable in human hepatocytes with a lower predicted hepatic clearance relative to compounds A and B (about 9 and about 4 times more stable, respectively).

The above data demonstrate that Compound 1, has improved antiviral potency and an improved pharmacokinetic profile (which is demonstrated by longer half-life in rat and dog and lower predicted human clearance) when compared to compounds A and B.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present disclosure.

The Examples disclosed herein describe the synthesis of compounds, salts, and crystalline forms disclosed herein as well as intermediates used to prepare the compounds. It is to be understood that individual steps described herein may be combined. It is also to be understood that separate batches of a compound may be combined and then carried forth in the next synthetic step.

All references, including publications, patents, and patent documents are incorporated by reference herein, as though individually incorporated by reference. The present disclosure provides reference to various embodiments and techniques. However, it should be understood that many variations and modifications may be made while remaining within the spirit and scope of the present disclosure.

What is claimed is:

1. A method of treating or preventing a human immunodeficiency virus (HIV) infection comprising administering a therapeutically effective amount of a pharmaceutically acceptable salt, which is N—((S)-1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide N,N,N-trimethylethanolammonium salt, or the crystalline form of the salt, to a subject in need thereof.

2. The method of claim 1, wherein the method comprises administering the salt or crystalline form in combination with one, two, three, or four additional therapeutic agents.

3. The method of claim 2, wherein the additional therapeutic agents are selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or any combinations thereof.

4. The method of claim 2, wherein the additional therapeutic agents are selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, or any combinations thereof.

5. The method of claim 2, wherein the additional therapeutic agents are selected from the group consisting of 4'-ethynyl-2-fluoro-2'-deoxyadenosine, bictegravir or a pharmaceutically acceptable salt thereof, abacavir sulfate, tenofovir, tenofovir disoproxil, tenofovir disoproxil fumarate, tenofovir disoproxil hemifumarate, tenofovir alafenamide, and tenofovir alafenamide hemifumarate.

6. The method of claim 2, wherein the additional therapeutic agents are selected from the group consisting of 4'-ethynyl-2-fluoro-2'-deoxyadenosine, bictegravir or a pharmaceutically acceptable salt thereof, tenofovir alafenamide, tenofovir alafenamide fumarate and tenofovir alafenamide hemifumarate.

7. The method of claim 1, wherein the method comprises administering a therapeutically effective amount of N—((S)-1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide N,N,N-trimethylethanolammonium salt.

8. The method of claim 1, wherein the method comprises administering a therapeutically effective amount of a crystalline form of the salt of claim 1.

9. The method of claim 8, wherein the crystalline form is crystalline Form I.

10. The method of claim 9, wherein the crystalline Form I has at least three XRPD peaks, in terms of 2-theta±0.2°, selected from 5.5°, 7.5°, 7.9°, 14.9°, 15.7°, 16.8°, 17.6°, 19.3°, and 22.4°.

11. The method of claim 9, wherein the crystalline Form I is characterized by an XRPD pattern substantially as shown in FIG. 4.

12. The method of claim 9, wherein the crystalline Form I is characterized by a DSC thermogram having a melting onset of about 157° C.

13. The method of claim 9, wherein the crystalline Form I is characterized by a DSC thermogram substantially as shown in FIG. 5.

14. The method of claim 8, wherein the crystalline form is crystalline Form II.

15. The method of claim 14, wherein the crystalline Form II has at least three XRPD peaks, in terms of 2-theta±0.2°, selected from 7.5°, 9.6°, 14.0°, 14.9°, 16.1°, 16.9°, 20.8°, 21.0°, and 26.5°.

16. The method of claim 14, wherein the crystalline Form II is characterized by an XRPD pattern substantially as shown in FIG. 6.

17. The method of claim 14, wherein the crystalline Form II is characterized by a DSC thermogram having a melting onset of about 147° C.

18. The method of claim 14, wherein the crystalline Form II is characterized by a DSC thermogram substantially as shown in FIG. 7.

19. The method of claim 8, wherein the crystalline form is crystalline Form III.

20. The method of claim 19, wherein the crystalline Form III has at least three XRPD peaks, in terms of 2-theta±0.2°, selected from 7.8°, 8.1°, 8.3°, 15.0°, 15.7°, 16.7°, 20.0°, 21.1°, and 21.7°.

21. The method of claim 19, wherein the crystalline Form III is characterized by an XRPD pattern substantially as shown in FIG. 8.

22. The method of claim 19, wherein the crystalline Form III is characterized by a DSC thermogram having a melting onset of about 144° C.

23. The method of claim 19, wherein the crystalline Form III is characterized by a DSC thermogram substantially as shown in FIG. 9.

* * * * *

UNITED STATES PATENT AND TRADEMARK OFFICE
CERTIFICATE OF CORRECTION

| | |
|---|---|
| PATENT NO. | : 11,266,638 B2 |
| APPLICATION NO. | : 16/892377 |
| DATED | : March 8, 2022 |
| INVENTOR(S) | : Houston et al. |

It is certified that error appears in the above-identified patent and that said Letters Patent is hereby corrected as shown below:

On the Title Page

Column 2, Line 2, (Other Publications), delete "diazatricylo" and insert -- diazatricyclo --;

Column 2, Line 2, (Abstract), delete "((S" and insert -- ((S) --.

In the Claims

Column 64, Line 54, Claim 1, delete "the crystalline form" and insert -- a crystalline form --.

Signed and Sealed this
Twenty-eighth Day of June, 2022

Katherine Kelly Vidal
*Director of the United States Patent and Trademark Office*